US008496684B2

(12) United States Patent
Crainich et al.

(10) Patent No.: US 8,496,684 B2
(45) Date of Patent: Jul. 30, 2013

(54) METHOD FOR DEPLOYING A DEVICE FOR GASTRIC VOLUME REDUCTION

(75) Inventors: Lawrence Crainich, Charlestown, NH (US); Mark S. Zeiner, Mason, OH (US); Michael J. Stokes, Cincinnati, OH (US); Daniel Alesi, Lebanon, OH (US); Jason L. Harris, Mason, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1179 days.

(21) Appl. No.: 11/930,281

(22) Filed: Oct. 31, 2007

(65) Prior Publication Data
US 2009/0112232 A1    Apr. 30, 2009

(51) Int. Cl.
*A61B 17/04* (2006.01)
(52) U.S. Cl.
USPC ........................................... 606/232
(58) Field of Classification Search
USPC .................. 606/142–150, 232; 623/23.72; 227/175.1–182.1
See application file for complete search history.

(56) References Cited

U.S. PATENT DOCUMENTS

| 4,235,238 | A | 11/1980 | Ogiu et al. |
| 4,705,040 | A | 11/1987 | Mueller et al. |
| 4,741,330 | A | 5/1988 | Hayhurst |
| 4,760,848 | A | 8/1988 | Hasson |
| 5,041,129 | A | 8/1991 | Hayhurst |
| 5,217,470 | A | 6/1993 | Weston |
| 5,562,684 | A | 10/1996 | Kammerer |
| 5,601,557 | A | 2/1997 | Hayhurst |
| 5,626,614 | A | 5/1997 | Hart |
| 5,749,898 | A | 5/1998 | Schulze et al. |
| 5,810,848 | A | 9/1998 | Hayhurst |
| 5,865,361 | A | 2/1999 | Milliman et al. |
| 5,893,592 | A | 4/1999 | Schulze et al. |
| 6,125,852 | A | 10/2000 | Stevens et al. |
| 6,143,017 | A | 11/2000 | Thal |

(Continued)

FOREIGN PATENT DOCUMENTS

| EP | 1762185 A1 | 3/2007 |
| WO | WO 2005/065412 A | 7/2005 |
| WO | WO 2005/110280 A2 | 11/2005 |
| WO | WO 2006/044837 A2 | 4/2006 |

OTHER PUBLICATIONS

Alfieri, et al., "Novel Suture Device for Beating-Heart Mitral Leaflet Approximation", 2002, Ann Thorac Surg., 74:1488-93.

(Continued)

*Primary Examiner* — Melanie Tyson

(57) ABSTRACT

A method for approximating tissue within a body including the step of providing a device having a handle, at least one actuator, an elongated hollow housing having a proximal end attached to the handle and a distal end extending therefrom, a first and second cartridge. Each the cartridge contains at least one fastener having at least two anchors connected together by a non-resilient flexible suture which does not resist deformation under compressible loads. The first cartridge being releasably connected to the distal end of hollow housing. The method also includes the step of inserting the first cartridge into a body and deploying each anchor into tissue in a spaced apart position. The method also involves moving the anchors adjacent one another by moving the suture in a proximal direction, and removing the first cartridge from the body and from the housing. The method then involves placing the second cartridge onto the housing thereby replacing the first cartridge with the second cartridge.

4 Claims, 57 Drawing Sheets

U.S. PATENT DOCUMENTS

| | | |
|---|---|---|
| 6,319,271 B1 | 11/2001 | Schwartz et al. |
| 6,500,184 B1 | 12/2002 | Chan |
| 6,558,400 B2 | 5/2003 | Deem et al. |
| 6,561,969 B2 | 5/2003 | Frazier et al. |
| 6,572,629 B2 | 6/2003 | Kalloo et al. |
| 6,663,639 B1 | 12/2003 | Laufer et al. |
| 6,767,037 B2 | 7/2004 | Wenstrom, Jr. |
| 7,153,312 B1 | 12/2006 | Torrie et al. |
| 7,175,638 B2 | 2/2007 | Gannoe et al. |
| 7,288,099 B2 | 10/2007 | Deem et al. |
| 7,731,725 B2 * | 6/2010 | Gadberry et al. ............. 606/143 |
| 2002/0019649 A1 | 2/2002 | Sikora et al. |
| 2003/0130694 A1 | 7/2003 | Bojarski et al. |
| 2003/0163160 A1 | 8/2003 | O'Malley et al. |
| 2004/0049211 A1 | 3/2004 | Tremulis |
| 2004/0162568 A1 | 8/2004 | Saadat et al. |
| 2004/0186514 A1 | 9/2004 | Swain et al. |
| 2004/0194790 A1 | 10/2004 | Laufer et al. |
| 2004/0225305 A1 | 11/2004 | Ewers et al. |
| 2005/0033363 A1 | 2/2005 | Bojarski et al. |
| 2005/0059984 A1 | 3/2005 | Chanduszko et al. |
| 2005/0075654 A1 | 4/2005 | Kelleher |
| 2005/0149074 A1 | 7/2005 | Pugsley et al. |
| 2005/0177180 A1 | 8/2005 | Kaganov et al. |
| 2005/0187577 A1 | 8/2005 | Selvitelli et al. |
| 2005/0192632 A1 | 9/2005 | Geissler et al. |
| 2005/0216040 A1 | 9/2005 | Gertner et al. |
| 2005/0228415 A1 | 10/2005 | Gertner |
| 2005/0283192 A1 | 12/2005 | Torrie et al. |
| 2006/0009789 A1 | 1/2006 | Gambale et al. |
| 2006/0020277 A1 | 1/2006 | Gostout et al. |
| 2006/0064115 A1 | 3/2006 | Allen et al. |
| 2006/0142784 A1 | 6/2006 | Kontos |
| 2006/0178680 A1 | 8/2006 | Nelson et al. |
| 2006/0190042 A1 | 8/2006 | Stone et al. |
| 2006/0253131 A1 | 11/2006 | Wolniewicz, III |
| 2006/0264984 A1 | 11/2006 | Schurr et al. |
| 2006/0287661 A1 | 12/2006 | Bolduc et al. |
| 2006/0293709 A1 | 12/2006 | Bojarski et al. |
| 2007/0027358 A1 | 2/2007 | Gertner et al. |
| 2007/0027476 A1 * | 2/2007 | Harris et al. .................. 606/232 |
| 2007/0083236 A1 | 4/2007 | Sikora et al. |
| 2007/0093861 A1 | 4/2007 | Vardi |
| 2007/0173888 A1 | 7/2007 | Gertner et al. |
| 2009/0001126 A1 * | 1/2009 | Hess et al. ................. 227/176.1 |

OTHER PUBLICATIONS

Seaman, et al., "Tissue Anchors for Transmural Gut-Wall Apposition", Gastrointest Endosc., 64:577-81, 2006.
European Search Report dated Jun. 4, 2009, European Application No. 08253552.7.
European Search Report dated Mar. 24, 2012, European Application No. 08253541.0.

* cited by examiner

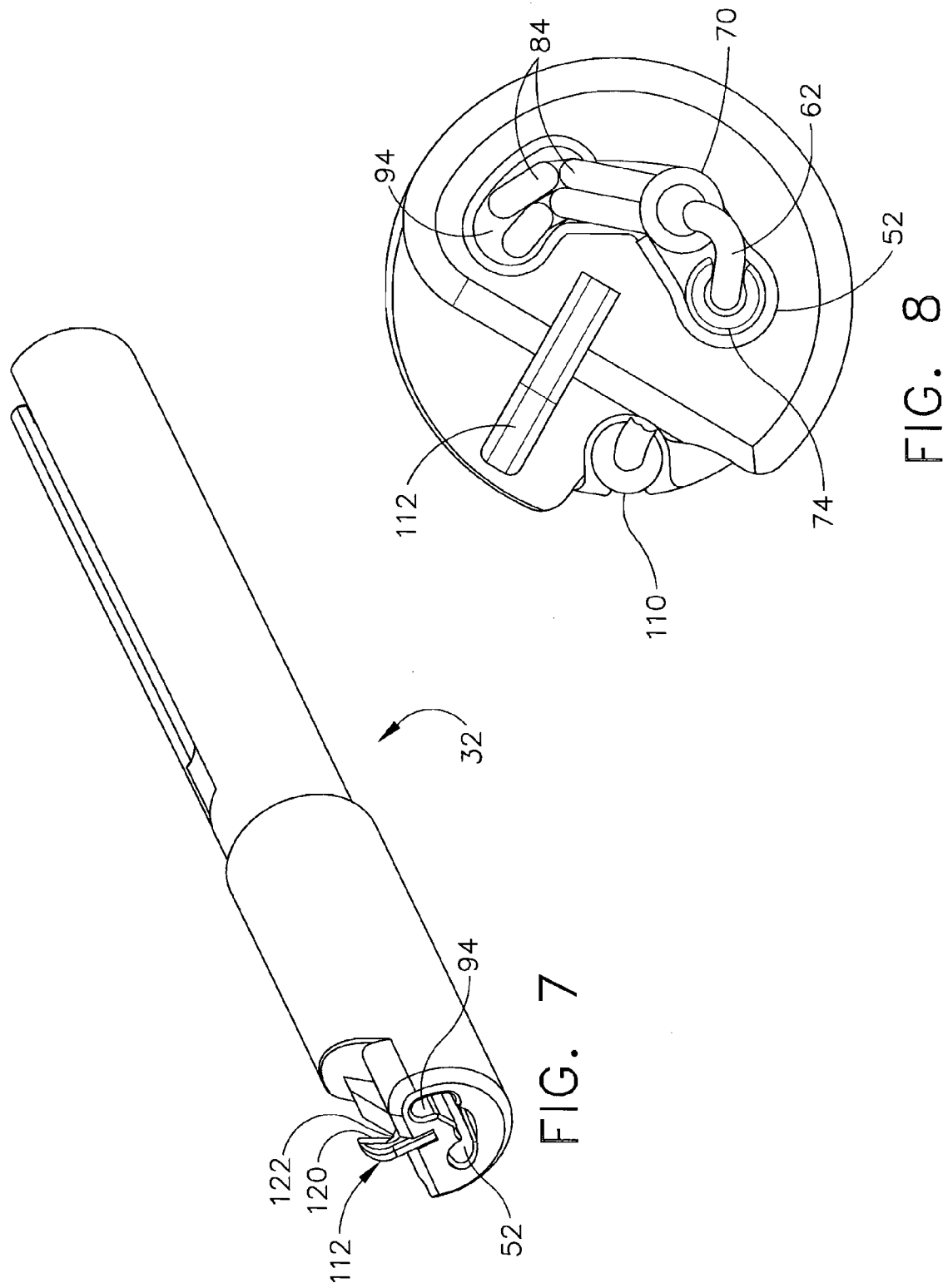

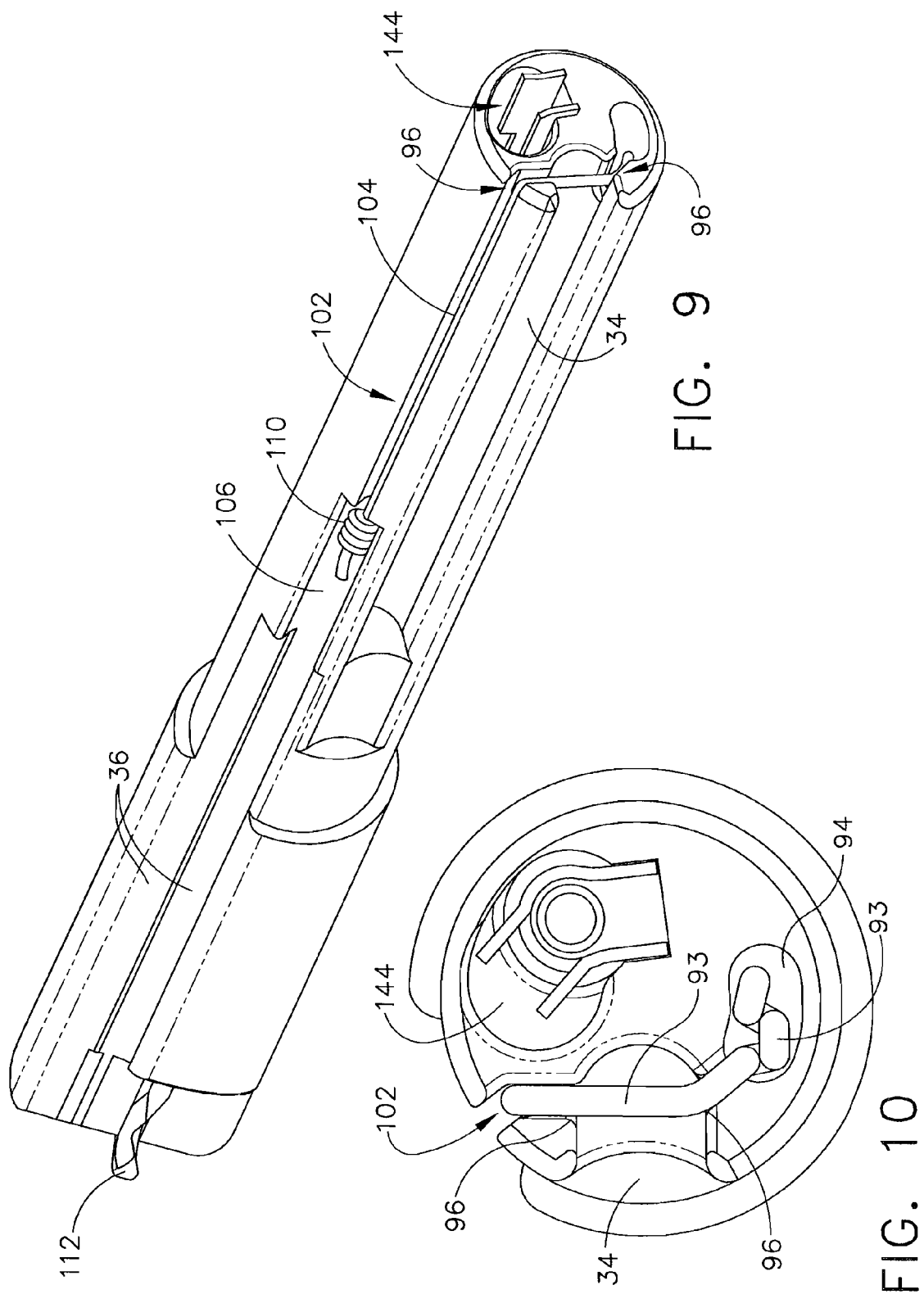

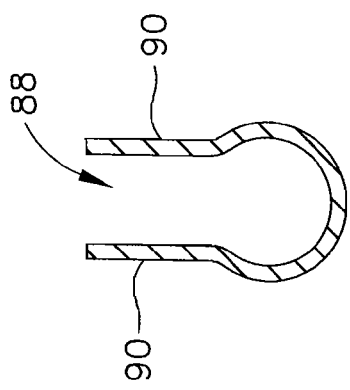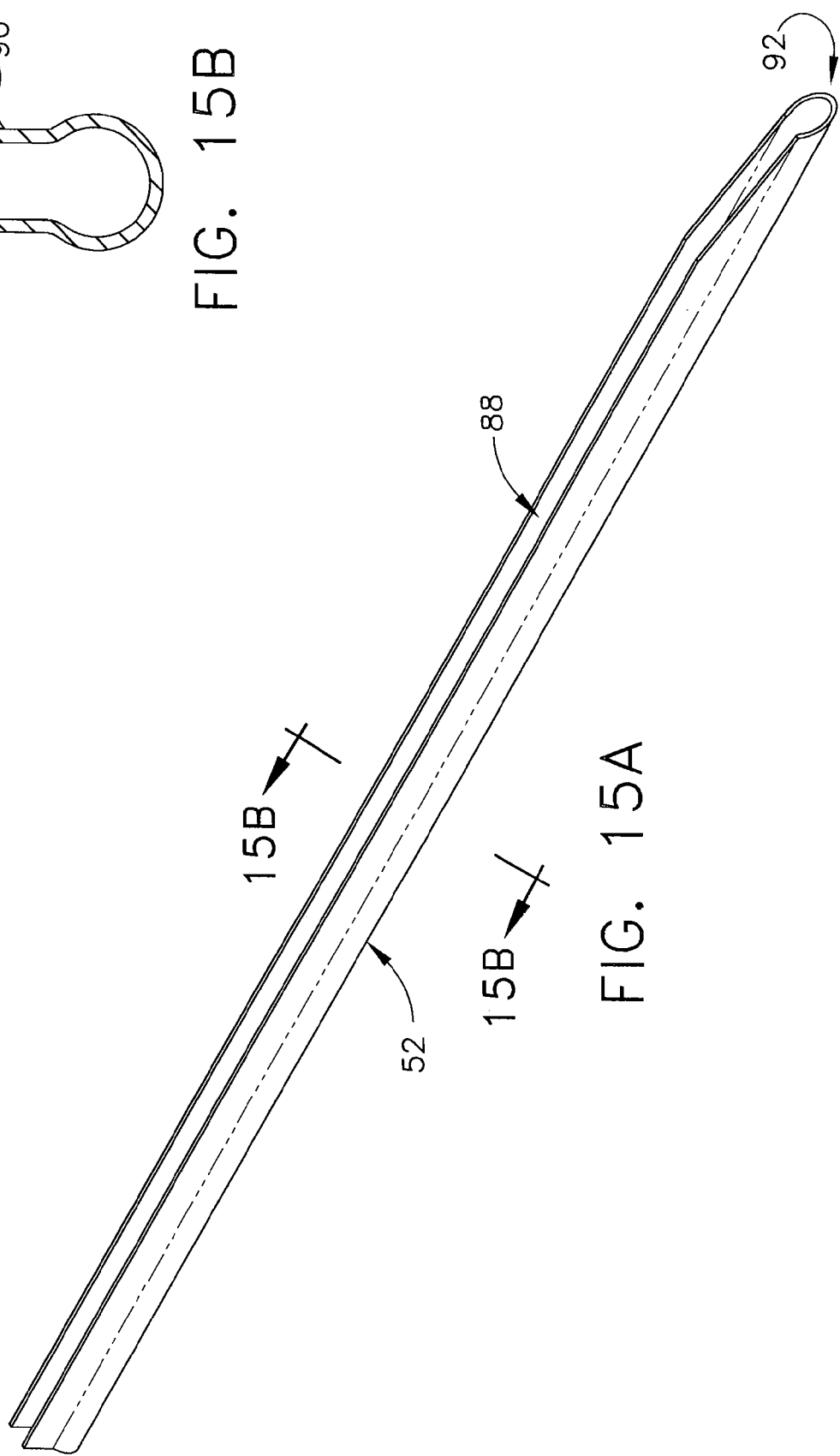

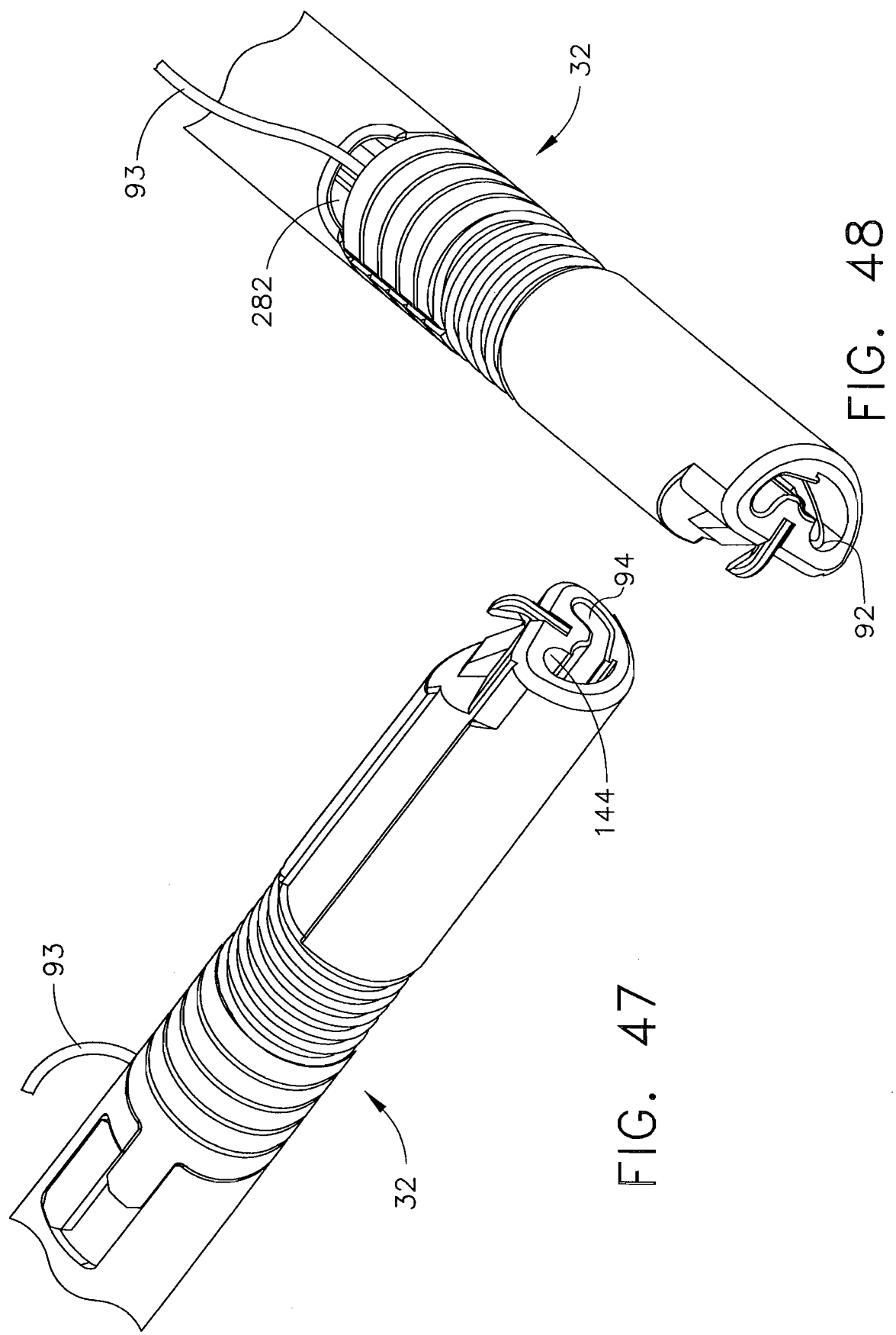

US 8,496,684 B2

METHOD FOR DEPLOYING A DEVICE FOR GASTRIC VOLUME REDUCTION

FIELD OF THE INVENTION

The present invention relates generally to gastric volume reduction surgery and, more particularly, to a reloadable laparoscopic device for approximating tissue during gastric volume reduction surgery. The laparoscopic device releasably connects to a disposable cartridge containing at least one fastener. The device deploys a fastener from the cartridge into the gastric cavity wall to facilitate involution of the wall and a reduction in the cavity volume.

BACKGROUND OF THE INVENTION

Obesity is a medical condition affecting more than 30% of the population in the United States. Obesity affects an individual's personal quality of life and contributes significantly to morbidity and mortality. Obesity is most commonly defined by body mass index (BMI), a measure which takes into account a person's weight and height to gauge total body fat. It is a simple, rapid, and inexpensive measure that correlates both with morbidity and mortality. Overweight is defined as a BMI of 25 to 29.9 kg/m2 and obesity as a BMI of 30 kg/m2. Morbid obesity is defined as BMI≧40 kg/m2 or being 100 lbs. overweight. Obesity and its co-morbidities are estimated to cost an excess of $100 billion dollars annually in direct and indirect health care costs. Among the co-morbid conditions which have been associated with obesity are type 2 diabetes mellitus, cardiovascular disease, hypertension, dyslipidemias, gastroesophageal reflux disease, obstructive sleep apnea, urinary incontinence, infertility, osteoarthritis of the weight-bearing joints, and some cancers. These complications can affect all systems of the body, and dispel the misconception that obesity is merely a cosmetic problem. Studies have shown that conservative treatment with diet and exercise alone may be ineffective for reducing excess body weight in many patients.

Bariatrics is the branch of medicine that deals with the control and treatment of obesity. A variety of surgical procedures have been developed within the bariatrics field to treat obesity. The most common currently performed procedure is the Roux-en-Y gastric bypass (RYGB). This procedure is highly complex and is commonly utilized to treat people exhibiting morbid obesity. In a RYGB procedure a small stomach pouch is separated from the remainder of the gastric cavity and attached to a resected portion of the small intestine. This resected portion of the small intestine is connected between the "smaller" gastric pouch and a distal section of small intestine allowing the passage of food therebetween. The conventional RYGB procedure requires a great deal of operative time and is not without procedure related risks. Because of the degree of invasiveness, post-operative recovery can be quite lengthy and painful. Still more than 100,000 RYGB procedures are performed annually in the United States alone, costing significant health care dollars.

In view of the highly invasive nature of the RYGB procedure, other less invasive procedures have been developed. These procedures include gastric banding, which constricts the stomach to form an hourglass shape. This procedure restricts the amount of food that passes from one section of the stomach to the next, thereby inducing an early feeling of satiety. A band is placed around the stomach near the junction of the stomach and esophagus. The small upper stomach pouch is filled quickly, and slowly empties through the narrow outlet to produce the feeling of satiety. In addition to surgical complications, patients undergoing a gastric banding procedure may suffer from esophageal injury, spleen injury, band slippage, reservoir deflation/leak, and persistent vomiting. Other forms of bariatric surgery that have been developed to treat obesity include Fobi pouch, bilio-pancreatic diversion, vertical banded gastroplasty and sleeve gastrectomy. As aspects of some of these procedures including RYGB involve stapling a portion of the stomach, many bariatric procedures are commonly referred to as "stomach stapling" procedures.

For morbidly obese individuals, RYGB, gastric banding or another of the more complex procedures may be the recommended course of treatment due to the significant health problems and mortality risks facing the individual. However, there is a growing segment of the population in the United States and elsewhere who are overweight without being considered morbidly obese. These persons may be 20-30 pounds overweight and want to lose the weight, but have not been able to succeed through diet and exercise alone. For these individuals, the risks associated with the RYGB or other complex procedures often outweigh the potential health benefits and costs. Accordingly, treatment options should involve a less invasive, lower cost solution for weight loss. Further, it is known that modest reductions in weight may significantly decrease the impact of co morbid conditions including, but not limited to type 2 diabetes mellitus. For this reason as well, a low cost, low risk procedure with an exceptional safety profile would provide significant benefit to both patients and health care providers.

It is known that creating cavity wall plications though endoscopic only procedures is a method to treat obesity. However, operating solely within the interior of the gastric cavity limits the plication depth that can be achieved without cutting. Furthermore, access and visibility within the gastric cavity is limited in a purely endoscopic procedure as the extent of the reduction increases.

A hybrid endoscopic/laparoscopic surgical procedure has been developed for involuting the gastric cavity wall to reduce stomach volume. In the hybrid gastric volume reduction (GVR) procedure, pairs of suture anchoring devices are deployed through the gastric cavity wall. Following deployment of the anchors, suture attached to each pair of anchors is cinched and secured to involute the cavity wall. This procedure is described in greater detail in co-pending U.S. patent application Ser. Nos. 11/779,314 and 11/779,322, which are hereby incorporated herein by reference.

To facilitate the hybrid endoscopic/laparoscopic GVR procedure (e.g., reduction gastroplasty), it is desirable to have a simple, low cost means for deploying fasteners into the gastric cavity. While the GVR procedure can be performed using a needle and suture, such an approach requires a highly skilled surgeon and can be time consuming. Accordingly, it is desirable to have a device that can discharge fasteners in response to a series of triggering actions by the surgeon. It is desirable that the device deploy fasteners through a laparoscopic port to maintain the minimally invasive nature of the procedure. Additionally, it is desirable to have a laparoscopic fastener deploying device that is inexpensive and easy to use. Further, it is desirable to have a fastener deploying device that is easily and quickly reloadable, so that the device can repeatably deploy as many fasteners as deemed necessary by the surgeon. It is desirable that the fasteners be packaged into an easy to load cartridge so that the procedure can be quickly and safely performed. The present invention provides a reloadable fastener deploying device and mating, replaceable fastener cartridge which achieves these objectives.

SUMMARY OF THE INVENTION

A cartridge containing a fastener, wherein the cartridge releasably connected to a fastener deploying device. The cartridge has a housing which houses at least one tissue penetrating member. The penetrating member at least partially houses a fastener. The fastener has at least two rigid anchors connected together by a flaccid member. The cartridge further includes a means for removably attaching the cartridge to a deployment device.

BRIEF DESCRIPTION OF THE DRAWINGS

FIG. 7 is perspective view of the cartridge showing the distal end and a side of the cartridge;

FIG. 8 is a distal end view of the cartridge shown in FIG. 7;

FIG. 9 is a second, perspective view of the cartridge shown in FIG. 7, showing the proximal end and top portions of the cartridge;

FIG. 10 is a proximal end view of the cartridge shown in FIG. 7:

FIG. 15A is a perspective view of a first embodiment for a needle usable within the cartridge of FIG. 7;

FIG. 15B is a cross-sectional view of the needle shown in FIG. 15A;

FIG. 47 is a perspective view of the cartridge for the third embodiment, showing a first side and distal end of the cartridge;

FIG. 48 is a perspective view of the cartridge for the third embodiment, showing the cartridge rotated 180° about the cartridge axis from the view shown in FIG. 47;

DETAILED DESCRIPTION OF THE INVENTION

Figure 1:
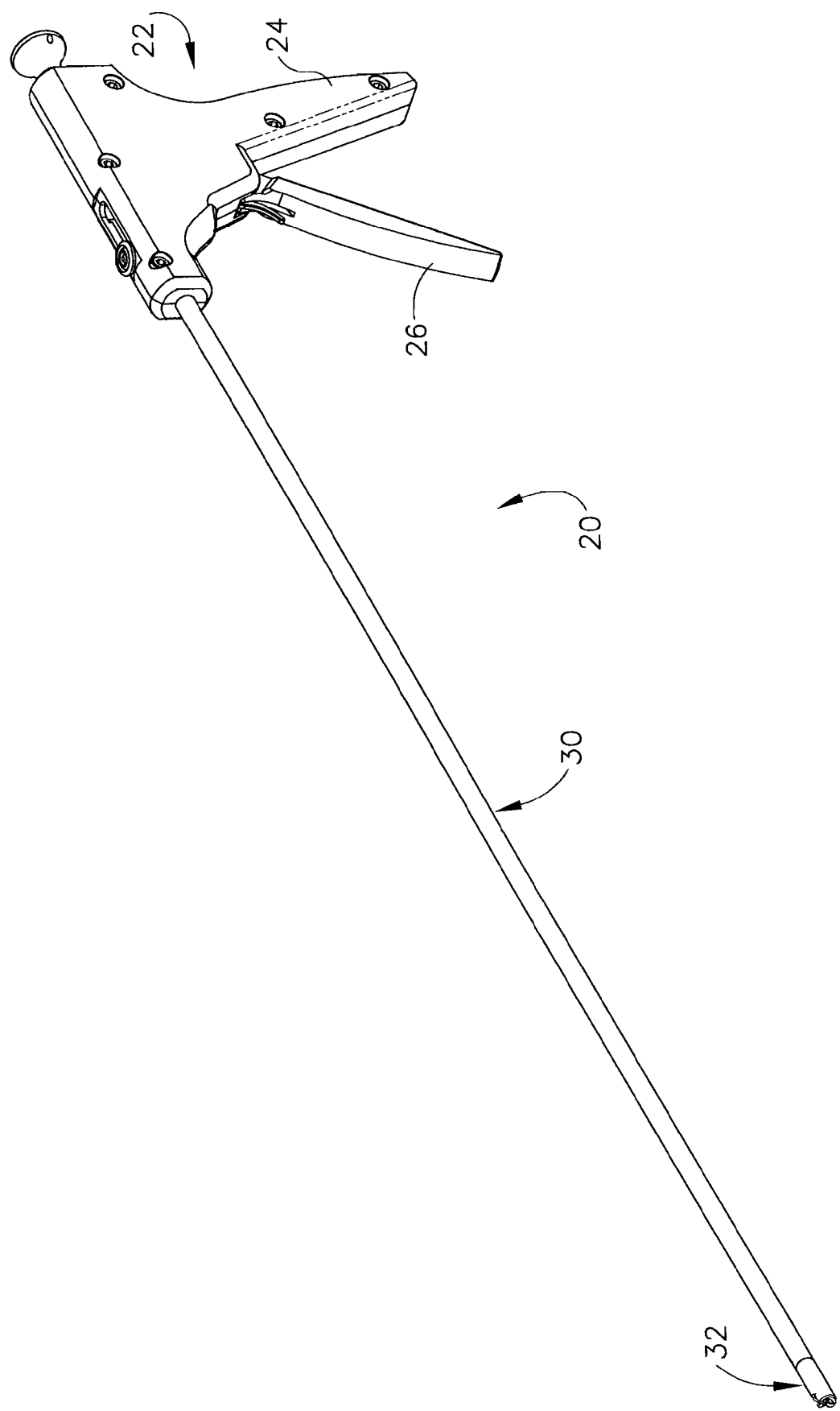
FIG. 1 is a perspective view of an exemplary suture anchor deployment device and an attached cartridge.

Referring now to the drawing figures, in which like numerals indicate like elements throughout the views, FIG. 1 illustrates a first exemplary fastener deploying device 20 of the present invention. As shown in FIG. 1, the fastener deploying device includes a handle 22 for manipulating the device. Handle 22 includes a pistol grip 24 and at least one actuator. The actuator includes a manually movable trigger 26. An elongated, tubular housing 30 extends distally from handle 22. Housing 30 has sufficient length (on the order of 18") to enable use within an obese patient at numerous trocar access sites. Likewise, housing 30 is sized to allow for passage through a small (3-5 mm) diameter trocar.

Figure 2:
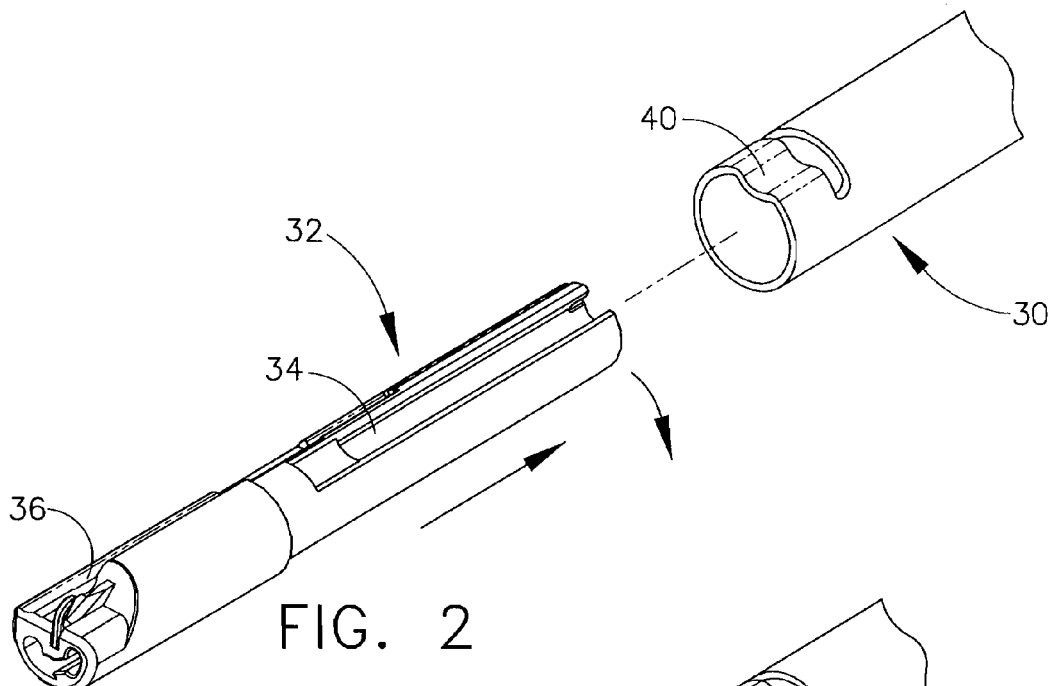
FIG. 2 is a simplified, perspective view of the cartridge coupling members and the distal end of the housing for the first coupling embodiment.
Figure 3:
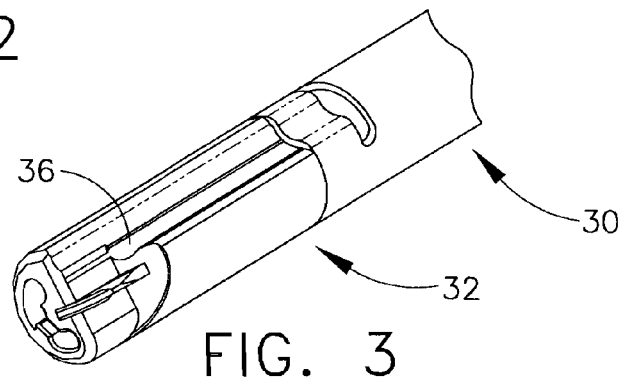
FIG. 3 is a simplified, perspective view showing the cartridge coupled to the housing for the first coupling embodiment.

Fastener deploying device 20 is designed for use with a replaceable fastener cartridge. As shown in FIG. 1, the fastener cartridge 32 is releasably attachable to the distal end of housing 30. Cartridge 32 is sized and shaped for passage through a 3-5 mm trocar when attached to the deploying device. Coupling members are located on the distal end of housing 30 and the proximal end of cartridge 32 for releasably attaching the cartridge to the deploying device. The cartridge coupling members allow for a rapid and secure removal and replacement of a cartridge. FIGS. 2 and 3 are simplified views of cartridge 32 and housing 30, depicting a first embodiment for coupling a cartridge to the distal end of the housing. In this embodiment, the coupling members include a pair of circumferentially offset, longitudinally extending open channels on the body of the cartridge. A first one of the open channels 34 extends from the proximal end of the cartridge distally to a point just beyond the proximal end of the second open channel 36. Each of the open channels 34, 36 have a smooth concave surface. A positive feature is located on the distal end of housing 30 for sliding engagement with open channels 34, 36. As shown in FIG. 2, the positive feature can comprise a radially-inward depression 40 which fits into and slides along the smooth contour of the channels 34, 36.

Figure 4A:
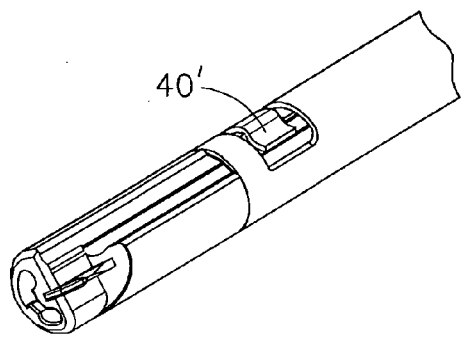
FIG. 4A is a simplified, perspective view of the cartridge and distal housing end, showing an alternative coupling member on the housing.
Figure 4B:
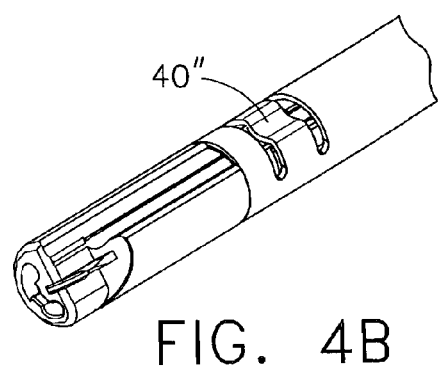
FIG. 4B is a simplified, perspective view of the cartridge and distal housing end, showing another alternative coupling member on the housing.

To connect cartridge 32 to housing 30, depression 40 is aligned with and inserted into first open channel 34. After insertion, depression 40 is slid distally along the length of the open channel until distal end of housing 30 or depression 40 comes into contact with cartridge 32. At the distal end of first open channel 34, the cartridge 32 is rotated relative to the housing 30 to cause depression 40 to jump from the distal end of the first open channel to the proximal end of the second open channel 36 as shown in FIG. 3. Depression 40 is comprised of a material that is semi-rigid to resist rotation during use, yet which will deform, deflect or otherwise temporarily move when the cartridge is rotated relative to the housing to allow the depression to jump from the first open channel to the second open channel to secure the cartridge to the housing. FIGS. 4A and 4B illustrate alternative configurations for depression 40. In each of these embodiments, the depression 40' or 40" is stamped, cut or otherwise formed into housing 30 adjacent the distal end to provide a positive feature that extends inwardly from the circumference of the housing, while maintaining at least a partial connection to the housing. To remove cartridge 32 from housing 30, the cartridge is rotated relative to the housing in the opposite direction of that rotated during attachment, to again deform depression 40 and cause the depression to jump back from the second open channel 36 to the first open channel 34. Depression 40 is then slid proximally through first open channel 34 to separate the cartridge from the housing.

Figure 5:
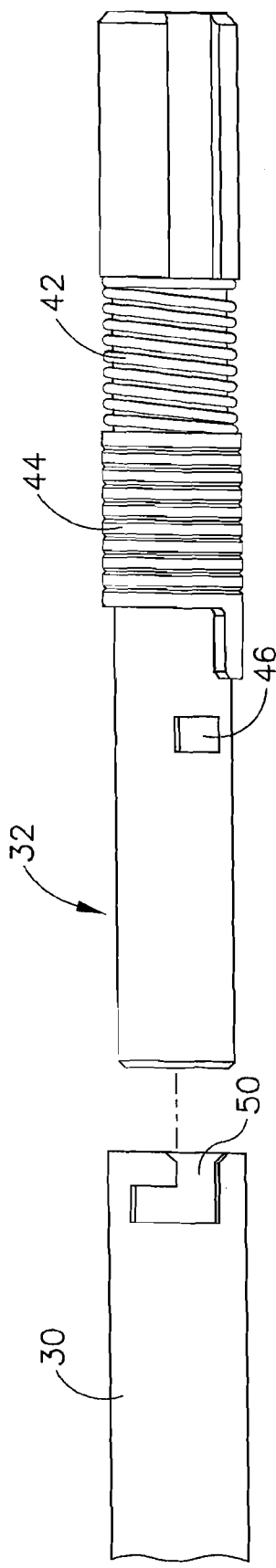
FIG. 5 is a side view of the cartridge and the distal housing end showing a second embodiment for coupling the cartridge to the housing.
Figure 6:
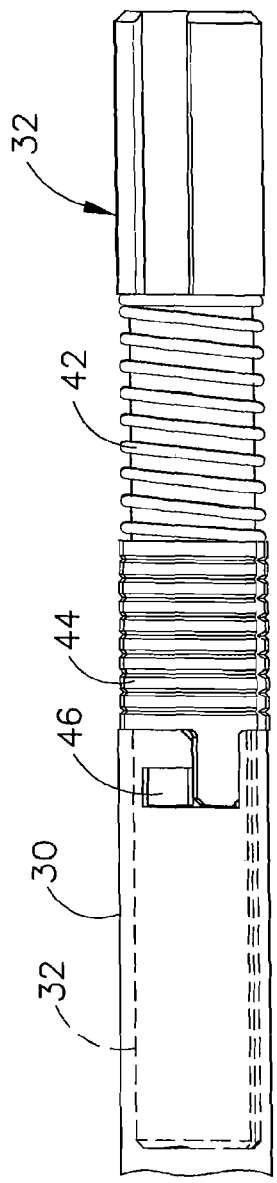
FIG. 6 is a side view similar to FIG. 5, showing the cartridge coupled to the housing in accordance with the coupling embodiment of FIG. 5.

FIGS. 5 and 6 depict an alternative embodiment for coupling a cartridge 32 to the distal end of housing 30. In this embodiment, the coupling members include a spring 42, slidable lock 44 and a raised tab 46 on cartridge 32. An "L" shaped cutout 50 is formed in the distal end of housing 30 for mating with raised tab 46. To couple cartridge 32 to housing 30, the proximal end of the cartridge is pushed into the distal end of the housing so that raised tab 46 slides down the slot of the "L" cutout 50. As cartridge 32 slides into housing 30, lock 44 slides distally up the length of the cartridge, compressing spring 42. When raised tab 46 bottoms out in the "L" cutout 50, the cartridge 32 is rotated relative to the housing 30 to slide the tab circumferentially through the lower leg of the cutout 50, and thereby lock the cartridge to the housing, as shown in FIG. 6. When tab 46 is locked into housing cutout 50, spring 42 is in a slightly compressed configuration to retain lock 44 in contact with the cutout. To remove cartridge 32 from housing 30, lock 44 is slid distally along the cartridge away from cutout 50. The cartridge is then rotated in the opposite direction relative to the housing, to allow tab 46 to slide through and out of "L" cutout 50.

Figure 11:
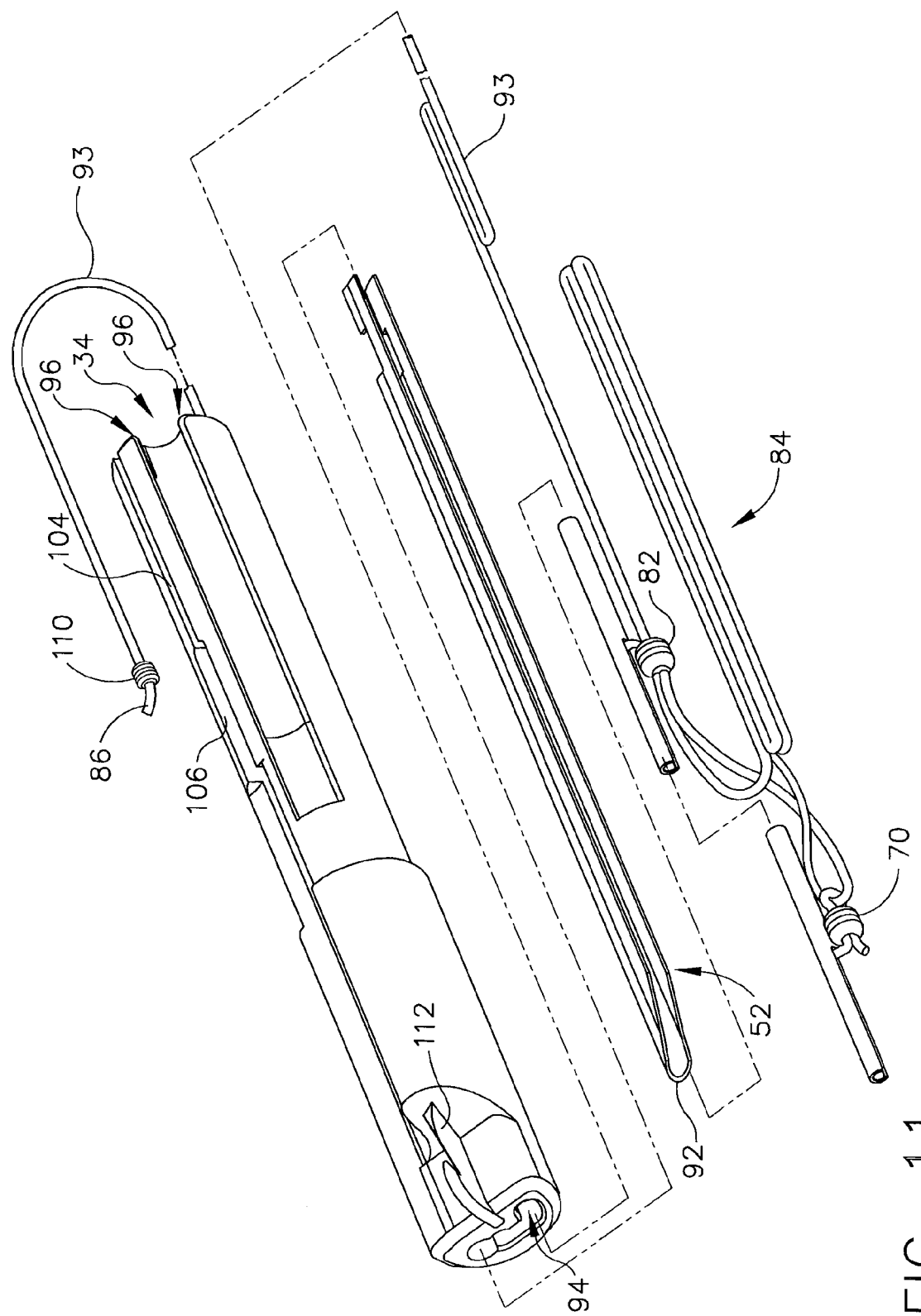
FIG. 11 is an exploded view of the cartridge shown in FIG. 7.
Figure 12:
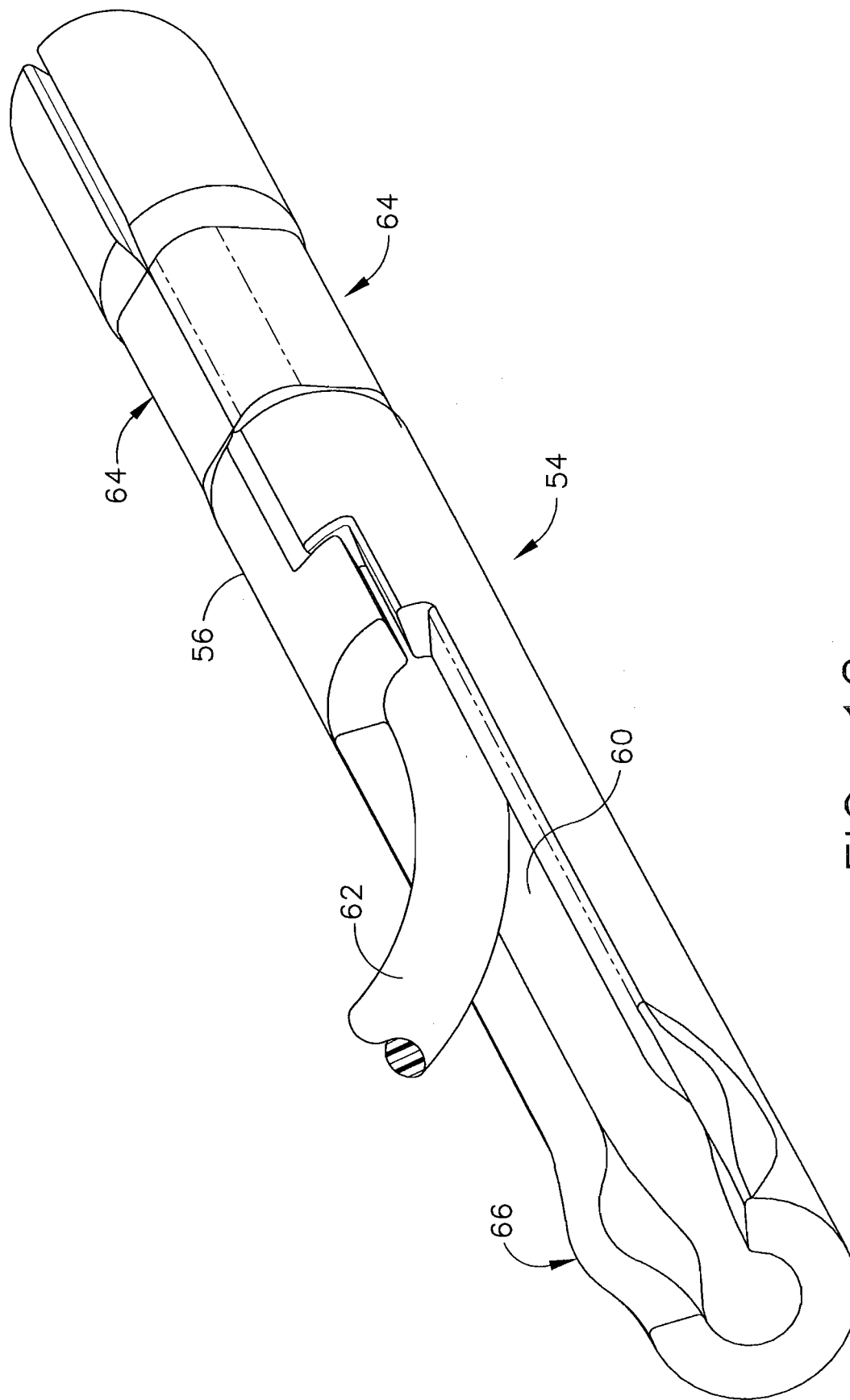
FIG. 12 is a perspective view of an exemplary T-Tag anchoring device.

Turning now to FIGS. 7 through 11, which illustrate a first embodiment for a replaceable cartridge in greater detail. As shown in the Figures, cartridge 32 contains at least one fastener and a tissue penetrating member for placing the fastener into the body. The penetrating member can be a needle 52 having a slotted lumen that extends proximally from a partially or completely sharpened tip through the length of the needle for retaining at least one fastener. Needle 52 can be made from injection molded plastic, be extruded in a plastic, metal or ceramic material, or fabricated from sheet metal in a progressive die operation. Various treatments, coatings, and mechanical alterations can be used to enhance the sharpness of the needle. In the embodiments shown and described below, the needle at least partially retains and deploys a single fastener. However, it is envisioned that needles housing more than one fastener could be developed and used in conjunction with the deploying device without departing from the scope of the invention. A fastener comprises a pair of anchoring devices connected together by a non-resilient flexible or flaccid material such as, for example, suture. Monofilament and braided sutures are exemplary materials for this fastener in that the material connecting the two preferably rigid anchoring devices is ideally comprised of a material that resists deformation when subjected to compressive loads (materials approximating a rope). Two dimensional flexible members such as ribbons can also be used. In the embodiments described herein, the anchoring devices are T-Tag type suture anchors, an example of which is shown in FIG. 12. This exemplary T-Tag anchor 54 comprises an elongated tube 56 having an opening or slot 60 extending approximately one-half the length of the tube. The remaining length of the tube is formed into a closed cylindrical shape. One end of a length of suture 62 is inserted into the closed length of the tube. The suture end is retained within the tube by crimping the midsection of the cylindrical length, as indicated by the arrows 64. The remaining length of suture 62 protrudes freely out of the slot 60. An outwardly extending projection or bulge 66 may be formed along the length of the T-Tag anchor 56. Bulge 66 creates friction between the inner diameter of the needle and the T-Tag anchor when the anchor is held within the needle lumen. This friction between the needle and the T-Tag anchor prevents the anchor from being unintentionally released from the device.

Figure 13:
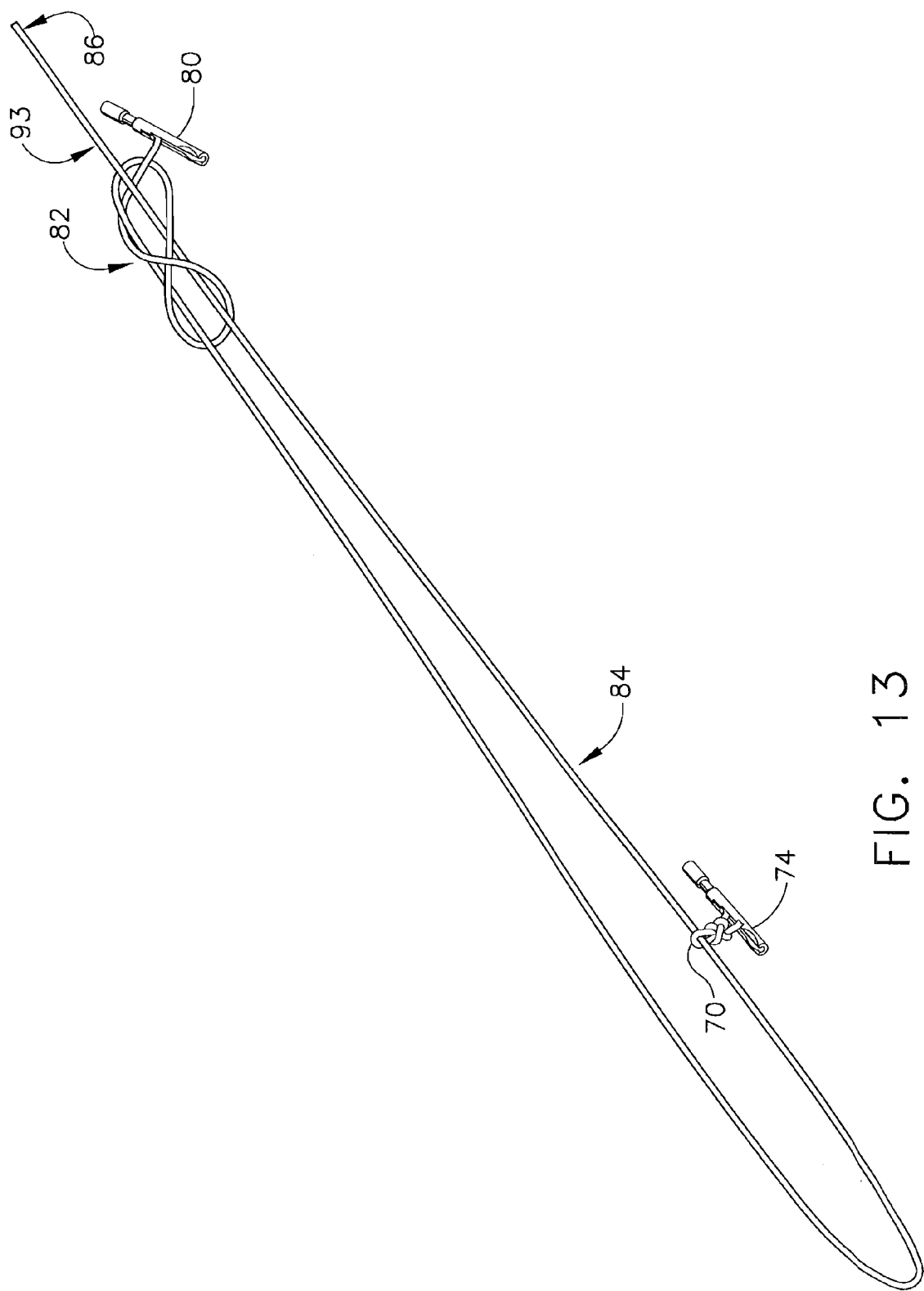
FIG. 13 is a perspective view of a slip knot formed between a pair of T-Tag anchors, showing the knot in a loosened form.
Figure 14:
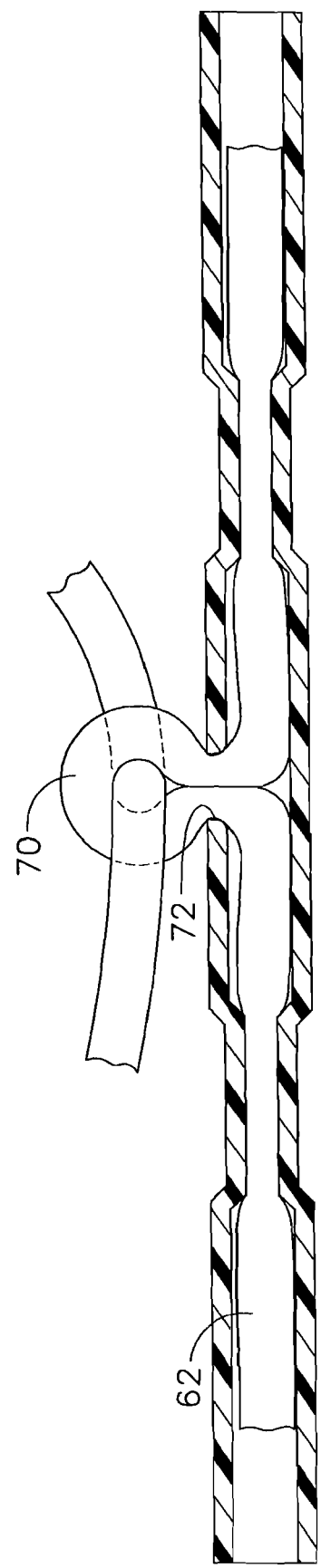
FIG. 14 is a side view of a second exemplary T-Tag anchoring device, showing a second method for forming a suture loop.

In an exemplary embodiment, the pair of T-Tag anchors are pre-tied together prior to loading the tags into the needle lumen. To tie the T-Tag anchors together, a loop or other slidable connecting member 70, such as shown in FIG. 13, is formed in the free end of suture from a first one of the T-Tag anchors 74. One skilled in the art will clearly recognize that loop 70 may be formed by a variety of different types of knots, such as, for example, a square knot, one or more ½ hitch knots, or a hangman's knot. A slidable connecting member can also be formed by altering the T-Tag anchor, as shown in FIG. 14, so that both ends of the suture length 62 are retained within the anchor, and a loop 70 of the suture protrudes from an opening 72 in the T-Tag to serve as the connecting member. In yet another embodiment, the T-Tag itself may have a hole through which suture length 84 is passed. To connect the anchor pair, a length of suture 84, attached at one end within a second T-Tag anchor 80, is passed through the suture loop 70 of the first T-Tag anchor 74 to allow the first T-Tag anchor to slide relative to the second T-Tag anchor along the length of the suture. After first T-Tag anchor 74 is slidingly connected to the suture length 84, a knot is formed in the suture. The suture knot serves to pull together and lock the T-Tag anchors when the anchors are under load following deployment. FIG. 13 shows a one-way slip knot 82 formed within the suture length 84 to draw the T-Tag anchors 74, 80 together.

Following deployment of the T-Tag anchor pair, knot 82 is tightened to set the distance between the knot and the second T-Tag anchor 80, while allowing a doubled over length of the suture 84 between the T-Tag anchors to be reduced. Once T-Tag anchors 74, 80 are deployed and fixed into the tissue, pulling on the loose end 86 (or any section of suture 93 proximal to second T-Tag anchor 80) of suture length 84 relative to the fixed T-Tag anchors reduces the size of the doubled suture length until it cannot be further reduced because of loop 70. As suture length 84 is reduced, the T-Tag anchors 74, 80 are drawn together. The final distance between the T-Tag anchors 74, 80 is defined by the distance from loop 70 to the first T-Tag 74, and the distance from knot 82 to the second T-Tag 80. The size of loop 70 may be used to adjust this overall distance. Additionally, where loop 70 is formed by tying a knot in the T-Tag anchor suture, suture knot 82 may be pre-tied in a length of suture before the T-Tag anchors are attached. Following formation of the slip knot 82, first T-Tag anchor 74 is attached to the suture length 84 by tying a knot to form loop 70. Second T-Tag anchor 80 is attached to an end of the suture length 84 by crimping the end within the anchor. The end of the suture may be crimped within T-Tag anchor 80 after knot 82 is tightened. The slip knot 82 shown in FIG. 13 is only one example of a suitable knot for connecting together a pair of T-Tag anchors. One skilled in the art will recognize that other types of slip knots may be tied such that one anchor is slidably attached to a doubled over portion of the slip knot, while the other anchor is secured to a tail or free end of the slip knot, to permit one-way cinching when forces seeking to loosen the knot are applied only to the anchors in the system.

After the T-Tag anchors are tied together, the anchor pair is preferably loaded into the needle lumen, such that the first "looped" T-Tag anchor 74 deploys initially, followed by the second "attached" T-Tag anchor 80, although the order may be switched. When loaded into the deployment needle, the T-Tags are stacked one against the other, and each T-Tag anchor is positioned so that the suture opening 60 is aligned with the slotted opening 88 in the needle lumen. FIGS. 15A and 15B illustrate an exemplary embodiment for a needle 52 in which the needle includes a slotted opening 88 extending normal to the axis of the needle. To load the T-Tag anchors into needle 52, the anchors are passed down the axis of the needle lumen and stacked against each other in the distal end of the lumen. Within the lumen, the T-Tag anchors are oriented such that the suture from each tag exits the tag midsection and passes normal to the axis of the anchor through the slotted opening 88. Slotted opening 88 includes sidewalls 90 which ramp up in height in a direction away from needle tip 92. Sidewalls 90 assist in concealing and retaining the T-Tags anchors within the needle lumen while providing an unencumbered exit for the suture. Other embodiments may use sidewalls 90 to provide resistance preventing anchors from being unintentionally deployed. Further features may be incorporated into sidewalls 90 to index the tags. One method to accomplish this is to reduce the distance between sidewalls 90 in specific predetermined locations or regions. When T-Tags 74, 80 are loaded into the needle lumen, loop 70 and knot 82 extend outside of the primary lumen of needle 52 through slotted opening 88. In a preferred embodiment, loop 70 and knot 82 are partially or completely contained within the slotted opening 88 between side walls 90. In such a circumstance, the needle 52 and side walls 90 pierce, cut, and or dilate the hole in the tissue allowing for smooth introduction of the needle through the tissue. By controlling the size of the cutting surface, the size of the resulting defect can be minimized. One may come to understand that by making a small portion of needle tip 92 sharp (using one or more beveled surfaces), the resulting hole is creating partly through direct injury (cutting by the tip 92) and partly through dilation (stretching of tissue around needle 52 and side walls 90. The greater the extent of the dilation (or alternatively the smaller the amount of cutting), the smaller the size of the resulting hole after the needle is removed. This is bounded by tissue tearing which will occur if the dilation is too extreme. One skilled in the art may use this knowledge to minimize the resulting tissue injury. By partially or completely concealing loop 70 and knot 82 with side walls 90, greater control of the resulting hole size and a smoother introduction are achieved.

Figure 16:
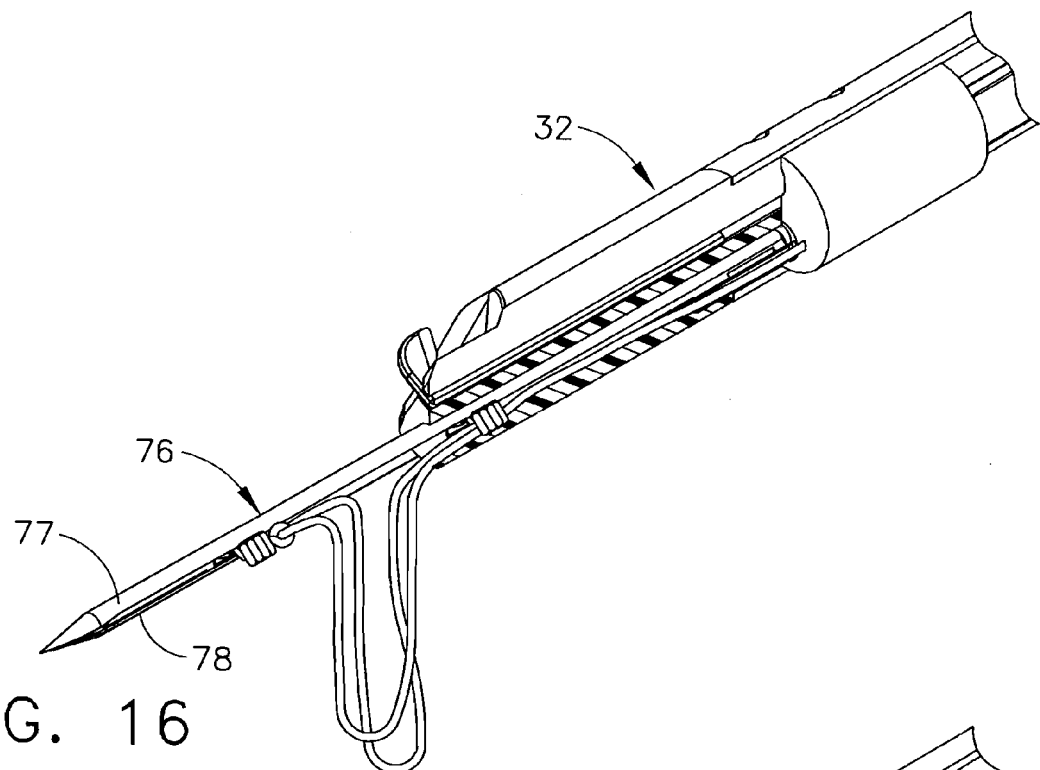
FIG. 16 is a perspective view, partially in section, showing a second needle embodiment in which the needle is extending from within the cartridge.
Figure 17:
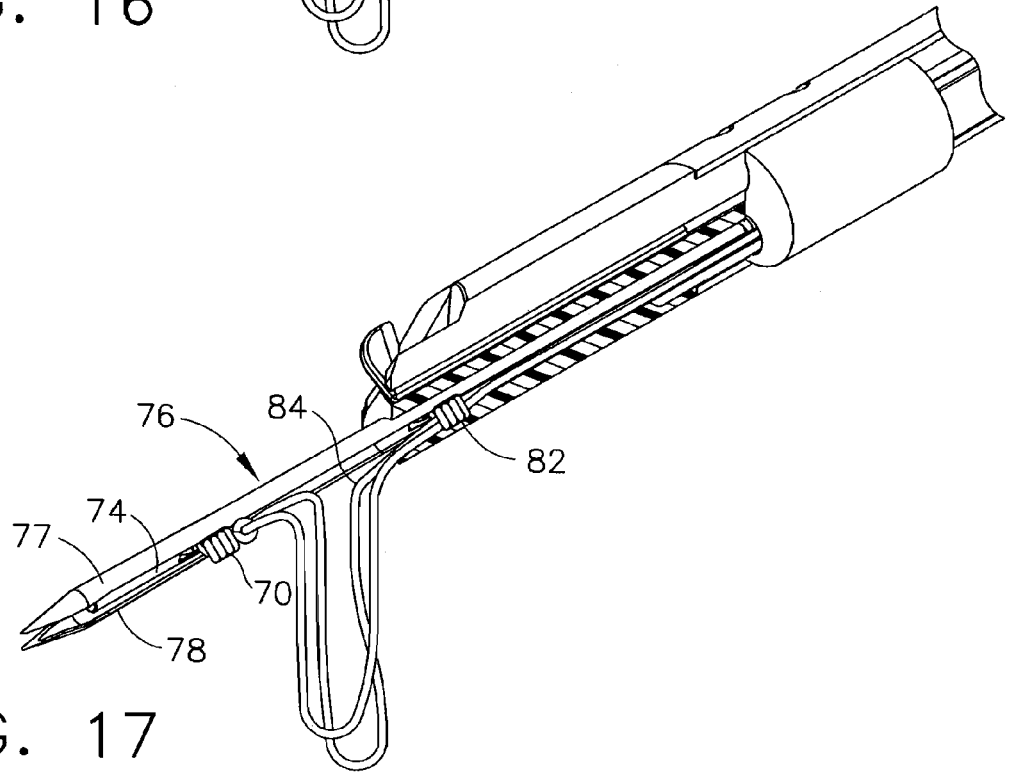
FIG. 17 is another perspective view of the needle depicted in FIG. 16, showing the needle tip opening to deploy a T-Tag anchor.
Figure 18A:
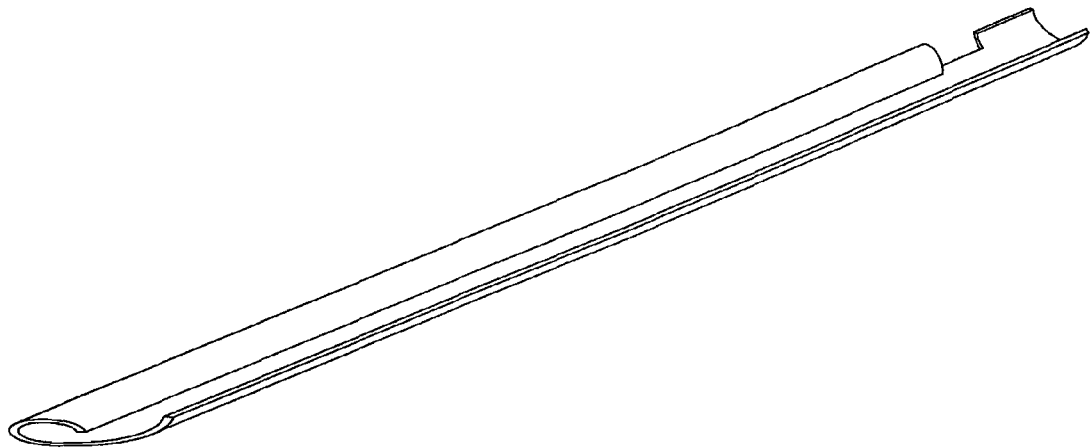
FIGS. 18A through 18C are perspective views of other alternative needle configurations.
Figure 18B:
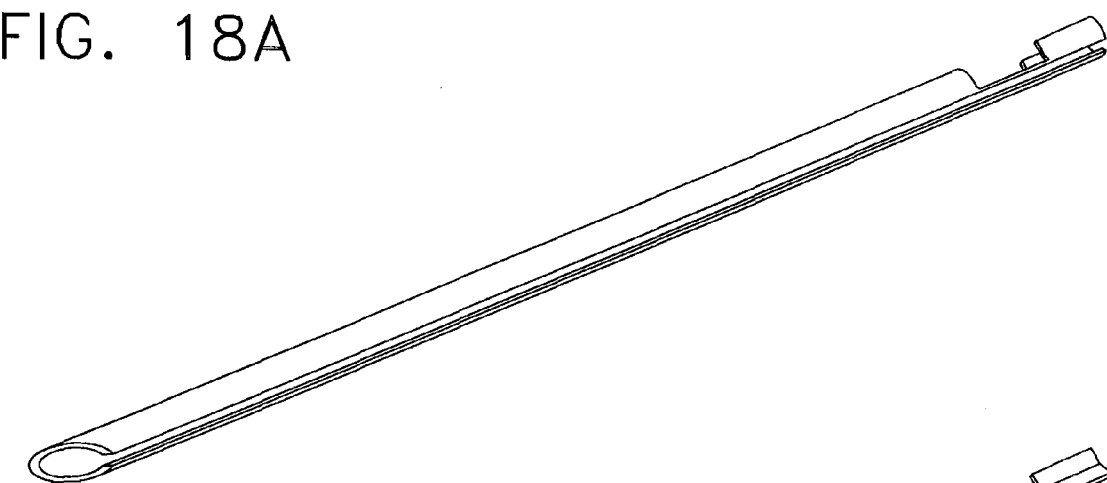
Figure 18C:
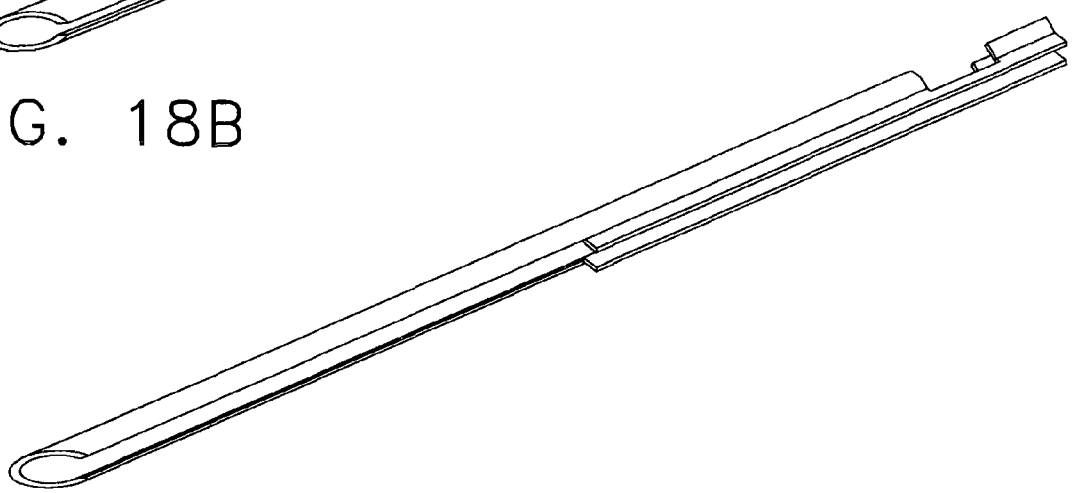

In addition to the slotted needle shown in FIGS. 15A-15B, various other types of tissue penetrating devices may be utilized to deploy T-Tag anchors in the present invention. FIGS. 16 and 17 show an alternative embodiment in which an expanding needle 76 is utilized with cartridge 32 to penetrate tissue and deploy T-Tag anchors. An advantage of such a needle is the resulting size of the hole in the tissue may be further minimized. In this embodiment, needle 76 comprises a pair of inwardly-biased, parallel, spaced arms 77, 78 which merge together into a sharpened tip at the distal end of the needle. T-Tag anchors may be loaded into the lumen formed between arms 77, 78 and held therein by the inward bias of the arms. When loading T-Tag anchors into the needle, the suture loop 70 and knot 82 attached to the T-Tags protrudes out the side opening between the arms. To penetrate tissue, the pointed, distal ends of arms 77, 78 are held together in a closed tip. Following tissue penetration the T-Tag anchors are deployed by applying a force to the proximal end of the T-Tag anchor stack to advance the T-Tags distally. As the T-Tag anchors move distally, the force of the T-Tags separates arms 77, 78 at the distal tip, as shown in FIG. 17, to allow the T-Tags to pass through the tip and outside the needle. Some additional examples of possible tissue penetrating devices are shown in FIGS. 18A-18C. Each of the devices shown in FIGS. 18A-18C includes an at least partially sharpened tip for penetrating tissue, as well as a slotted lumen. The slotted lumen in the devices at least partially retains the T-Tag anchors, while allowing the suture attached to the anchors to extend outside of the device.

Alternative fastener concepts are also compatible with the cartridge and device embodiments contained herein. One such example comprises two T-Tags connected by a non-resilient flexible material such as suture. In this and related embodiments, one strand of suture is securely connected to a tissue anchor. This strand is slidably connected to a second tissue anchor. The slidable connection to the second anchor is such that the anchor is only permitted to slide in the direction over the suture towards the first anchor. Features enabling this one way sliding feature may be contained within the suture or the second anchor. The use of barbed suture is one example that clearly meets this purpose. However, the use of one way locks in, or on the second tissue anchor itself can also achieve this purpose. Numerous one-way locking mechanisms are well understood to those skilled in the art and may be employed in this circumstance without significant changes to the cartridge or the device that deploys the tissue anchors described herein. Numerous tissue anchors are also compatible with the current inventions. Examples of tissue anchors and fasteners suitable for this task include but are not limited to the T-type anchors (mentioned above and described in more detail below), reconfigurable "basket"-type anchors (which generally comprise a number of configurable struts or legs extending between two collars or support members), and linear anchors (elongate anchors which are configured to fold or become compressed into a bowed or expanded configuration). In general, anchor characteristics are such that prior to deployment they can easily be placed into or through tissue (s), but after deployment, have an altered configuration providing at least one dimension sufficiently large to maintain the anchor in place.

Returning now to FIGS. 7 through 11, in the first embodiment of cartridge 32 the doubled length of suture 84, to which the first T-Tag 74 is sliding connected, is retained within a suture loop cavity 94 in the cartridge. The additional section of suture between knot 82 and the free suture end 86, identified by reference numeral 93 in FIG. 11, is maintained separately within suture cavity 94. The reserved lengths of suture are separately encircled upon themselves within the confines of the suture cavity. A portion of suture section 93 is extended proximally from suture cavity 94. As shown in FIG. 10, at the proximal end of cavity 94, suture section 93 spans across open channel 34 in the cartridge. Slits (or cleats), identified by reference numeral 96, are formed on opposite edges of channel 34 for holding the suture in place across the channel. From channel 34, the free end 86 of the suture is passed distally through a terminal groove 102. Terminal groove 102 has an initial, narrow diameter segment 104 that opens into a wider diameter extent 106 at a distally spaced position along the groove. The suture end 86 extends through the narrow segment 104 of the terminal groove and through an opening into the wider diameter area 106. A knot, crimp or other size enhancing member 110 is placed at the free end 86 of the suture, and the crimp placed into the larger area 106 of the terminal groove. The enlarged end 110 of the suture locks the suture in place within the terminal groove 102, and prevents the end of the suture from moving proximally through the groove when the suture is placed under load during cinching of the T-Tag anchors. When the first cartridge coupling method described above is used to attach cartridge 32 to fastener deploying device 20, terminal groove 102 lies just proximal of second groove 36

As shown in FIGS. 7 and 11, a cutting means can be provided within device 20 for severing suture. The cutting means can comprise a cutting member 112 at the distal end of cartridge 32. Preferably, the cutting member 112 is insert molded into the body of cartridge 32, but may be attached by other means. A sharpened blade 120 is spaced from the remaining body of the cutting member by a V-notch 122. Blade 120 is designed to allow suture to be wrapped around the tip of the cutting member and through notch 122. Following fastener deployment and cinching of the suture between the deployed T-Tag anchors, the remaining suture length can be looped through notch 122. A grasper may be used to assist in drawing the suture into notch 122. With the suture inside notch 122, cartridge 32 can be pulled proximally with a firm motion to tension the suture against blade 120 to sever the suture. Cutting member 112 is one example of a suture cutting means useable with the cartridge of the present invention. Other alternative devices and methods known to those skilled in the art may also be used for severing suture following cinching of the T-Tag anchors without departing from the scope of the invention.

Figure 19:
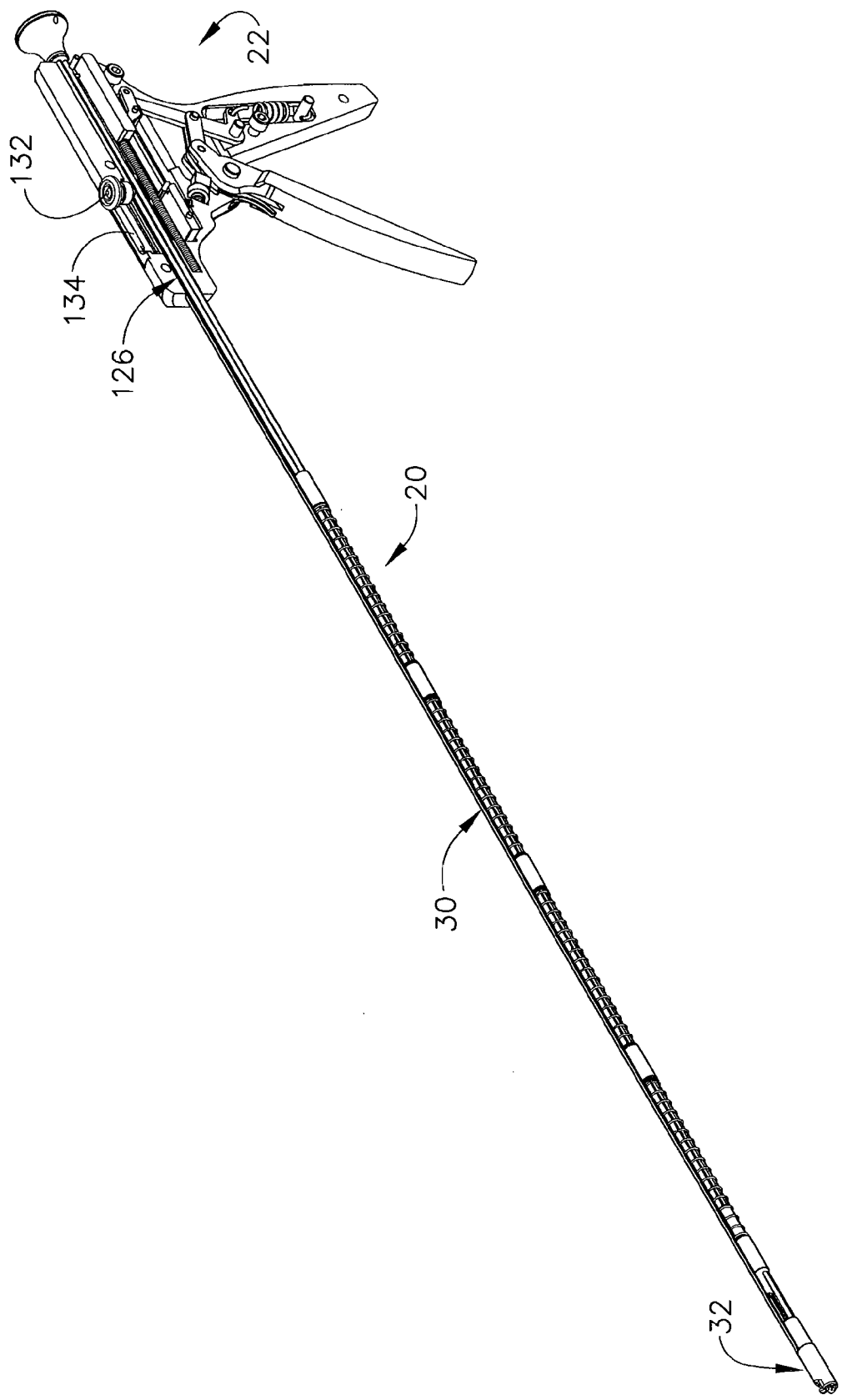
FIG. 19 is a perspective, sectional view of the deploying device and cartridge shown in FIG. 1.
Figure 20:
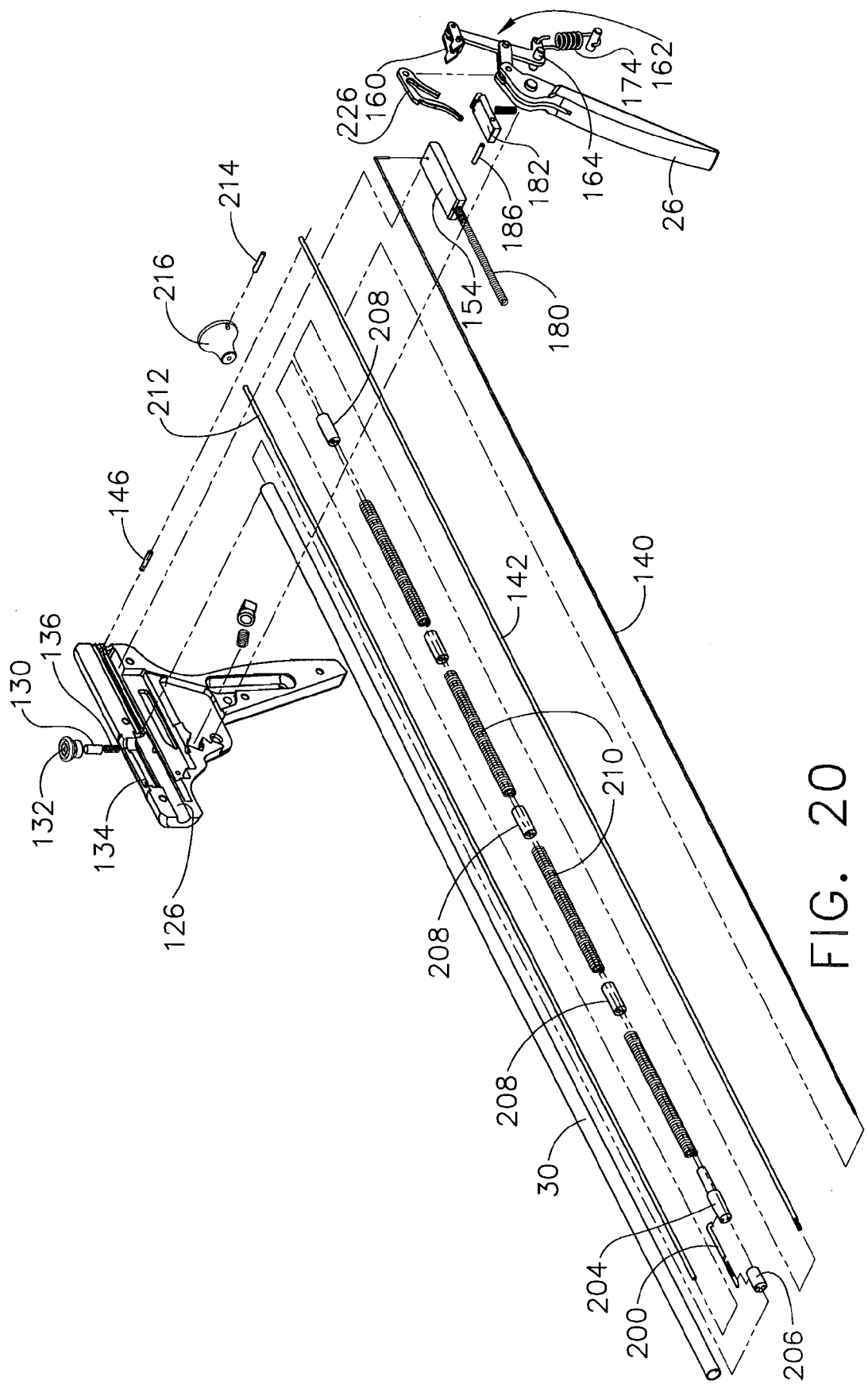
FIG. 20 is an exploded view of the deploying device shown in FIG. 19.

Turning now to FIGS. 19 and 20, which depict a first exemplary fastener deploying device 20 in greater detail. As mentioned above, deploying device 20 includes a handle 22 and an elongated, tubular housing 30 which extends outwardly in a distal direction from the handle. Handle 22 preferably comprises a molded, plastic casing having a channel 126 formed therein through which housing 30 can slide relative to the handle. Housing 30 includes an open distal end for coupling with cartridge 32. As described above, the distal end of housing 30 can include either a positive feature 40, an "L" shaped cutout 50, or other related attachment means for coupling a cartridge to the housing. A post 130, having an attached button 132, extends perpendicular to the axis of the housing, and through the handle case, for manually retracting and/or advancing the housing. Post 130 rides within a track 134 formed into the handle casing. To retract (or advance) housing 30, button 132 is pushed in a downward direction to disengage post 130 from one of two recessed areas at the ends of track 134. Once disengaged, the post 130 can be manually slid through the track 134 to the recessed area at the opposite end of the track. At the recessed area, post 130 and button 132 pop upwardly under the force of spring 136. The track recess locks the post 130 and, correspondingly, the attached housing 30 in position and prevents further movement. By depressing button 132, post 130 can be slid back and forth through track 134 to advance and retract the housing. At each end of the track, the spring-loaded post pops upwardly into a recess to lock the post and housing in position.

Figure 21:
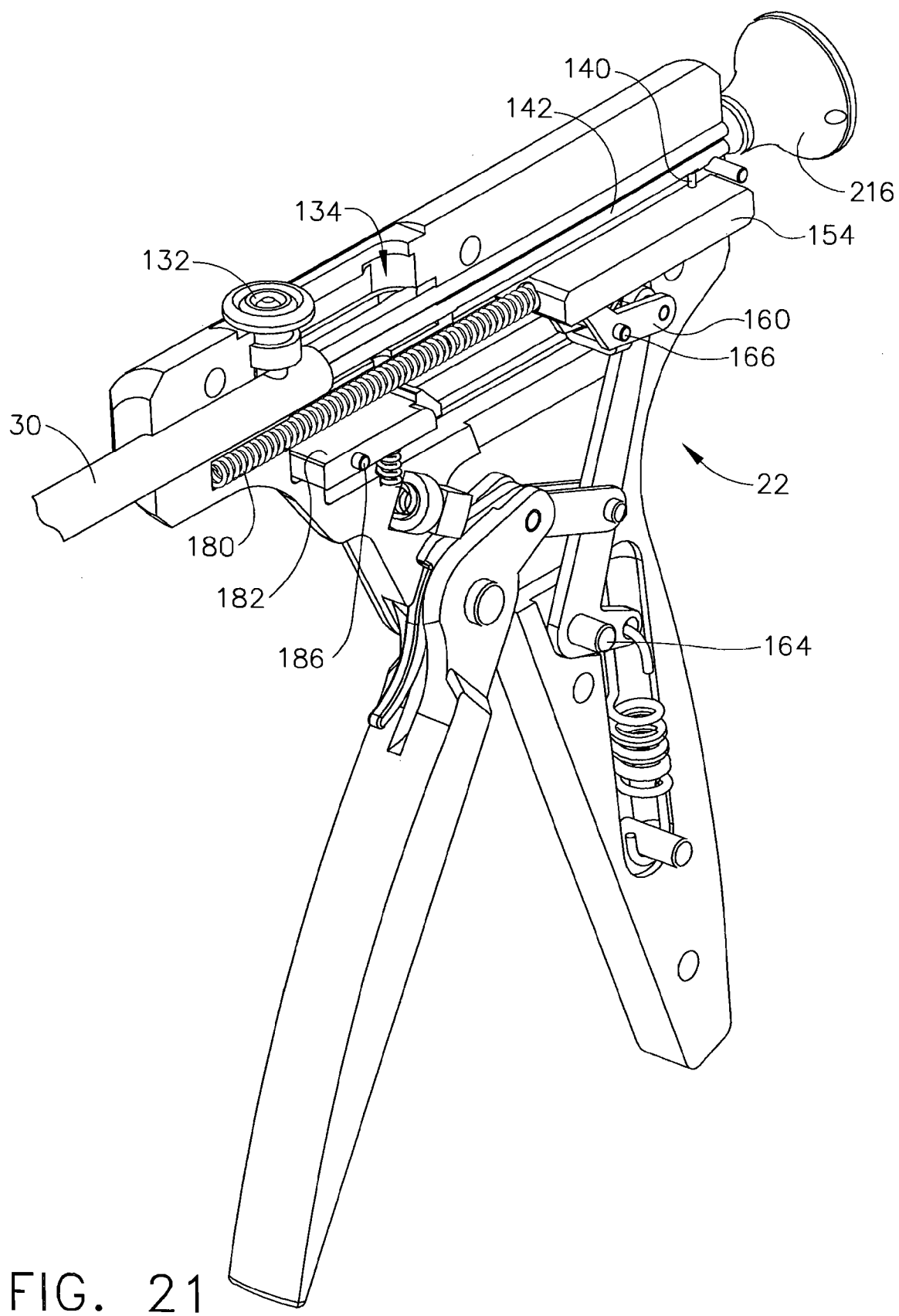
FIG. 21 is a perspective, view of the deploying device handle, shown with the handle casing partially removed looking in the proximal direction, showing the housing in its distal position and the actuating mechanism in an initial position.
Figure 22:
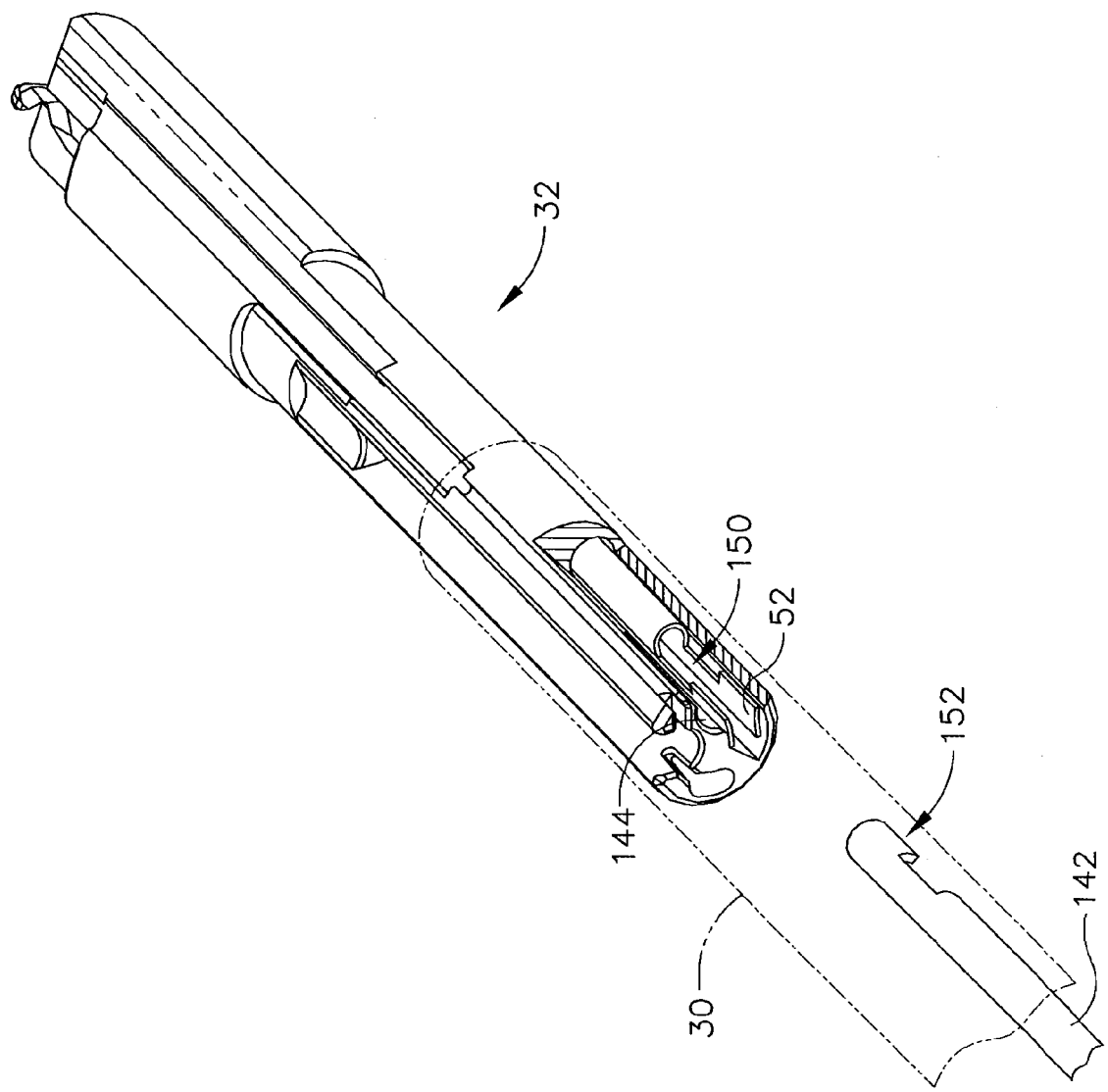
FIG. 22 is a partial cutaway perspective view of the cartridge, taken from the proximal end, showing the attachment members on the needle and push rod sheath.

As shown in greater detail in FIGS. 20 and 21, handle 22 includes an actuating mechanism for expelling T-Tag anchors from the needle of an attached cartridge. The actuating mechanism includes an elongated push rod 140 which extends longitudinally from handle 22 through housing 30. Push rod 140 is enclosed within a cylindrical, longitudinally extending push rod sheath 142. A pin 146 passes through the proximal end of push rod sheath 142 for connecting the sheath to the handle casing. The distal end of push rod sheath 142 extends to the distal end of housing 30 and is designed for mating with the proximal end of needle 52 when a cartridge is attached to the housing. FIG. 22 shows the proximal end of the cartridge 32 in greater detail. As shown in this figure, needle 52 slides within a tubular cavity 144 through the interior of cartridge 32. Cavity 144 is open at both the proximal and distal ends of the cartridge. The proximal end of needle 52 includes a notch 150 which is adjacent to the proximal end of needle cavity 144, when the needle is fully enclosed within the cartridge. When a cartridge 32 is mated to housing 30, the proximal end of the cartridge is inserted into the distal end of the housing. As the cartridge is inserted into the housing, a tab 152 on the proximal end of push rod sheath 142 is inserted into the top portion of needle cavity 144. When the cartridge is rotated relative to the housing to lock the cartridge to the housing, the distal end of push rod sheath 142 is rotated down from the top of needle cavity 144 to place tab 152 into mating contact with needle notch 150. As push rod sheath 142 is rotated into contact with needle 52, tab 152 is engaged into position within notch 150 to connect the push rod sheath to the needle. With push rod sheath 142 mated to needle 52, the distal end of push rod 140 is axially aligned with the proximal end of the T-Tag anchor stack in the needle lumen for advancing and expelling the anchors from the needle. As mentioned above, needle cavity 144 is open at the distal end of cartridge 32 to allow the needle to be exposed distally from the cartridge.

Figure 23:
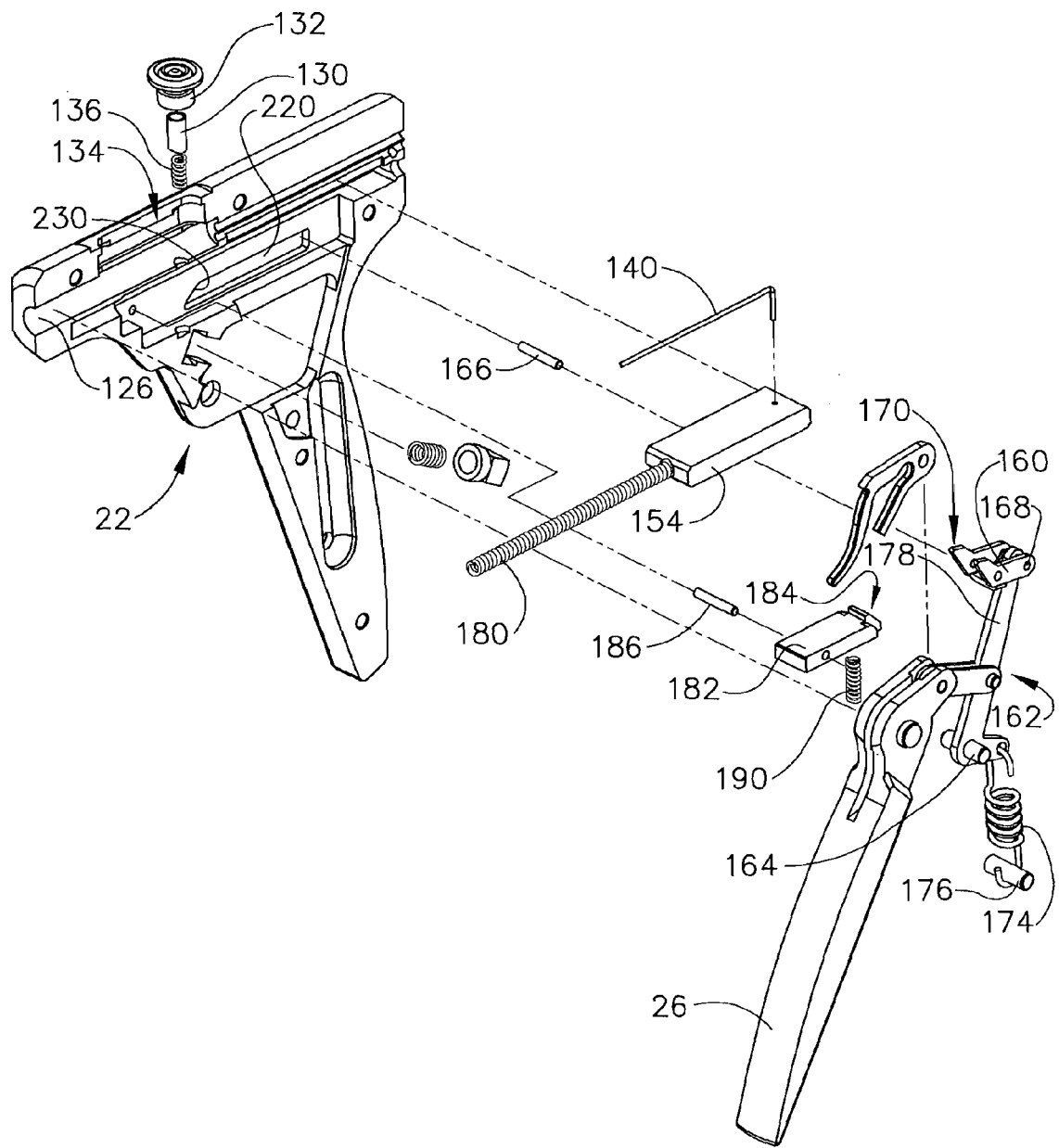
FIG. 23 is a perspective, exploded view of the actuating mechanism in the handle.
Figure 24:
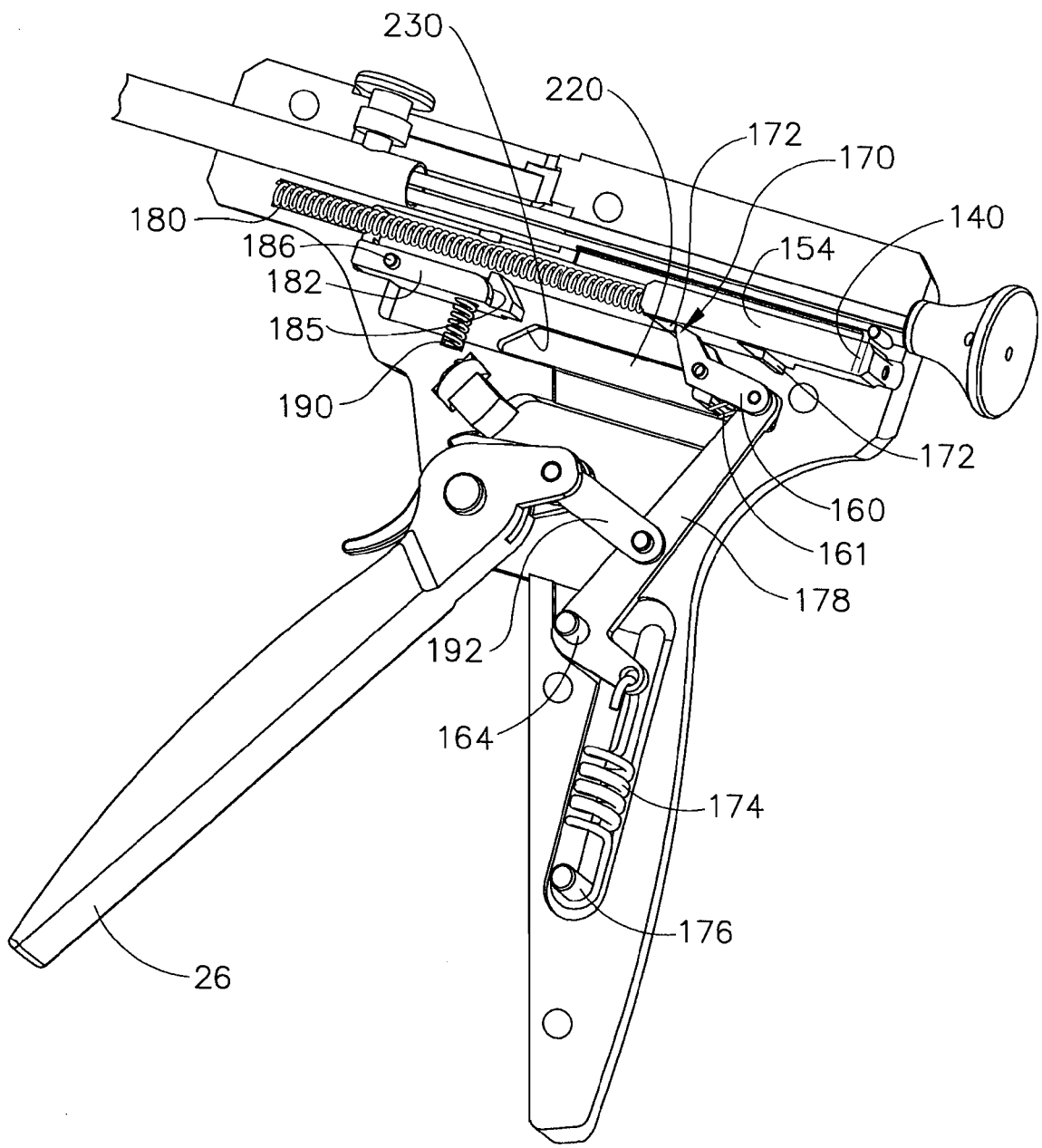
FIG. 24 is a second, perspective, sectional view of the deploying device handle, showing the handle angled downwardly on a side.

As shown in FIG. 23, the proximal end of push rod 140 is mounted within a push rod driver 154 inside handle 22. Push rod driver 154 advances the push rod 140 distally a predetermined distance when activated through trigger 26. A push rod advancing mechanism extends between trigger 26 and the push rod driver 154 for transferring a manual squeezing motion on the trigger into forward propulsion of the push rod 140 in the direction of the T-Tag anchors. The push rod advancing mechanism includes a drive pawl 160 that is connected through a linkage 162 to trigger 26. Drive pawl 160 pivots about a first pin 168 in the linkage. A catch 170 is located at the distal end of the drive pawl 160. A torsion spring 161 is located about first pin 168 and biases catch 170 to be in contact with push rod driver 154. A second pin 166 extends between two side walls of the drive pawl 160. Push rod driver 154 includes a plurality of downwardly directed teeth 172, shown in FIG. 24. Push rod driver teeth 172 are positioned slightly distal to drive pawl catch 170 when the trigger 26 is in an open position so that the upwardly extending catch engages the teeth one at a time to advance the push rod distally. A drive pawl spring 174 is connected between a pin 176 in pistol grip 24 and a lever 178 within the linkage 162 to bias the drive pawl 160 in the proximal direction. A bar 192 is connected by a pair of pins between lever 178 and trigger 26, to transfer the squeezing motion on the trigger into pivoting motion within the linkage 162. As shown in FIGS. 23 and 24, a push rod driver spring 180 is located distal of push rod driver 154 for biasing the driver proximally into contact with the drive pawl 160. An anti-backup pawl 182 is located distal of drive pawl 160 to engage push rod driver teeth 172 after each forward, T-Tag deploying advance, in order to prevent the push rod driver from retracting within the housing 30 prior to the complete deployment of the anchor. Anti-backup pawl 182 includes a catch 184 having a proximal ramped side and a distal cut-off side. Anti-backup pawl catch 184 is sized to allow the catch to engage and securely hold a tooth 172 on push rod driver 154 along the surface of the cut-off side. The anti-backup pawl 182 pivots about a pin 186 to move in and out of contact with push rod driver 154. An anti-backup pawl spring 190 biases the anti-backup pawl 182 in an upward direction into engagement with the push rod driver 154, but not so far as to come into contact with push rod driver spring 180 when the anti-backup pawl 182 is not in contact with push rod driver 154.

As shown in FIGS. 19 and 20, a suture cinching assembly is enclosed within housing 30 for positioning the deployed T-Tag anchors adjacent to one another within the tissue. As shown in greater detail in FIG. 25, the suture cinching assembly includes a suture grasping member 200 extending axially within housing 30. The distal end of suture grasping member 200 is curved and bent back proximally to form a hook 202 having an angled distal tip. A cylindrical, slotted guide member 206 is located inside housing 30 adjacent the distal end and is fixed in place within housing 30. Suture grasping member 200 passes through the slot in guide member 206 to direct the movement of the distal end of suture grasping member 200 into the proximal end of an attached cartridge. The proximal end of suture grasping member 200 is connected to a cylindrically-shaped shuttle 204. Suture grasping member 200 is bent at an angle to the axis of the member in order to engage an opening in the shuttle 204. Both guide member 206 and shuttle 204 include a through hole to enable the push rod sheath 142 (and enclosed push rod) to pass there through on route to the distal end of housing 30.

A cinching spring 210 extends proximally from shuttle 204 substantially through the length of housing 30. Cinching spring 210 is compressible for retracting suture grasping member 200 and shuttle 204 proximally into the housing. As shown in FIGS. 19 and 20, cinching spring 210 comprises a plurality of spring segments joined together by cylindrical connecting pieces 208. Each of the connecting pieces 208 has a pair of through holes to allow the pushrod sheath 142 and a pull rod 212 to extend through the inside of the cinching spring. Pull rod 212 is connected at a distal end to shuttle 204. Pull rod 212 extends from shuttle 204 through cinching spring 210 (in housing 30) and handle channel 126. The proximal end of pull rod 212 is attached by a pin 214 to a knob 216 on the outside of handle 22. Knob 216 provides a mechanism for manually retracting shuttle 204 and, in turn, suture grasping member 200 during suture cinching. As an alternative to pull rod 212 and knob 216, other devices which would be known to those skilled in the art, may be used for retracting suture grasping member 200 proximally within the housing. These alternative devices can include levers, strings, and pulleys, among others.

Figure 26:
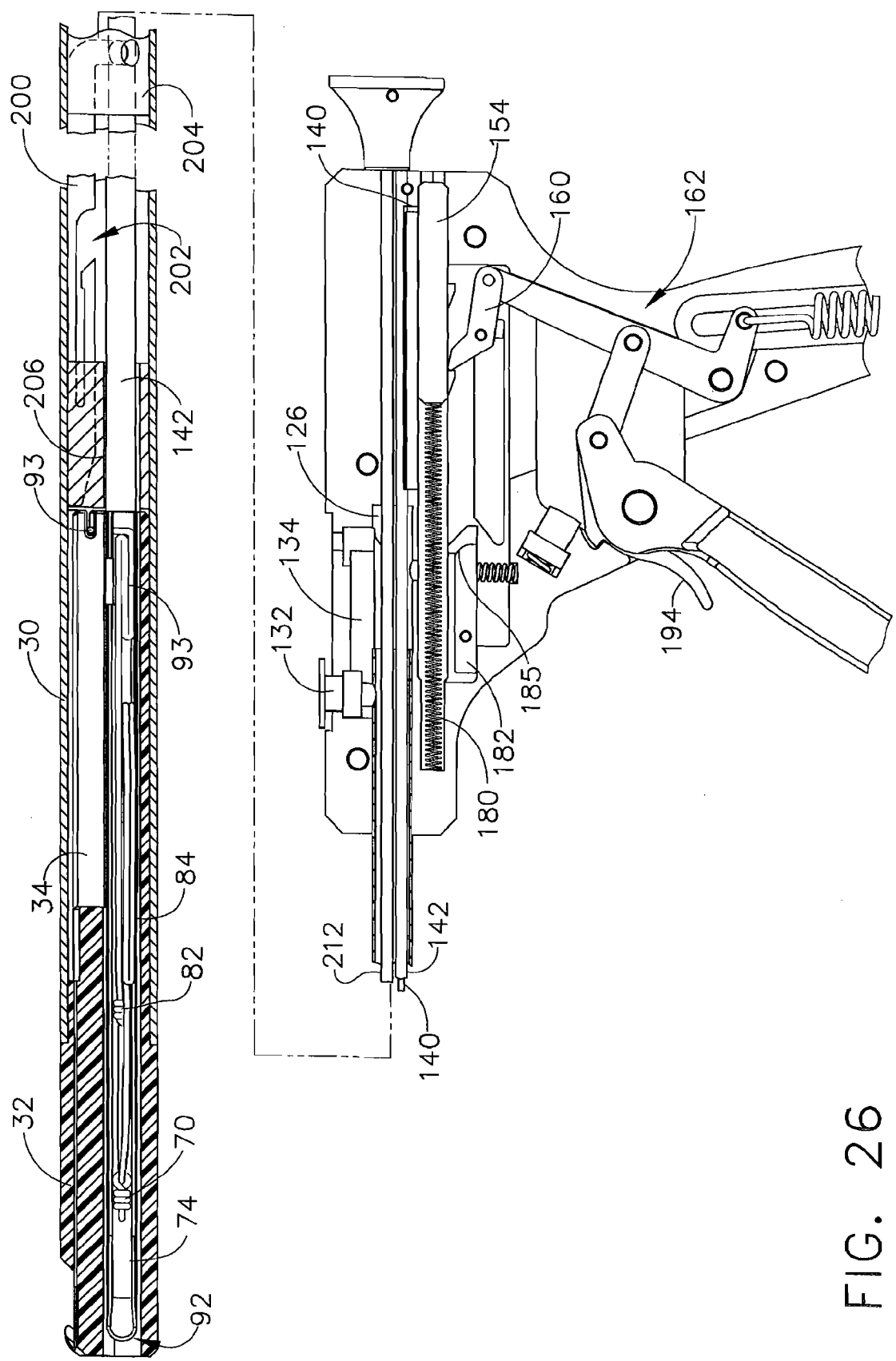
FIG. 26 is a sectional view of the deploying device and cartridge in an initial, mated condition prior to fastener deployment.
Figure 27:
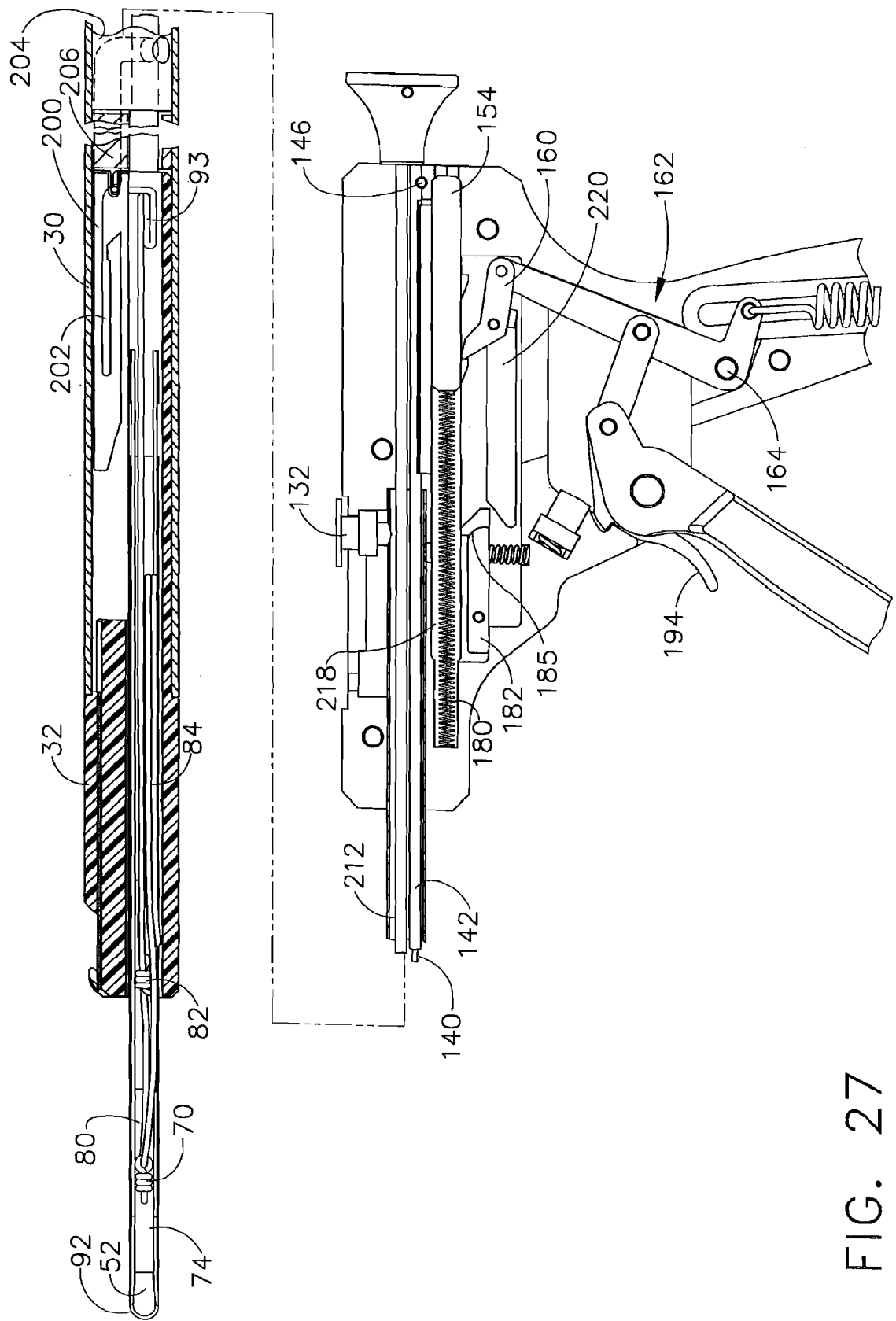
FIG. 27 is a sectional view of the deploying device and cartridge, showing the cartridge and housing retracted to expose the needle from the cartridge.

FIG. 26 depicts deploying device 20 and an attached cartridge 32 prior to deployment of a fastener. To deploy the first T-Tag anchor from needle 52, button 132 on handle 22 is depressed and slid proximally through track 134 to retract the housing and attached cartridge. As housing 30 is retracted, the housing slides through channel 126 in the handle. The attached cartridge 32 retracts along with housing 30, exposing needle 52 from the distal end of the cartridge, as shown in FIG. 27. Needle 52 remains stationary as the cartridge 32 is retracted, due to the connection between the needle and the stationary push rod sheath 142. As cartridge 32 is retracted, suture grasping member 200 remains fixed in position within housing 30, with the result that the grasping member is advanced into open channel 34 of the cartridge as the cartridge retracts around the grasping member. As cartridge 32 retracts about suture grasping member 200, suture segment 93 that spans across charnel 34 is drawn under and into hook 202 of the suture grasping member by the angled tip of the member. In addition, as cartridge 32 retracts, push rod 140 (which remains stationary) is advanced from the distal end of housing 30, through the mating connection between push rod sheath 142 and needle 52, and into the proximal end of the needle lumen. Rounded, tapered or otherwise angled edges on the distal end of push rod 140 may be used to aid in the entrance of the push rod into the lumen of needle 52.

Figure 28:
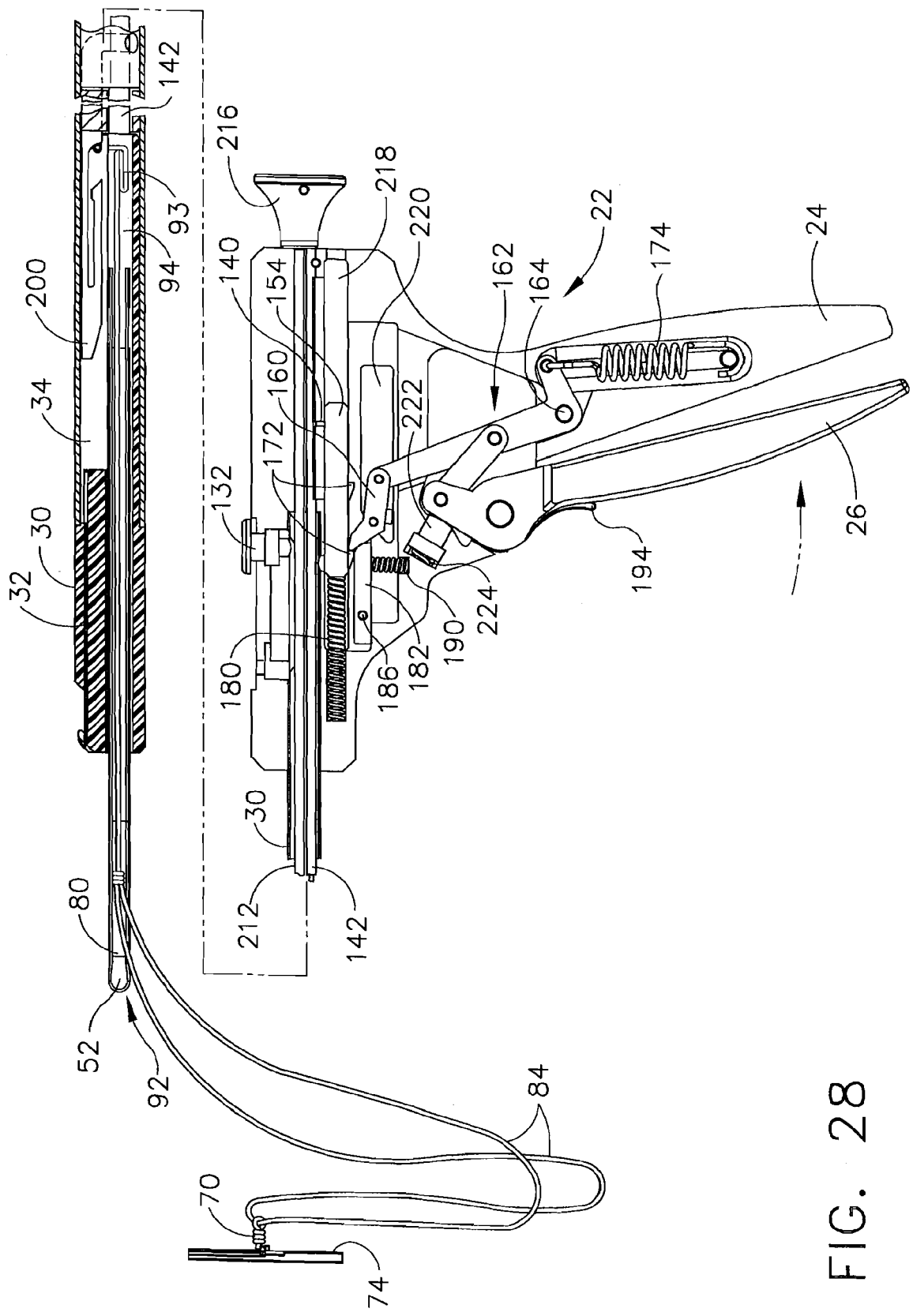
FIG. 28 is a sectional view of the deploying device and cartridge showing a first T-Tag anchor ejected from the needle.

With needle 52 exposed at the distal end of the cartridge, handle 22 is manually pushed forward to penetrate a targeted tissue area with the needle tip 92. With needle 52 inside and through the tissue, trigger 26 is manually squeezed in the direction of pistol grip 24. A trigger safety 194 is located near the top of trigger 26. Trigger safety 194 is manually squeezed prior to and then along with trigger 26 in order for the trigger to rotate. As trigger 26 is rotated towards pistol grip 24, linkage 162 is pivoted about pin 164 to push drive pawl 160 in the distal direction. Initially, drive pawl 160 is in a proximal-most position within a drive pawl track 220 formed in the handle casing. Drive pawl 160 is engaged with the distal tooth on push rod driver 154, which is in turn in a proximal-most position at the end of a pushrod driver track 218. As trigger 26 is squeezed, as shown in FIG. 28, drive pawl 160 is pushed distally along track 220. As drive pawl 160 is pushed distally, the drive pawl applies pressure against the distal push rod driver tooth to likewise push the driver distally through track 218. To advance push rod driver 154, sufficient force must be applied through trigger 26 to overcome the counterforce of push rod biasing spring 180. As described above, the proximal end of push rod 140 is connected to the push rod driver 154. Therefore, as push rod driver 154 is advanced distally by drive pawl 160, push rod 140 is likewise advanced distally within the lumen of needle 52. As push rod 140 advances, the push rod comes into contact with the proximal end of the T-Tag anchor stack within the needle lumen. As push rod 140 is advanced further, the contact force of the push rod 140 against the T-Tag anchor stack slides the T-Tag anchor stack towards the open distal end of the needle. The force of the advancing push rod 140 expels the distal-most T-Tag anchor in the stack (i.e. first T-Tag anchor 74) from the needle and into or through the tissue. As the T-Tag anchor is deployed, the suture knot or loop 70 connected to the T-Tag is passed out of the needle through slot 88. Note that the total travel of the push rod is greater than the length of one T-Tag with the first squeeze of the trigger as shown in FIGS. 27 and 28.

Figure 29:
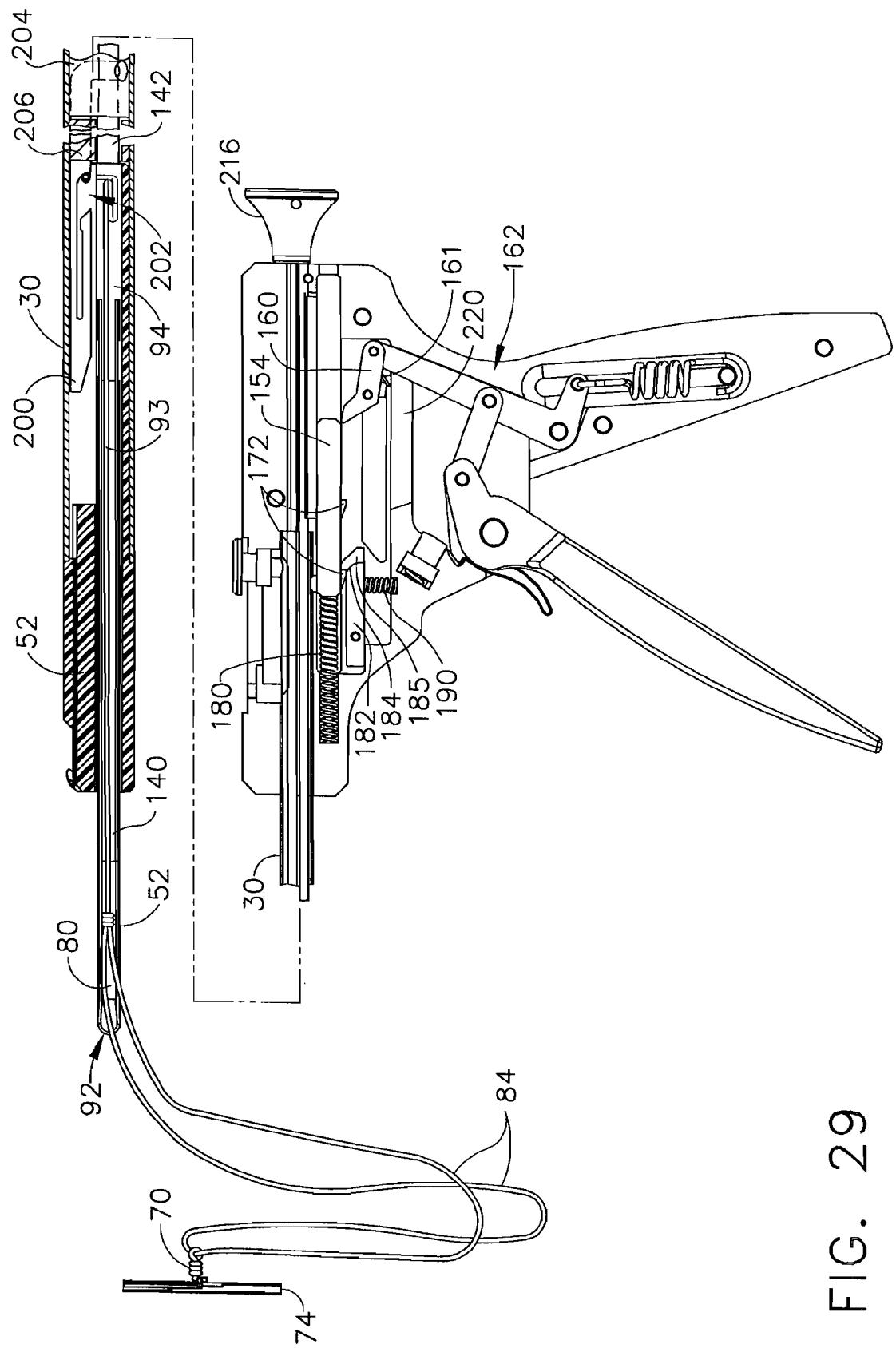
FIG. 29 is a sectional view of the deploying device and cartridge, showing the trigger released prior to deployment of the second T-Tag anchor.

As push rod 140 is pushing the first T-Tag anchor 74 out of needle 52, drive pawl 160 pushes the distal tooth of push rod driver 154 past the catch of anti-backup pawl 182. The ramped proximal side of anti-backup pawl catch 184 enables the anti-backup pawl to be deflected downwardly about pin 186, by the angled face of the distal push rod driver tooth, in order to allow the distal tooth 172 to pass over the anti-backup pawl catch 184. After the distal tooth 172 has advanced over the ramped face of the anti-backup pawl catch 184, the anti-backup pawl 182 springs back into contact with the lower face of the push rod driver 154 due to the resilient force of spring 190, as shown in FIG. 29. After the first T-Tag anchor is deployed from needle 52, and anti-backup pawl 182 engages the first, distal tooth of push rod driver 154, tactile feedback is provided to the surgeon that a T-Tag has been deployed. This tactile feedback can be provided in a number of different ways. In the embodiment shown in FIGS. 28 and 29, the feedback is provided through a spring loaded button 222 within handle 22. Button 222 is located within a niche formed in the handle casing. Button 222 is positioned within the niche such that an end of the button protrudes out into the path of the pivoting trigger 26. As trigger 26 nears the end of its stroke, an edge of the trigger contacts the end of button 222, as shown in FIG. 28. Continuing to rotate trigger 26 after contact with button 222 produces additional manual resistance, as the trigger must work against the counterforce of feedback button spring 224. Preferably, button spring 224 has a high compression force so that a noticeable increase in manual squeezing pressure is necessary to compress the spring. The counterforce resistance of button spring 224 is felt by the user through trigger 26, to provide the end of stroke indication to the user. In an alternative embodiment, a segment of the trigger comes into contact with a pin that when in an interference position does not allow the trigger to advance past the point where it comes into contact with the spring loaded button 222. This pin is manually movable however and can be moved into a non-interference position allowing the trigger to be advanced further if desired.

Upon receiving the tactile feedback, or otherwise upon completion of the trigger stroke, the manual pressure on trigger 26 is released, allowing the trigger to pivot back to its initial position under the force of drive pawl spring 174 in the trigger linkage 162. As trigger 26 rotates away from pistol grip 24, drive pawl 160 is driven back proximally along the lower edge of push rod driver 154 to the proximal end of track 220. The distal angled face of the second push rod driver tooth 172 enables the drive pawl to ride over and past the second tooth to the proximal end of track 220. As drive pawl 160 moves proximally, the contact between the distal push rod driver tooth 172 and the anti-backup pawl catch 184 prevents the push rod 140 from moving proximally within the needle lumen and the push rod remains in contact with the proximal T-Tag anchor 80 as shown in FIG. 29.

Figure 30:
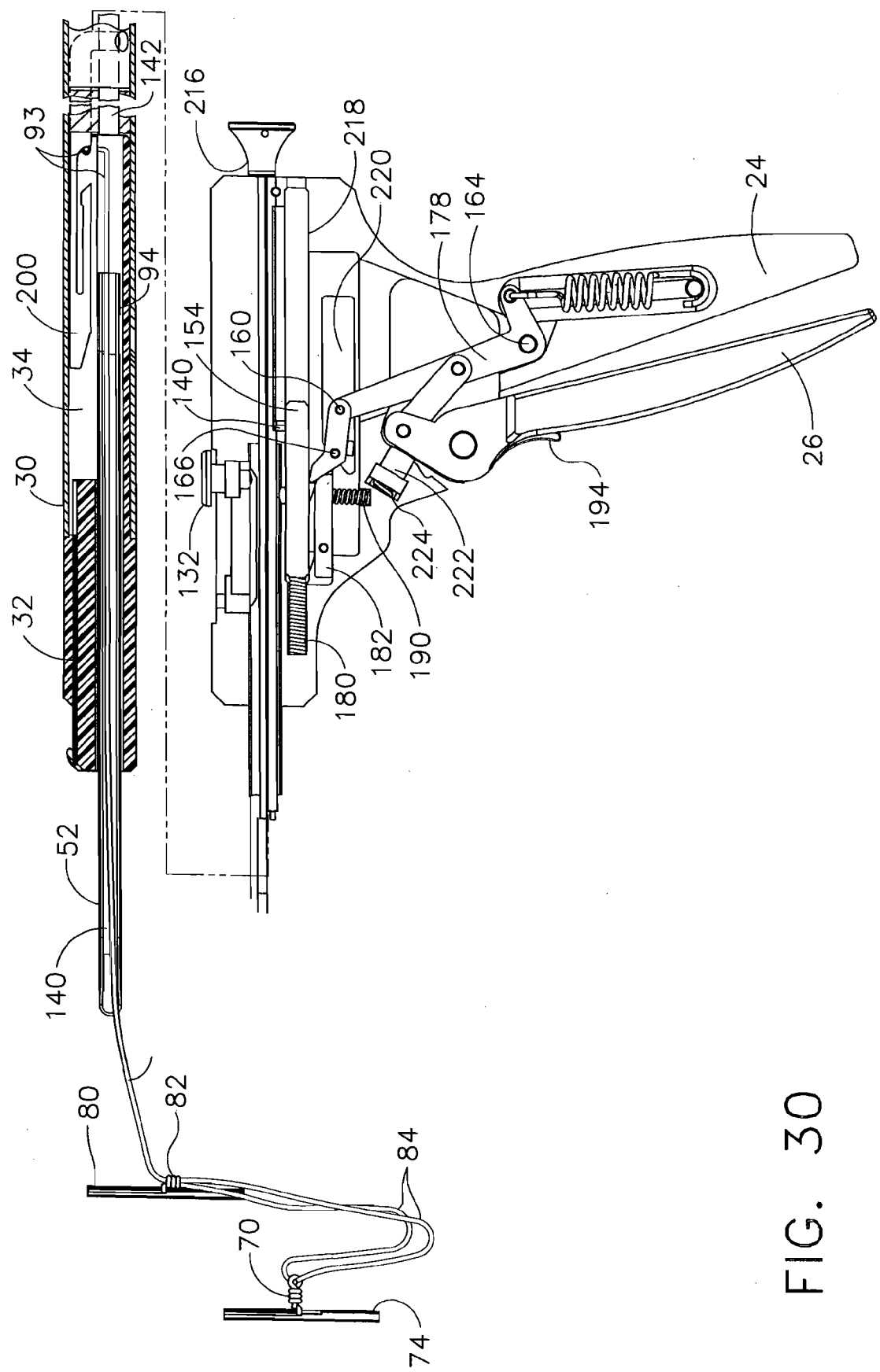
FIG. 30 is a sectional view of the deploying device and cartridge, showing the trigger pivoted proximally to eject a second T-Tag anchor from the needle.

After the initial T-Tag is deployed, needle 52 is removed from the tissue location and reinserted into a second targeted tissue location. To deploy the second T-Tag anchor into the tissue, manual pressure is again applied to trigger 26 to pivot the trigger in the direction of pistol grip 24, as shown in FIG. 30. As trigger 26 pivots, lever 178 pivots about pin 164 to again advance drive pawl 160 distally through track 220 and along the edge of push rod driver 154. Note that drive pawl 160 is not initially engaged with the proximal tooth of push rod driver 154. As drive pawl 160 travels along push rod driver 154, the drive pawl comes into contact with the second, proximal push rod driver tooth. As the drive pawl contacts the second push rod tooth 172, the drive pawl applies a force to the tooth to advance the push rod driver distally through track 218, against the counterforce of push rod driver spring 180. For the second squeeze of trigger 26, the distance that drive pawl 160 advances the push rod driver 154 is substantially the same as the length of a T-Tag anchor. As push rod driver 154 advances, the attached push rod 140 is also advanced through needle 52 the length of a T-Tag anchor. At the initiation of the second trigger stroke, the distal end of push rod 140 is in contact with the proximal end of the second T-Tag anchor 80. The distal end of the second T-Tag anchor is poised at the open distal end of needle 52. As push rod 140 is advanced, the push rod applies force to the proximal end of the T-Tag anchor 80 to expel the anchor through the open distal end of the needle and into or through the penetrated tissue. As the T-Tag anchor deploys, the suture connected to the T-Tag exits the needle through slot 88 and remains extended between the T-Tags 74, 80 and the suture cavity 94 in the cartridge, as shown in FIG. 30.

Figure 31:
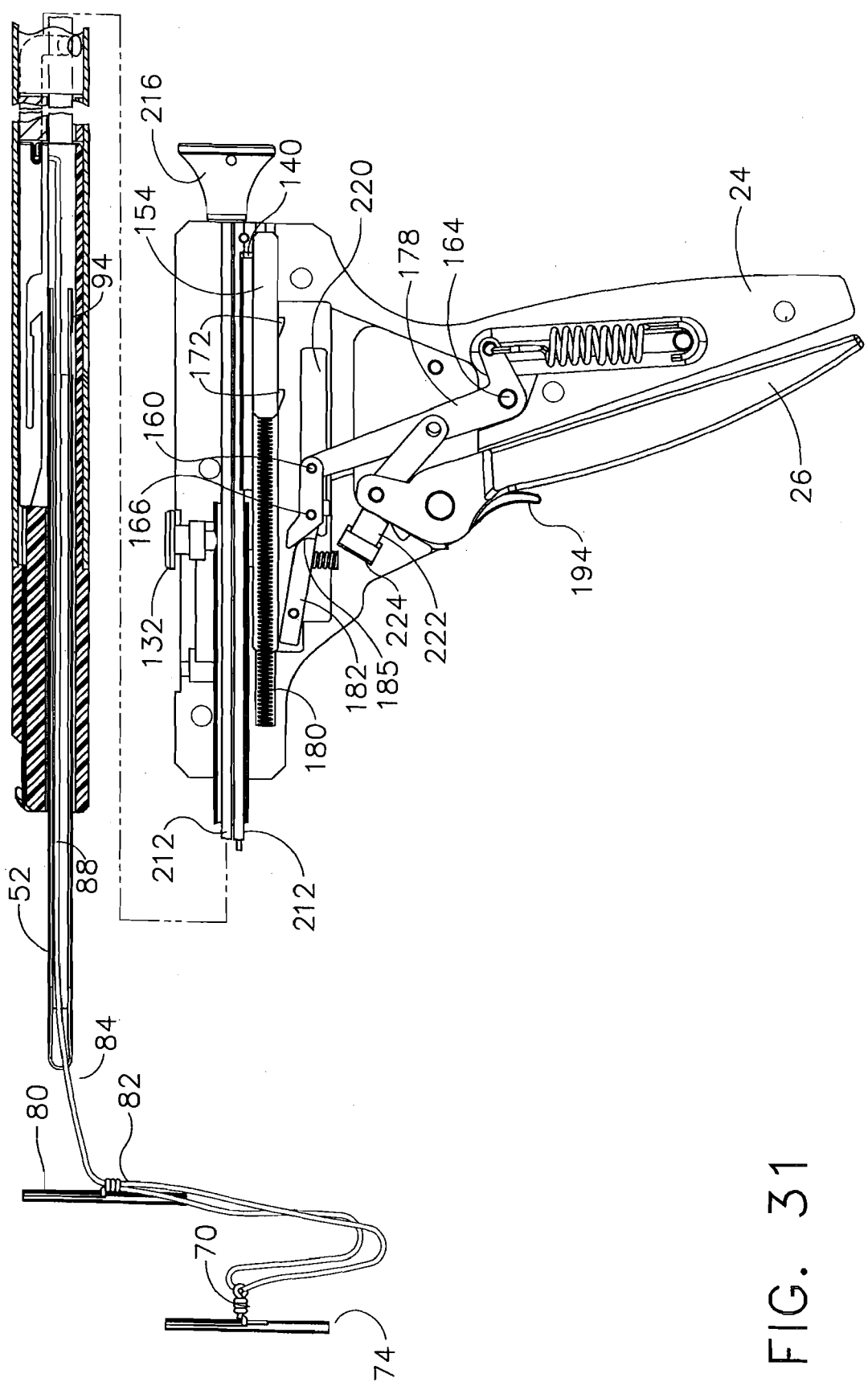
FIG. 31 is a sectional view of the deploying device and cartridge, showing the trigger fully pivoted and the actuating mechanism resetting within the device.

After the second T-Tag anchor has been deployed, device 20 may be reset to pull the push rod 140 back from the cartridge and into housing 30. To reset the device, trigger 26 is pivoted to its fullest extent, against the force of button 222, until the trigger is flush against the pistol grip, as shown in FIG. 31. Fully pivoting primary trigger 26 advances drive pawl 160 even further distally against anti-backup pawl 182. As drive pawl 160 advances, pin 166 continues to follow the upper surface of drive pawl track 220 which transitions into cam surface 230. Cam surface 230 is shown in greater detail in FIG. 24. As pin 166 approaches can surface 230, catch 170 passes around anti-backup pawl catch 184 and into contact with anti-backup pawl cam surface 185. The contact with cam surface 230 forces pin 166 and, correspondingly, drive pawl 160 and anti-backup pawl 182 downward. As both pawls move downward, the pawls disengage from the teeth 172 of the push rod driver 154, as shown in FIG. 31. Freed from the force of the pawls, the spring loaded push rod driver 154 is driven proximally by the force of push rod driver spring 180 back to its initial, proximal starting position at the end of track 218. As push rod driver 154 retracts, the driver pulls push rod 140 from needle 52 and resets the push rod back to its initial position within housing 30 and push rod sheath 142. The resetting of push rod 140 can happen any time after the second T-Tag has been deployed, but must be performed prior to removing cartridge 32 from housing 30 or the cartridge cannot rotate for removal. In addition, if push rod 140 is reset prior to deploying the second T-Tag anchor, two actuations of trigger 26 will still deploy the second tissue anchor.

Figure 25:
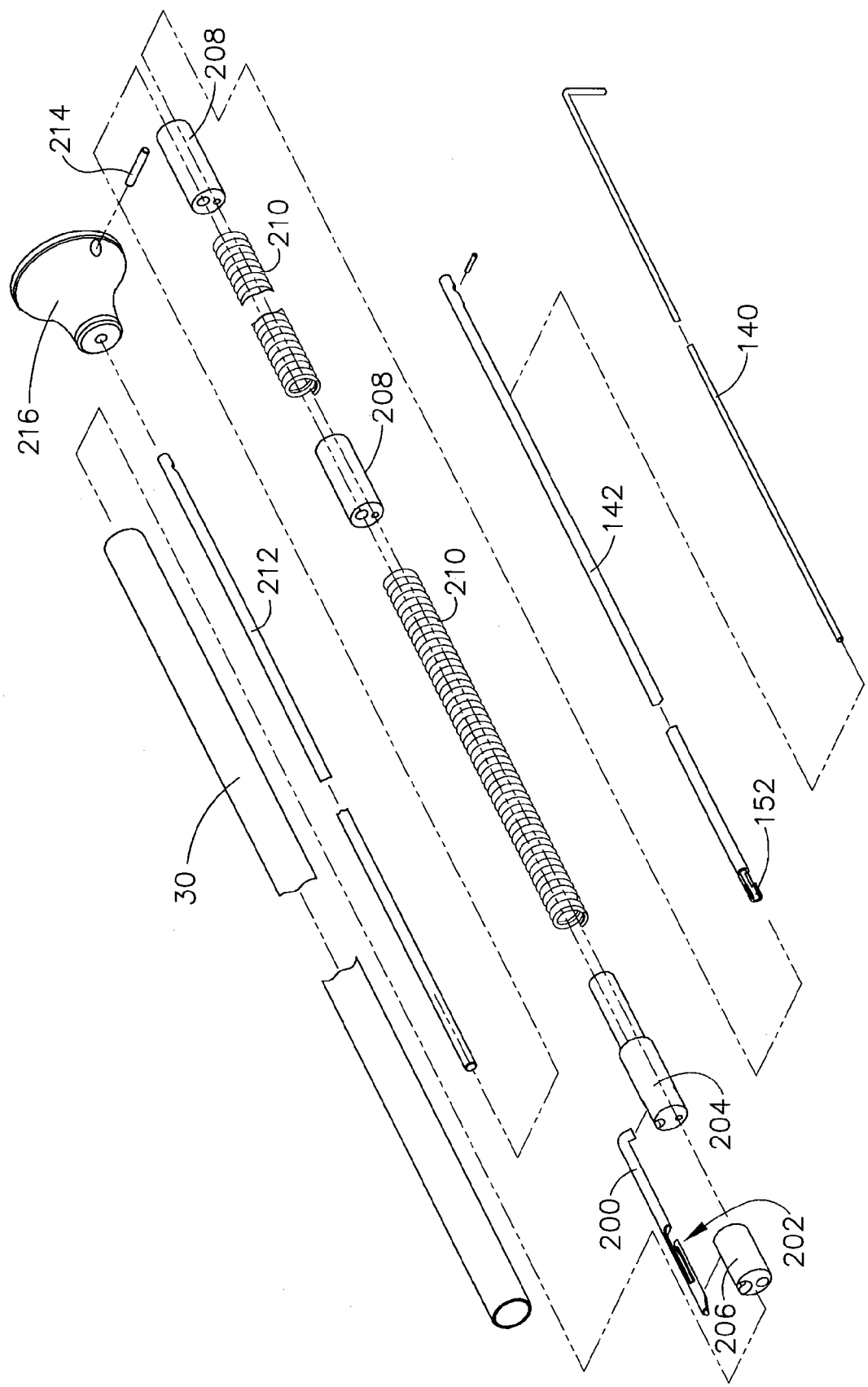
FIG. 25 is an exploded view of the suture cinching assembly and housing for the deploying device.
Figure 32:
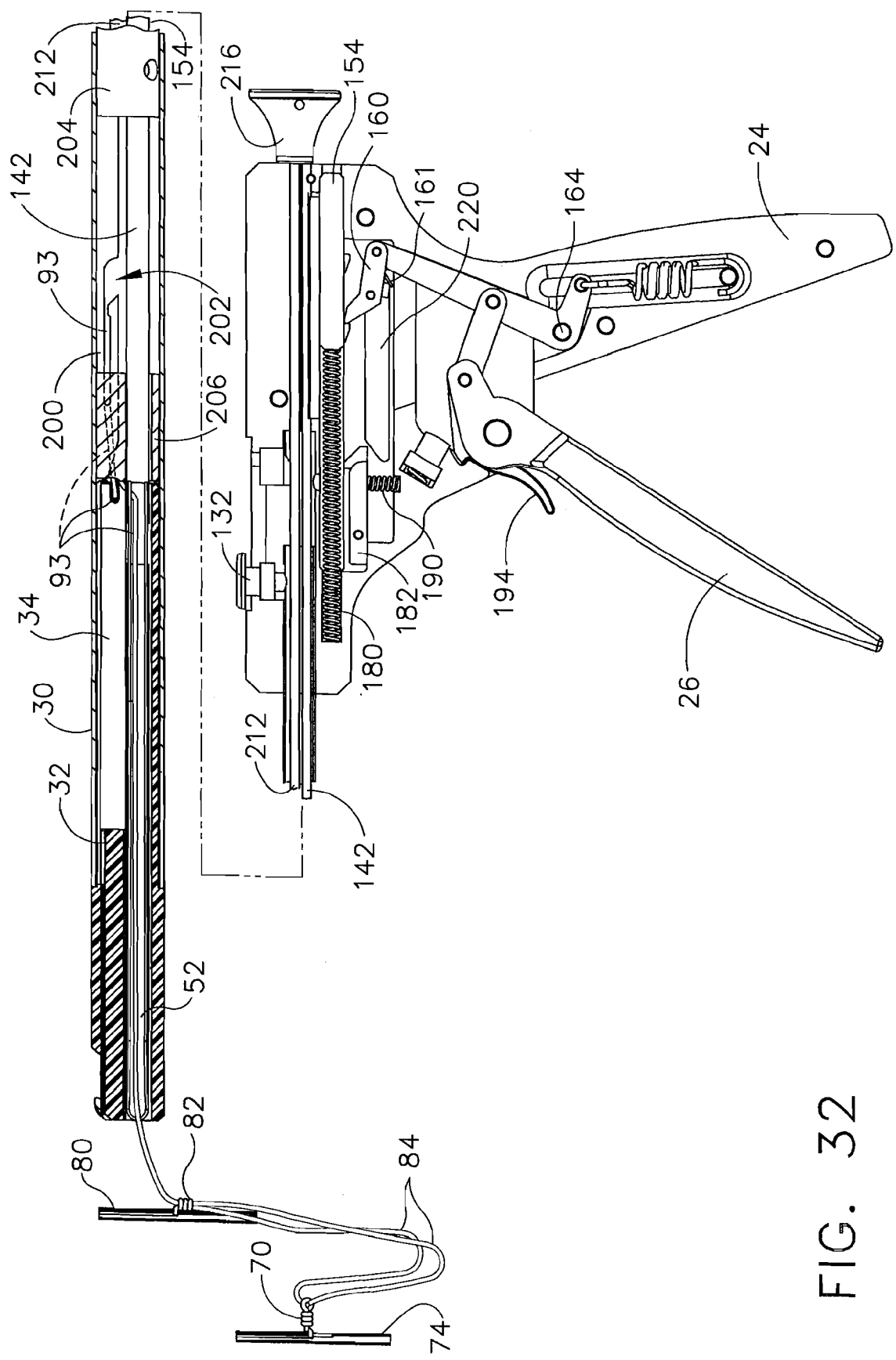
FIG. 32 is a sectional view of the deploying device and cartridge, showing the actuating mechanism reset to an initial position, and the needle being retracted within the housing.
Figure 33:
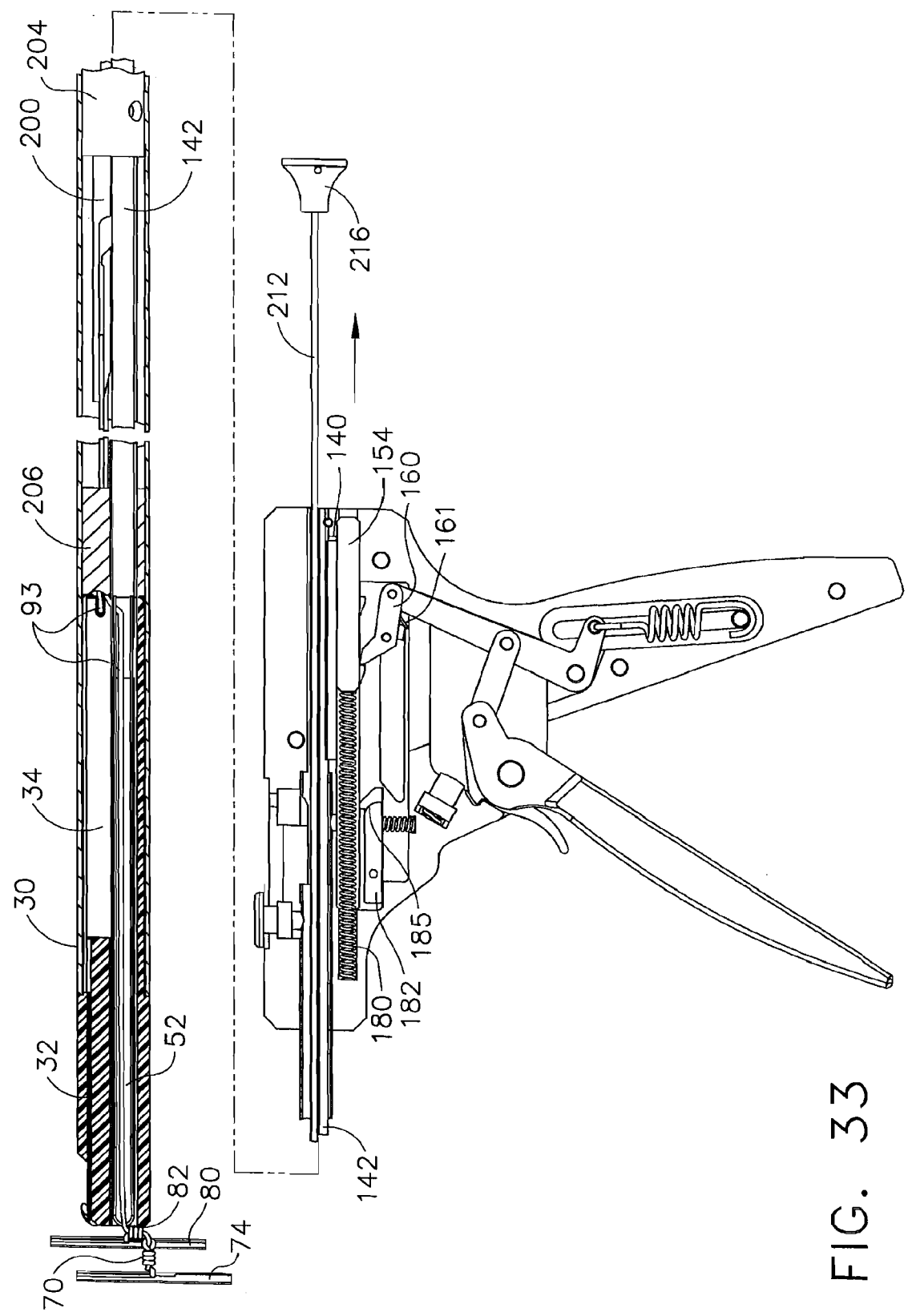
FIG. 33 is a sectional view of the deploying device and cartridge, showing the T-Tag anchors cinched together at the distal tip of the cartridge.

After the second T-Tag anchor is deployed, and the optional resetting of device 20, housing 30 and cartridge 32 are advanced distally by manually depressing button 132 and sliding post 130 along track 134 in the handle, as shown in FIG. 32. Advancing cartridge 32 distally conceals needle 52 back inside of needle cavity 144, so that the tip of the needle is safely within the cartridge. As the cartridge advances, open channel 34 passes distally around the stationary suture grasping member 200. As the cartridge advances forward of the suture grasping member 200, the suture spanning the back of channel 34 is caught within the opening of hook 202 as shown. The opening of hook 202 may be tapered, as shown in FIG. 25, to aid in guiding the suture into the hook. With suture length 93 entrapped within hook 202, a manual proximal pulling force is applied to knob 216. The force on knob 216 is conveyed through pull rod 212 to shuttle 204, to draw the shuttle and, correspondingly, suture grasping member 202 proximally into the housing. The force of the retracting shuttle 204 compresses cinching spring 210. As suture grasping member 200 moves proximally, hook 202 grabs onto and retracts the suture length 93, applying tension to reduce suture length 84 by pulling the suture through suture knot 82 and draws the deployed T-Tag anchors 74, 80 together to appose the surrounding tissue. As mentioned above, loose end 86 of the suture is locked within terminal groove 102 inside cartridge 32. Therefore, suture length 93 is caught between the fixed end in terminal groove 102 and the second end attached within the T-Tag anchor 80. Therefore, as suture length 93 is drawn proximally within housing 30 by hook 202, tension is created in the suture pulling the T-Tag anchors together as shown in FIG. 33.

Figure 34:
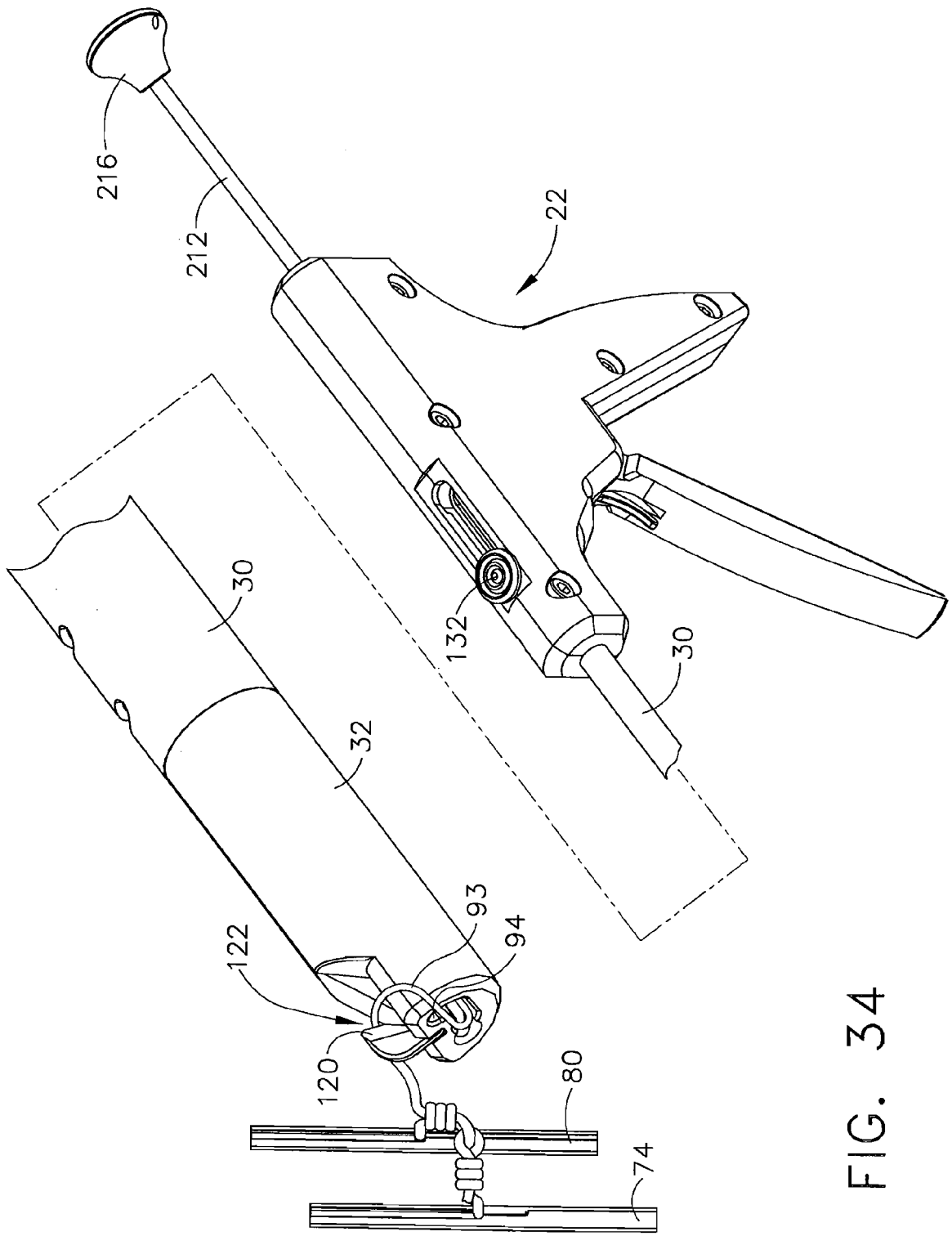
FIG. 34 is a perspective view of the deploying device and cartridge, showing suture extending from the T-Tag anchors and engaging a cutting member on the cartridge.

After the suture has been cinched to set the T-Tag anchors 74, 80 apart the desired distance, the suture grasping member 200 is reset by releasing the proximal pulling force on knob 216. As the force on knob 216 and, thus, on shuttle 204 ceases, the force within the compressed cinching spring 210 is released. Cinching spring 210 expands and propels shuttle 204 and the attached suture grasping member 200 forward to the distal end of housing 30, thus resetting the suture grasping member. After the suture has been cinched, the suture extending between the second T-Tag anchor and the distal end of suture cavity 94 is severed to separate the T-Tag anchors from the cartridge. Cutting member 112 may be used to sever the suture by wrapping the suture through V-notch 122, as shown in FIG. 34. A grasper may be used to assist in drawing the suture into the V-notch. With the suture inside V-notch 122, a pulling force is applied to handle 22 to tension the suture against the blade 120 of the cutting member in order to sever the suture. If a separate grasping instrument is not used to assist in the cutting, tension can be applied to the suture to assist with cutting by applying force to knob 216 as needed. As an alternative to using a cutting member 112, the suture extending from the cinched T-Tag anchors may be severed by passing known surgical instruments through a trocar, or other surgical port or opening, in order to grasp and cut the suture.

Following suture severing, pushrod 140 can be reset into housing 30, if the device was not already reset prior to the cinching of the T-Tag anchors. After the device is reset, and the suture is severed, the cartridge can be removed from the device. To remove cartridge 32, the cartridge is rotated relative to the housing, in the manner described above, to allow the cartridge to slip off of the distal end of the housing. As mentioned above, during severing of the cinched suture, the excess suture is retained within suture cavity 94 of the cartridge and kept attached to the cartridge by size enhancing member 110. As the cartridge is removed from the housing 30, the excess suture slides around grasping member 200 and out of the housing remaining with the cartridge. The excess suture is therefore discarded along with the cartridge following use. After the cartridge is removed from the housing, deploying device 20 is ready for reattachment to and reuse with an additional cartridge.

Figure 35:
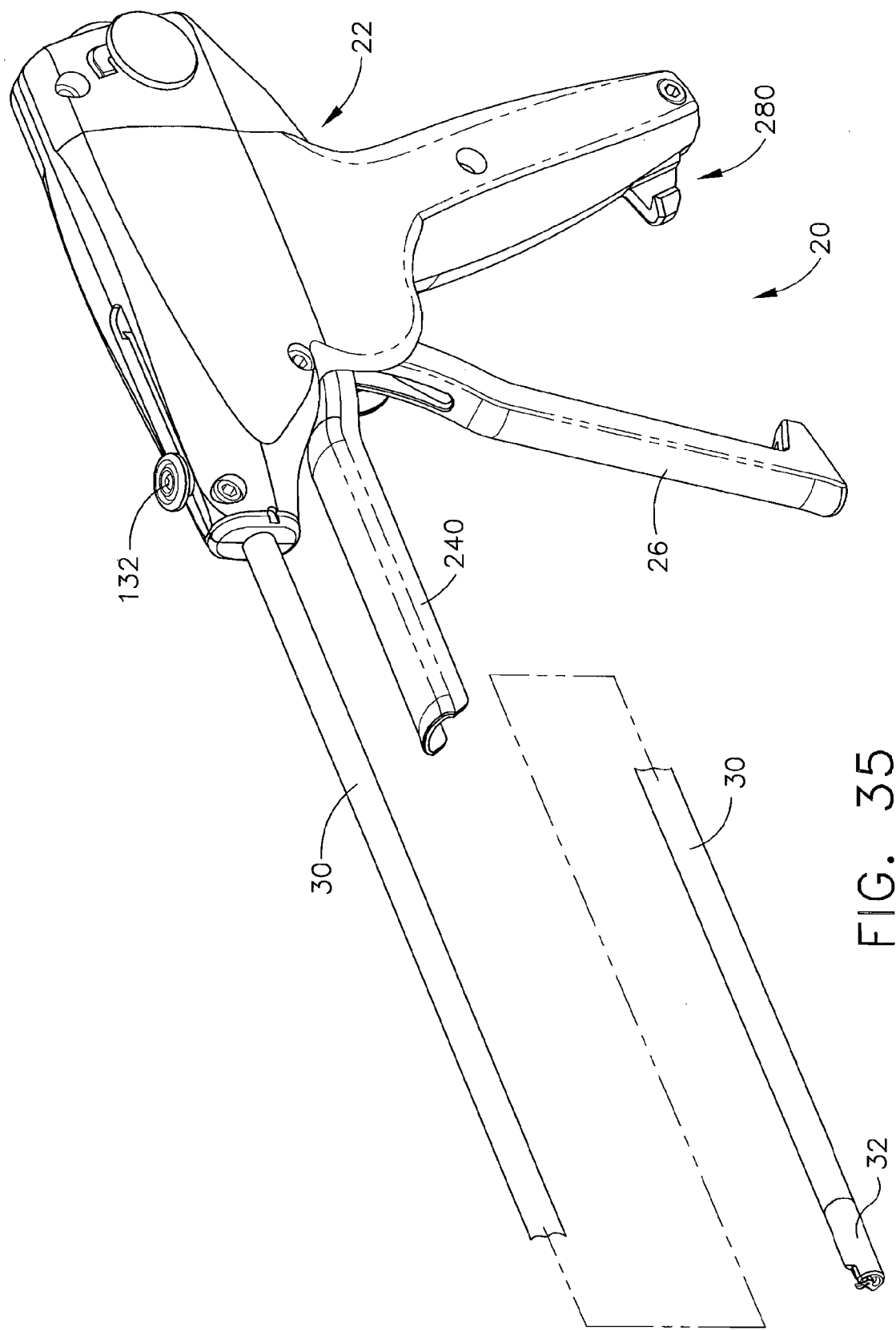
FIG. 35 is a perspective view of a second embodiment for a deploying device shown attached to a cartridge.
Figure 36:
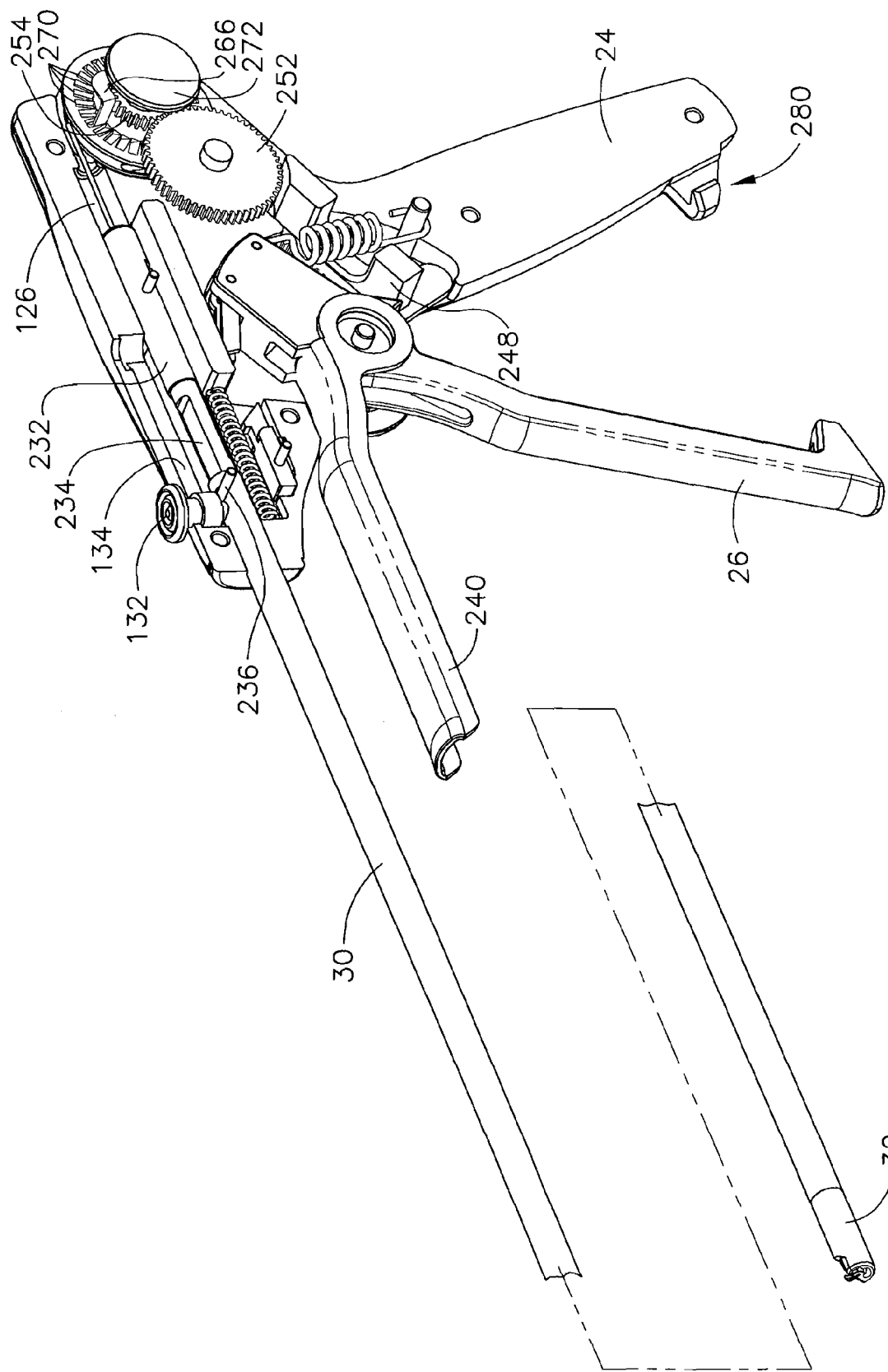
FIG. 36 is a perspective view of the second deploying device embodiment and attached cartridge, shown with the handle casing partially removed.
Figure 37:
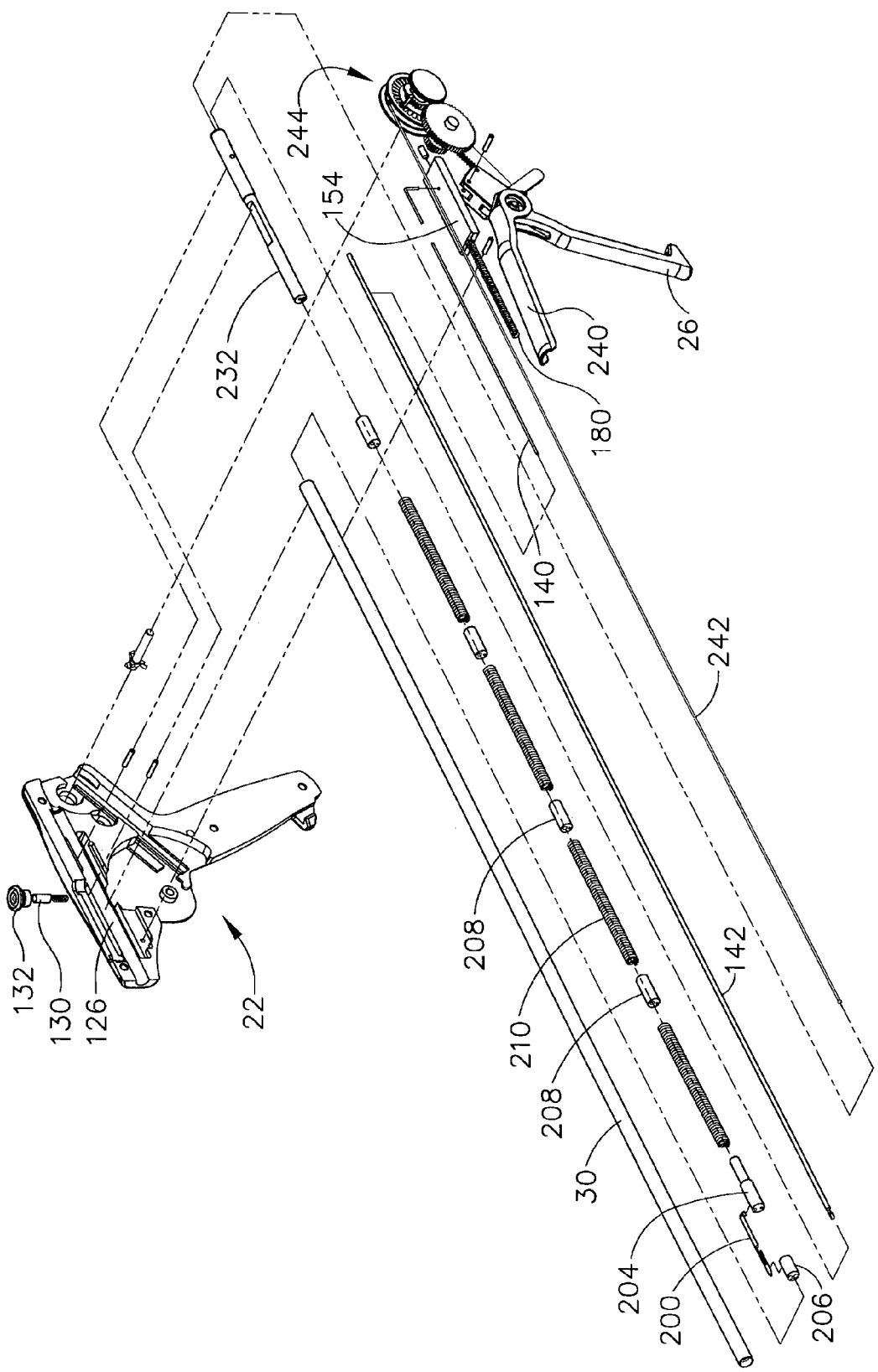
FIG. 37 is a partially exploded view of the housing and handle for the second deploying device embodiment.

FIG. 35 shows a second embodiment for the deploying device. In this embodiment, the cartridge 32 is substantially the same as in the previous embodiment. The handle, however, is modified to enable the device to be operated single-handedly to deploy T-Tag anchors, and cinch and sever suture. In this embodiment, a second hand is necessary only to operate button 132 in order to advance and retract housing 30. As shown in FIGS. 36-37, in this second embodiment, handle 22 is modified to include a cylindrical push rod sheath holder 232. The proximal end of push rod sheath 142 is connected to the distal end of push rod sheath holder 232. Push rod sheath holder 232 is coaxial with housing 30 and is positioned just proximal of the housing within handle channel 126. A distal segment of push rod sheath holder 232 has a smaller diameter than housing 30 to enable the segment to slide within the interior of the housing. An axially extending groove 234 having curved end faces is formed in the upper surface of the distal segment of push rod sheath holder 232. A pin 236 is attached adjacent to the proximal end of housing 30 so as to span across push rod sheath holder groove 234. As housing 30 is retracted or advanced by button 132, pin 236 slides through the sheath holder groove 234. As pin 236 slides through holder groove 234, push rod sheath holder 232 remains stationary within handle channel 126 as housing 30 slides over the holder. After passing through the length of holder groove 234, pin 236 contacts one of the curved ends of the groove. The contact between the moving pin 236 and the curved end face of the holder groove 234 drives the push rod sheath holder 232 in the same direction as the housing 30. To retract the push rod sheath 142 (and also the attached needle 52), pin 236 drives push rod sheath holder 232 to the proximal end of handle channel 126 as post 130 moves from the distal recess to the proximal recess along track 134. The length of groove 234 in push rod sheath holder 232 coincides with the distance which cartridge 32 is retracted in order to expose needle 52 from the distal end of the cartridge. Once pin 236 engages the proximal end face of groove 234, the distance that housing 30 and push rod sheath holder 232 travel together corresponds to the distance that the needle is pulled back proximally in order to align the distal end of push rod 140 with the proximal end of the T-Tag anchor stack inside needle 52. The contact between pin 236 and the end faces of groove 234 enables the push rod sheath holder 232 and, in turn, push rod sheath 142 to be reciprocated by button 132 along with housing 30.

Figure 38:
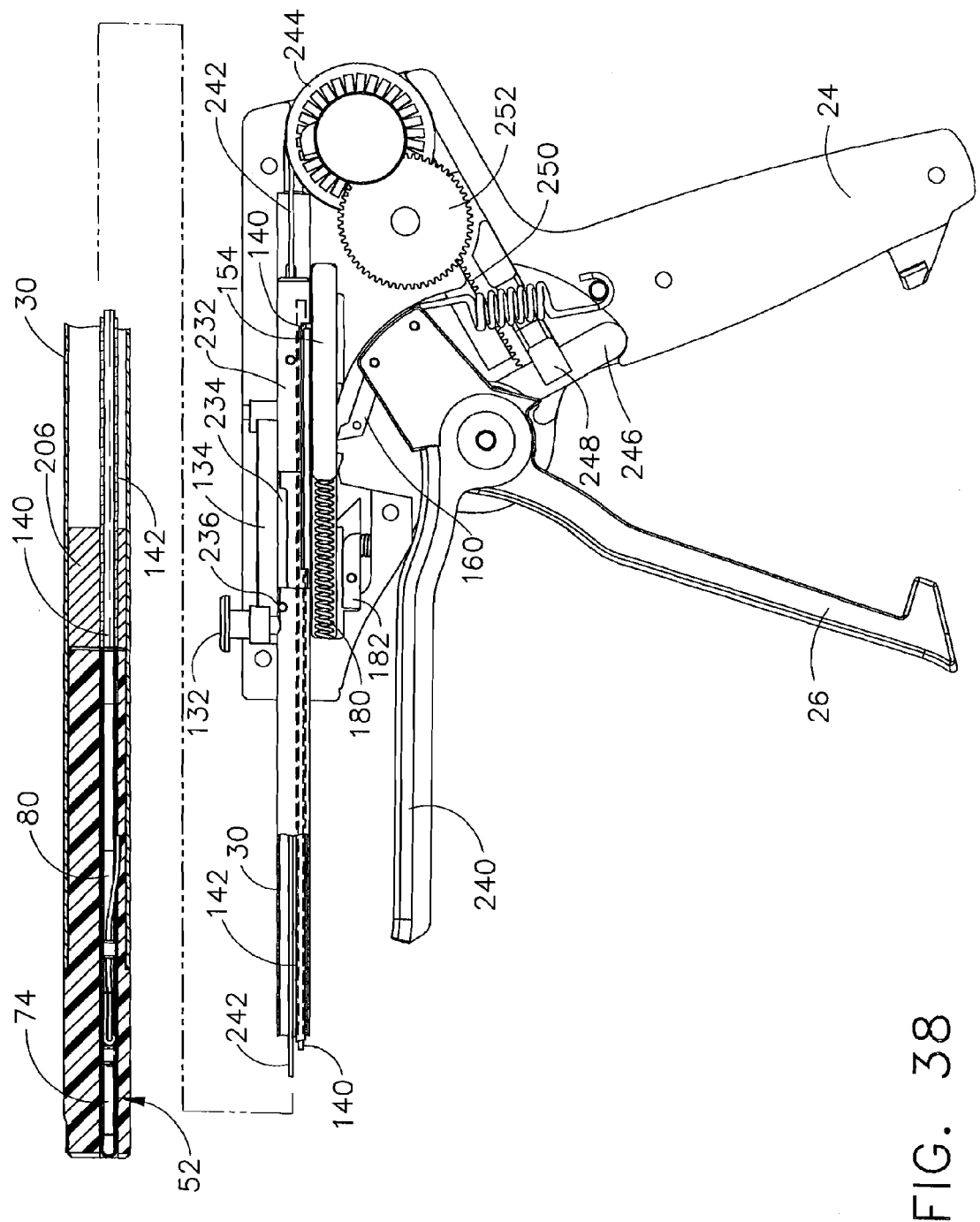
FIG. 38 is a sectional view of a cartridge and second deploying device embodiment, showing the cartridge in a fully distal position covering the needle.
Figure 39:
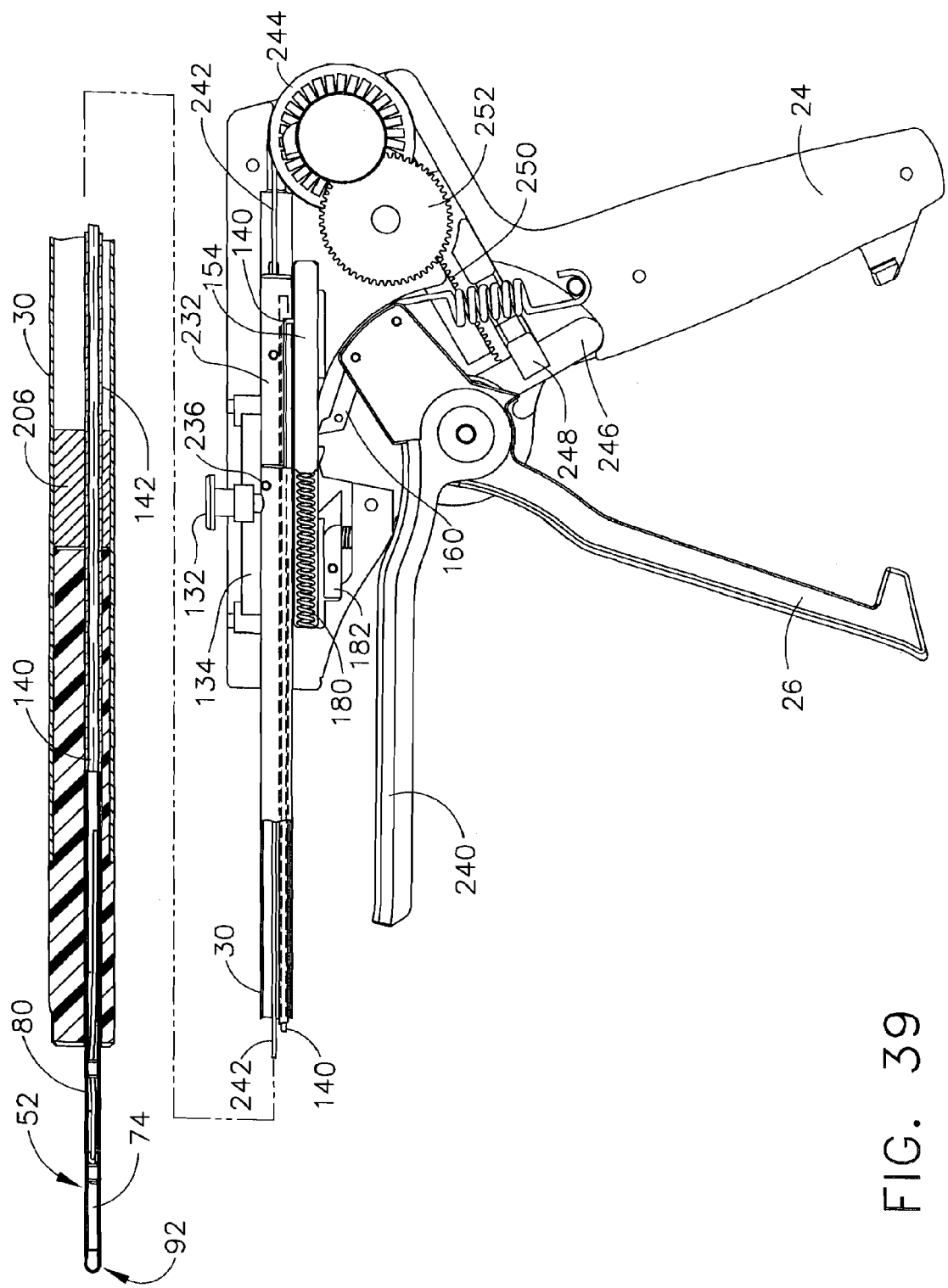
FIG. 39 is a sectional view similar to FIG. 38, showing the cartridge partially retracted to completely expose the needle from the distal end of the cartridge and advance the push rod into the cartridge.
Figure 40:
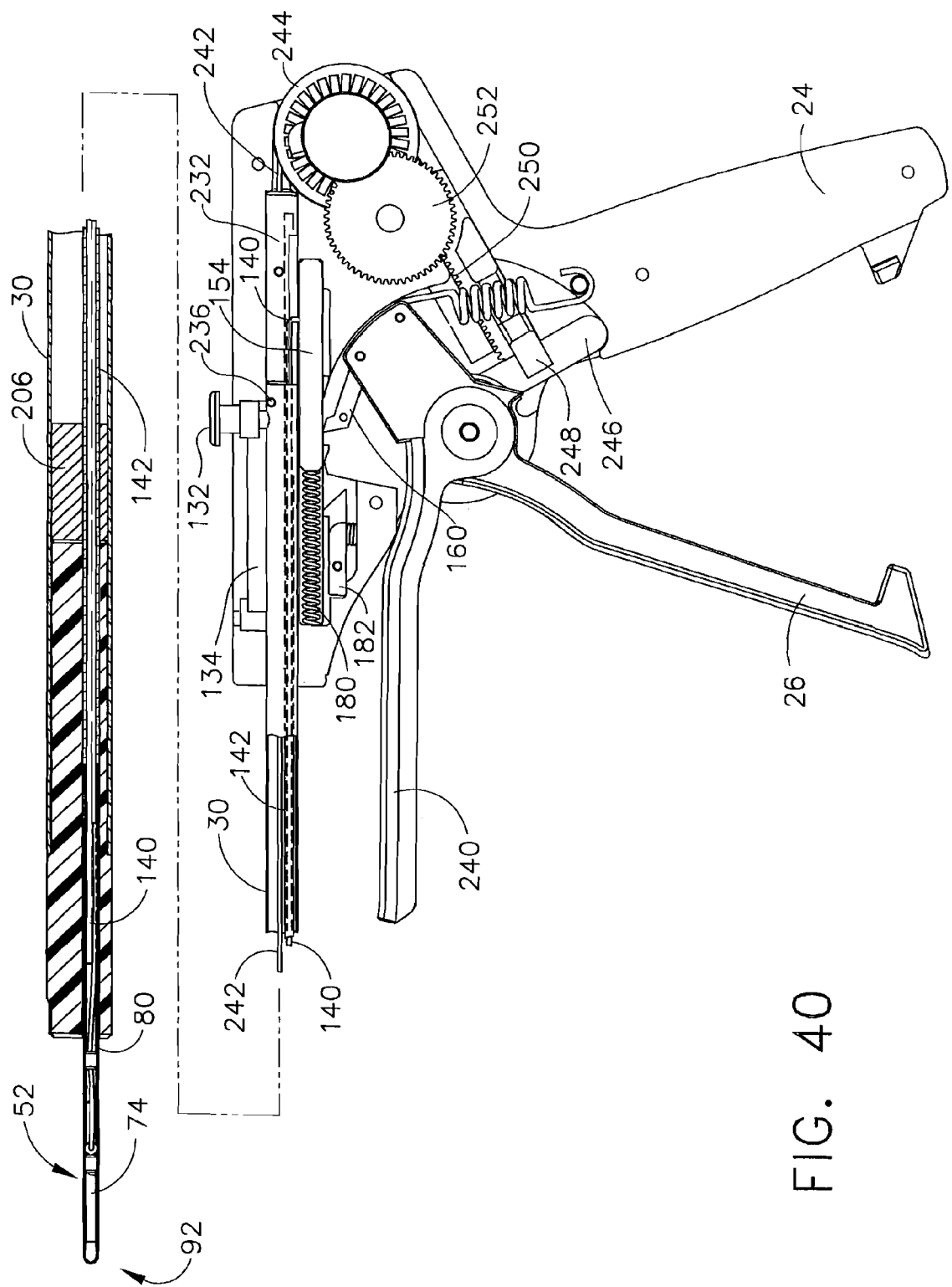
FIG. 40 is a sectional view similar to FIG. 39, showing the cartridge and housing fully retracted to place the push rod in contact with the T-Tag anchor stack in the needle.

FIGS. 38 through 40 show the relative positions of needle 52 and pushrod 140 inside cartridge 32 as the push rod sheath holder 232 and housing 30 are retracted. Note that the motions of suture lengths 84 and 93, the suture grasping member 200, and the shuttle 204 have been omitted from these figures for clarity. FIG. 38 shows the needle 52 fully enclosed within cartridge 32 and push rod 140 adjacent the distal end of push rod sheath 142. This needle and push rod position corresponds to the handle position shown in FIG. 36, in which button 132 is fully distal in track 134 to place the cartridge and housing in a forward position. As button 132 is slid proximally, pin 236 moves through push rod holder groove 234, to allow the housing 30 to slide relative to the stationary push rod sheath holder 232. As the housing moves, cartridge 32 also moves proximally. Needle 52 is attached via push rod sheath 142 to the sheath holder 232. Hence, since the sheath holder is stationary, the needle is also stationary, allowing cartridge 32 to retract away from the needle to expose the distal end of the needle, as shown in FIG. 39. As pin 236 contacts the proximal end face of holder groove 234, the pin pushes push rod sheath holder 232 proximally within handle channel 126. As the push rod sheath holder 232 moves, the holder draws needle 52 proximally, due to the connection between push rod sheath 142 and the needle. As needle 52 moves proximally, the proximal end of the T-Tag anchor stack is drawn towards the distal end of push rod 140. The T-Tag anchor stack contacts the push rod 140 (as shown in FIG. 40) as push rod sheath holder 232 bottoms out at the proximal end of handle channel 126. At this point, post 130 bounces up, under the force of button spring 136, into the proximal recess along track 134 to lock the needle in position. With push rod 140 in contact with the T-Tag anchor stack, trigger 26 is now ready to be squeezed to deploy the initial T-Tag anchor.

In this embodiment, the fastener is deployed in substantially the same manner as described for the previous embodiment. In particular, as shown in FIGS. 27 through 31, prior to deployment of the T-Tag anchors drive pawl 160 is in contact with the distal tooth on push rod driver 154. As trigger 26 is squeezed, the drive pawl pushes against push rod driver 154, which in turn advances push rod 140 against the T-Tag anchor stack to deploy the first T-Tag anchor. As trigger 26 is squeezed, tactile feedback is provided to the surgeon to indicate when the T-Tag has been deployed. In the second embodiment, this tactile feedback is provided by a latching mechanism 280 at the base of the trigger 26 and pistol grip 24, as shown in FIG. 36. After the first T-Tag anchor is deployed, the latching mechanism 280 is disengaged and the trigger 26 is released, allowing drive pawl 160 to spring back to its initial position. As drive pawl 160 springs back, push rod driver 154 remains stationary, due to the contact between the first distal push rod driver tooth and anti-backup pawl 182, as shown in FIG. 29. As drive pawl 160 springs back, the drive pawl catch engages the second, more proximal push rod driver tooth. This places drive pawl 160 in position to advance the push rod driver 154 again with the next trigger squeeze, to drive push rod 140 further distally to expel the second T-Tag anchor. With this mechanism, each squeeze of trigger 26 advances the push rod distally approximately the length of one T-Tag anchor. This approach works because the T-Tag stack is initially brought into direct contact with the push rod which is a notable difference from the first embodiment.

Between deployment of the first and second T-Tag anchors, button 132 may be drawn distally the full distance of track 134, to pull cartridge 32 distally over the tip of needle 52. With needle tip 92 covered, deploying device 20 may be used to probe the cavity wall and determine the second targeted tissue area. After the desired tissue location is determined, button 132 is again depressed to slide post 130 proximally the full length of track 134 to expose needle 52 and draw the needle 52 back. As the needle is drawn proximally, push rod 140 contacts the proximal end of the second T-Tag anchor. The device 20 is thus ready to fire the second T-Tag anchor of the fastener.

Figure 41:
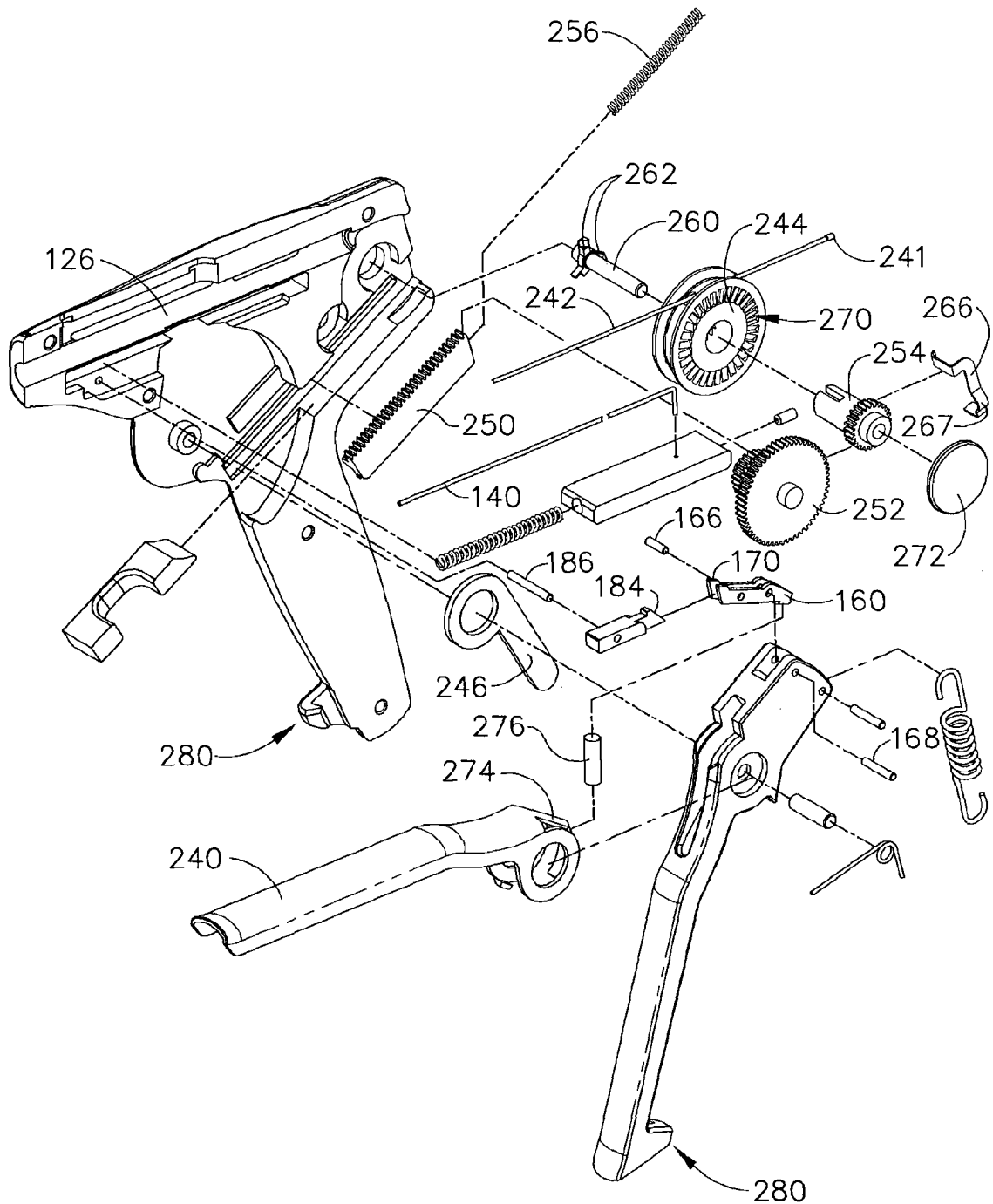
FIG. 41 is an exploded view of the handle for the second deploying device embodiment.
Figure 42:
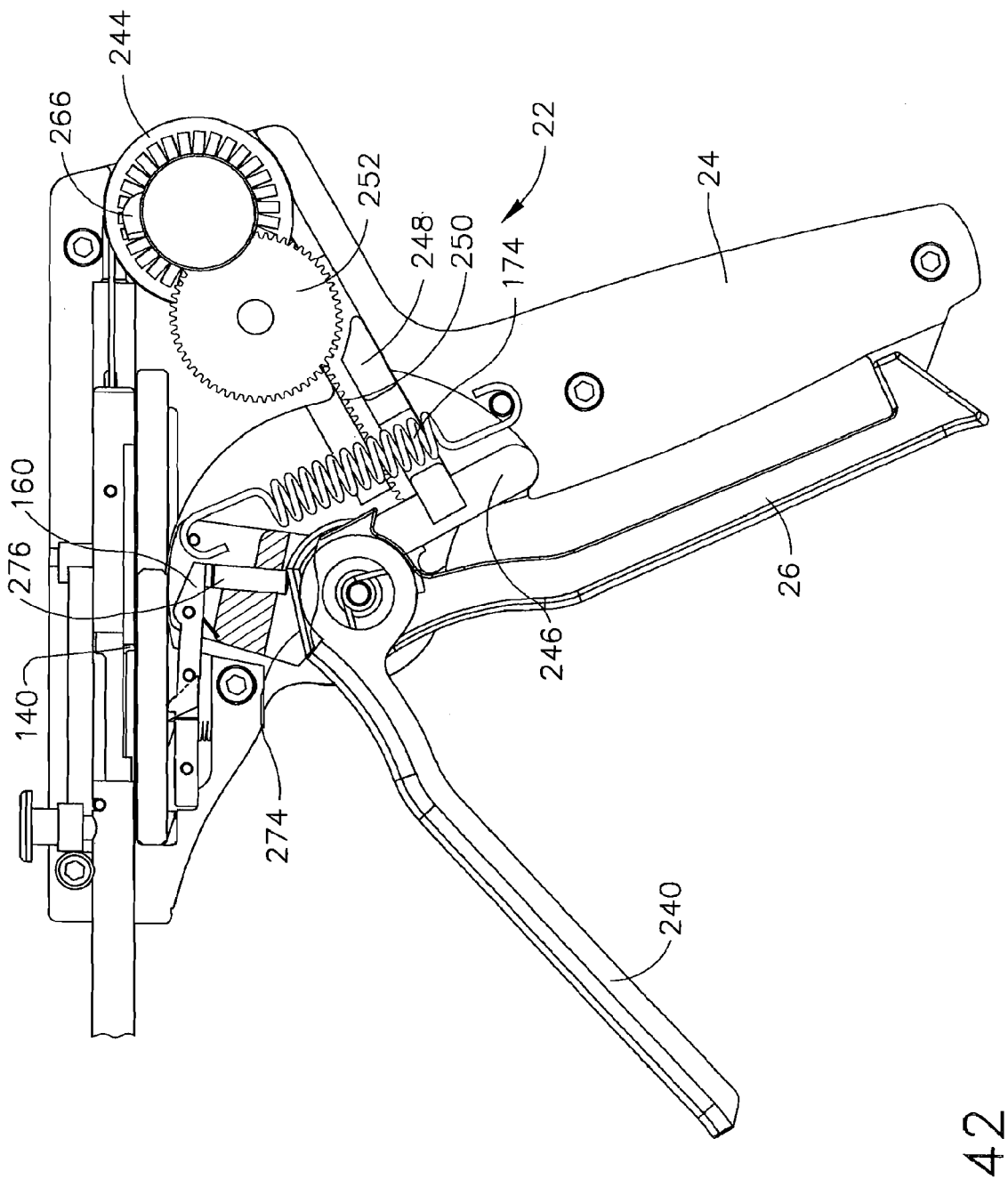
FIG. 42 is a side view of the handle, with the outer casing removed, showing another embodiment for resetting the actuating mechanism of the device.
Figure 43:
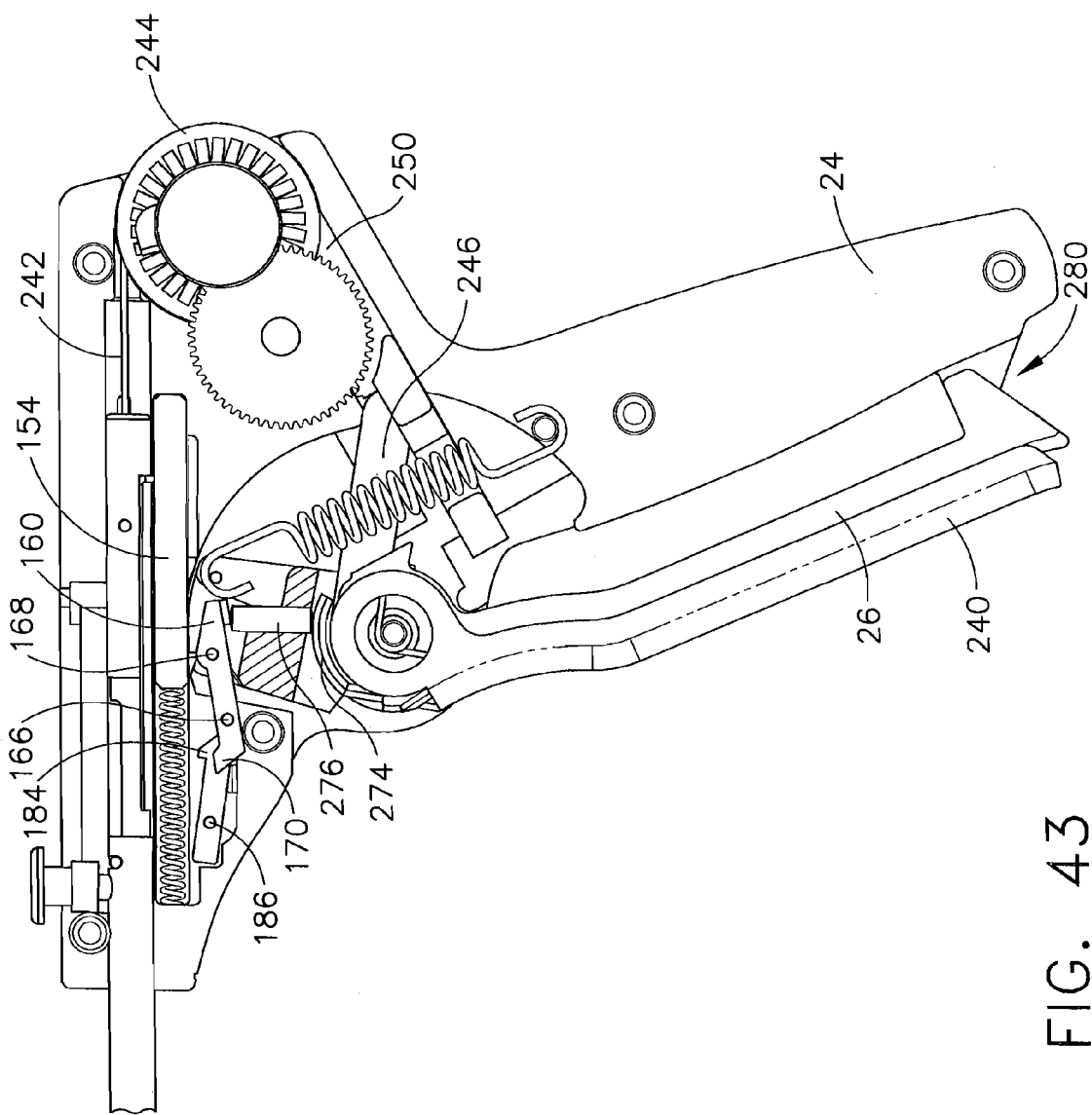
FIG. 43 is a side handle view, similar to FIG. 42, showing the trigger fully pivoted and the actuating mechanism resetting within the device.
Figure 44:
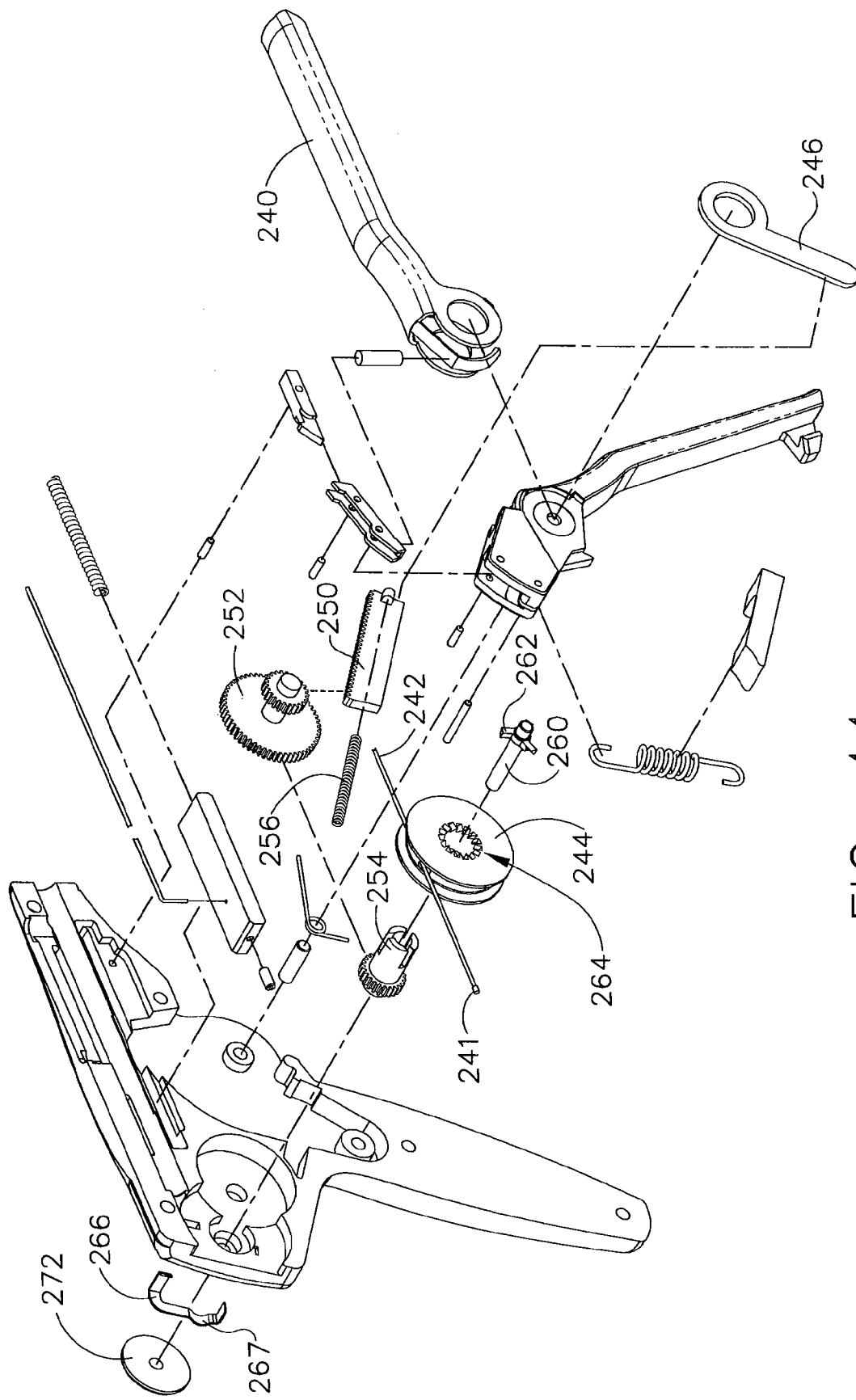
FIG. 44 is an exploded view of the handle for the second deploying device embodiment, showing the opposite side of the handle from that shown in FIG. 41.

After the second T-Tag anchor is deployed, the device can be reset to place push rod 140 back inside of housing 30. In the second embodiment described herein, the actuator further includes a secondary trigger 240. Secondary trigger 240 is located on the distal side of handle 22, between the primary trigger 26 and housing 30, and within easy reach by the same hand that grips the primary trigger. One of the functions of secondary trigger 240 is to control the resetting of the device. As shown in FIGS. 41-43, secondary trigger 240 includes a cam surface 274 at the fixed end of the trigger. Cam surface 274 rests against one end of a release post 276, which is contained within the primary trigger 26. With trigger 26 held in place by latching mechanism 280, the opposite end of release post 276 is in contact with the proximal end of drive pawl 160. With the primary trigger 26 held in place by the latching mechanism, the deploying device is reset by squeezing the secondary trigger 240 to rotate the secondary trigger towards the primary trigger. As the secondary trigger rotates, release post 276 is forced to follow the path of cam surface 274 which progresses at an inclined angle. As release post 276 follows the inclining cam surface 274, the release post is driven upwardly against the proximal end of the drive pawl, as shown in FIG. 43. This upward force on drive pawl 160 pivots the drive pawl about pin 168, causing the drive pawl catch 170 to move downward. As the catch on drive pawl 160 pivots downward, pin 166, located between the sides of the drive pawl, engages the nose of anti-backup pawl catch 184, forcing the anti-backup pawl catch to also pivot in a downward direction about pin 186. As drive pawl 160 and anti-backup pawl 182 rotate downward under the force of release post 276, the secondary tooth on push rod driver 154 is freed from the pawls, allowing the spring-loaded push rod driver to retract back to its initial, proximal position.

This method of resetting the deploying device can be coupled with the action of cinching the suture to bring the T-Tag anchors together. FIGS. 37, 41 and 42 show an alternative embodiment for cinching suture in which secondary trigger 240 is employed for pulling on the loose suture length. In this embodiment, as in the previous embodiment, a suture grasping member 200 is provided within housing 30 for grabbing onto a stretch of suture spanning the proximal end of the cartridge. Suture grasping member 200 is again attached to a shuttle 204. Likewise, a cinching spring 210 (having a plurality of springs and connecting pieces 208) again extends proximally from the shuttle 204, substantially through the length of housing 30, for resetting the suture grasping member 200 following cinching. In this embodiment, however, a flexible pulling member 242 is attached to the proximal end of shuttle 204 for drawing the shuttle proximally within the housing. As shown in FIG. 37, the flexible pulling member 242 extends proximal of shuttle 204 through cinching spring 210 and connecting pieces 208. The proximal end of flexible pulling member 242 is attached to a spool 244 at the end of handle channel 126. A crimp or knot 241, shown in FIG. 41 is formed in the proximal end of pulling member 242 for holding the pulling member within a slot in spool 244. Flexible pulling member 242 is connected to spool 244 so as to curl around the top of the spool as the spool is rotated. Spool 244 rotates within handle 22 to wind the flexible pulling member 242 onto the spool. As pulling member 242 is wound onto spool 244, the pulling member applies a proximal directed force to suture grasping member 200, via shuttle 204, to draw the suture proximally into housing 30.

Figure 45:
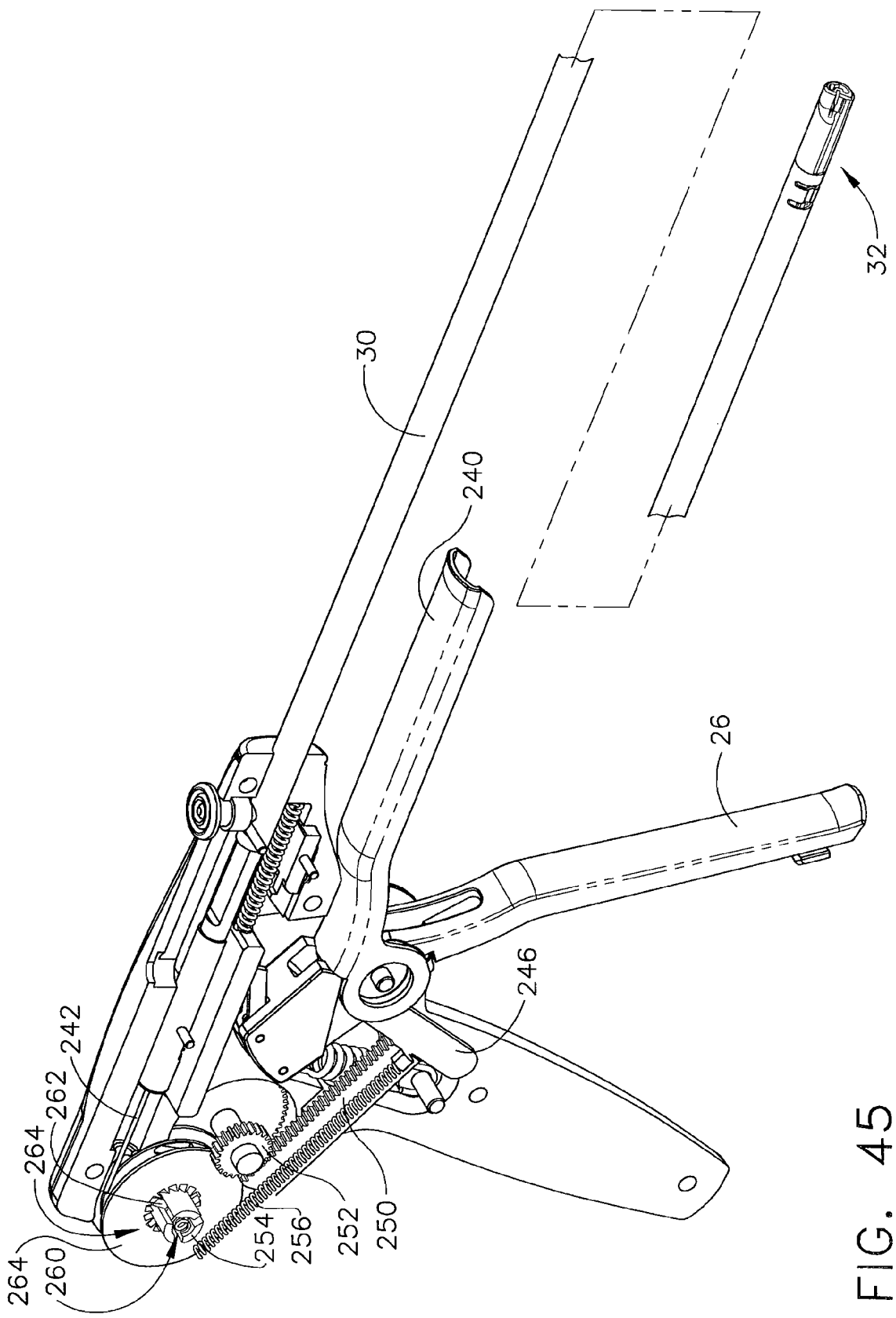
FIG. 45 is a perspective view of the second deploying device embodiment and attached cartridge, shown with the handle casing removed and viewed from the opposite side of the device from the view shown in FIG. 36.

In this embodiment, spool 244 is rotated by applying a squeezing motion to secondary trigger 240. As shown in FIGS. 41, 42 and 45, a lever 246 is attached to secondary trigger 240 and is pivoted in response to the movement of the trigger. Lever 246 is in turn attached to a rack 250 that inclines at an angle towards the proximal end of the handle. A lever guide 248 extends over lever 246 and partially along rack 250 to constrain the lever against the rack. Lever guide 248 is held in place by features in the housing and has a passage for the drive pawl spring 174. Rack 250 includes a plurality of teeth which engage a compound gear 252. Compound gear 252 is in turn mated with a spool gear 254, which is affixed to spool 244. A spring 256 is attached to the rack 250 to drive the return of the rack 250, lever 246, and secondary trigger 240 to a starting position. A spool drive 260 is affixed to spool gear 254 for rotation by the gear. The spool drive 260 includes a plurality of drive pins 262 that rotate a ring of openings or teeth 264 on a first side of the spool. A spool anti-backup pawl 266 is located on an opposite side of spool 244 to engage a second ring of openings or teeth 270 on the opposite side of the spool. As shown best in FIGS. 36 and 41, the spool openings in the second ring 270 are formed with a ramped face in the clockwise direction, and a cut-off face in the counter-clockwise direction. A release button 272 is reciprocally attached to the shaft of spool gear 254 in an offset relationship to spool anti-backup pawl 266. A section 267 of spool anti-backup pawl 266 protrudes outwardly in the direction of release button 272 to make contact with the button when the button is depressed towards spool gear 254.

Following deployment of the second T-Tag anchor 80 and resetting of the device, secondary trigger 240 is squeezed to cinch the suture between the T-Tag anchors (resetting the push rod to its starting position). Squeezing secondary trigger 240 drives lever 246 into rack 250, which in turn moves proximally, rotating compound gear 252. The rotation of compound gear 252 in turn rotates spool gear 254. Drive pins 262 affixed to spool gear 254 engage spool teeth 264, to rotate spool 244 in response to rotation of the spool gear. As spool 244 rotates, flexible pulling member 242 is pulled proximally through handle 22 and wound onto the spool. In the embodiment shown in the Figures, the rack and gears are designed to rotate spool 244 in a clockwise direction to wind up pulling member 242. As shown, spool gear 254 and compound gear 252 are selected to enable the T-Tag anchors to be completely cinched together with two squeezes of the secondary trigger 240. A balance between loads, gear ratio, and user needs allow as fine (several squeezes) or as coarse (as little as one squeeze) a control on the cinching rate as desired. Spool anti-backup pawl 266 allows spool 244 to be rotated by the drive pins. Spool anti-backup pawl 266 moves between the teeth in the second ring 270 by riding up the ramped face of the openings. The differing surfaces within the spool anti-backup pawl teeth 270 allow the spool 244 to rotate in a direction to take up the flexible pulling member 242, but prevent the spool from rotating in a counterclockwise direction to release the pulling member when the secondary trigger is released, such as between squeezes. When the secondary trigger 240 is released, the contact between the cut-off face of the spool teeth 270 and the end of the anti-backup pawl 266 prevents the spool from rotating in a direction to unwind the pulling member. Drive pins are permitted to rotate along spool teeth 264 once the secondary trigger is released. Accordingly, multiple squeezes can be applied to secondary trigger 240 without pulling member 242 being released unintentionally from the spool. At this time, the suture may be severed using the cartridge cutting member 112 described above. Alternatively, the suture may be severed using conventional surgical cutting instruments that are passed through one or more ports to reach the cinched T-Tag anchors.

After pulling member 242 has been sufficiently wound onto spool 244 to tension the suture and cinch the T-Tag anchors together, suture grasping member 200 is reset to its initial position at the distal end of the housing. To reset suture grasping member 200, release button 272 is depressed towards spool gear 254. As release button 272 is depressed, the button contacts the protruding section 267 of spool anti-backup pawl 266, creating a lever in the anti-backup pawl that drives the end of the anti-backup pawl out of contact with spool teeth 270. When spool anti-backup pawl 266 disengages from spool teeth 270, spool 244 is no longer prevented from allowing the spool to unwind. With the spool free to unwind, cinching spring 210 expands, driving shuttle 204 and the attached suture grasping member 200 distally within housing 30 back to their initial positions causing the pulling member to completely unwind from the spool. After suture grasping member 200 has been returned to its initial position to release the tension on the suture, the suture is severed to separate the T-Tag anchors from the cartridge. If not previously performed, the suture may be severed using the cartridge cutting member 112 described above at this time. Alternatively, the suture may be severed using conventional surgical cutting instruments that are passed through one or more ports to reach the cinched T-Tag anchors.

As mentioned above, the lower edges of primary trigger 26 and pistol grip 24 include a latching mechanism 280 which engages after each squeeze of the primary trigger. Latching mechanism 280 facilitates the squeezing of secondary trigger 240 during suture cinching and device resetting, by holding the primary trigger against the pistol grip 24 and out of the way of the pivoting secondary trigger. Latching mechanism 280 is released after each squeeze of primary trigger 26 (i.e. after each T-Tag anchor is deployed) in order to fire an additional T-Tag anchor from the device. Latching mechanism 280 can be released by applying pressure to trigger 26 in a direction out of the plane of the deploying device. This creates a gap between the latching mechanism on the trigger 26 and the latching mechanism on the pistol grip 24. The gap between the catches enables the catches to be separated, and allows primary trigger 26 to spring back to its initial position away from the pistol grip 24.

Figure 46:
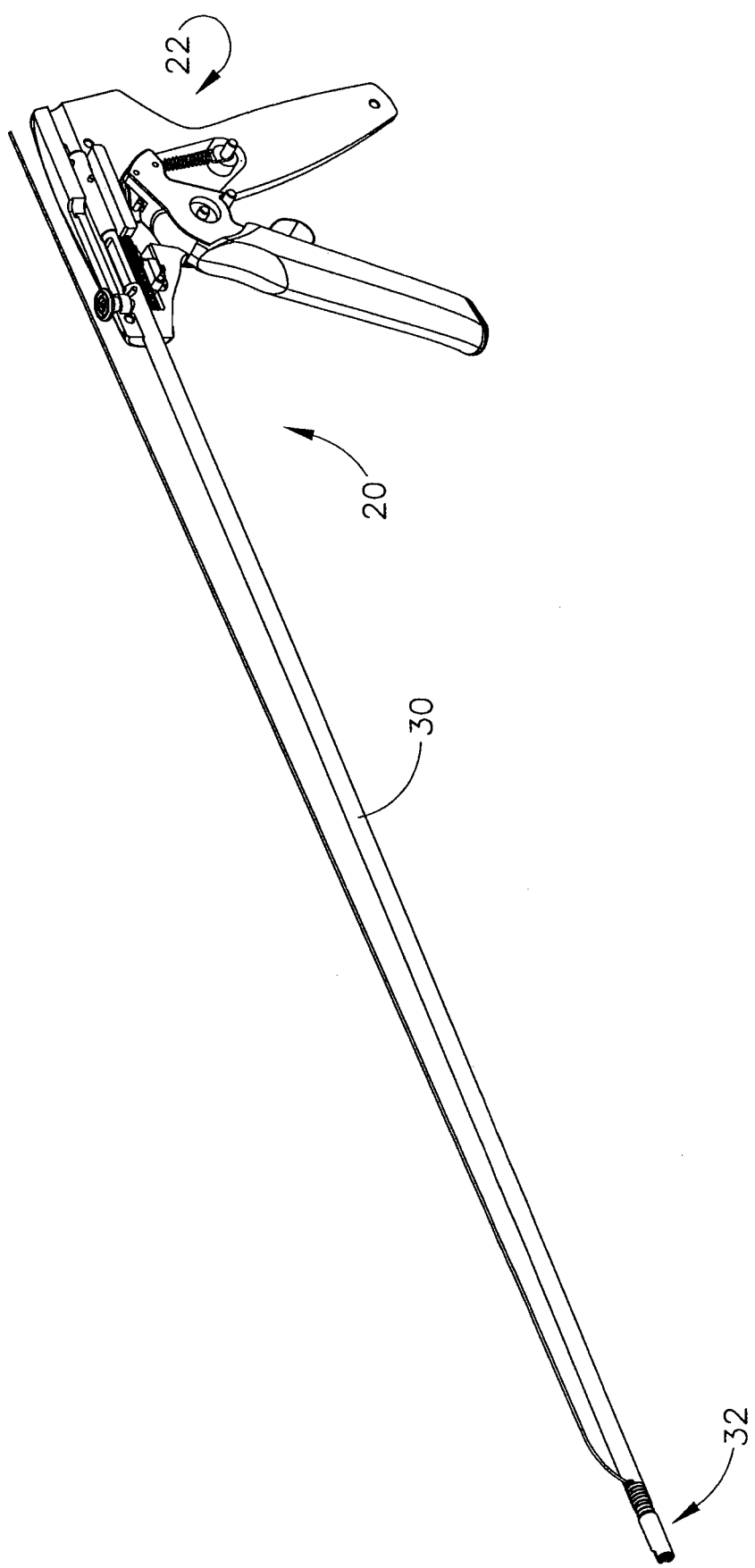
FIG. 46 is a perspective view showing a third embodiment for a deploying device and an attached cartridge, shown with the handle casing partially removed.
Figure 49:
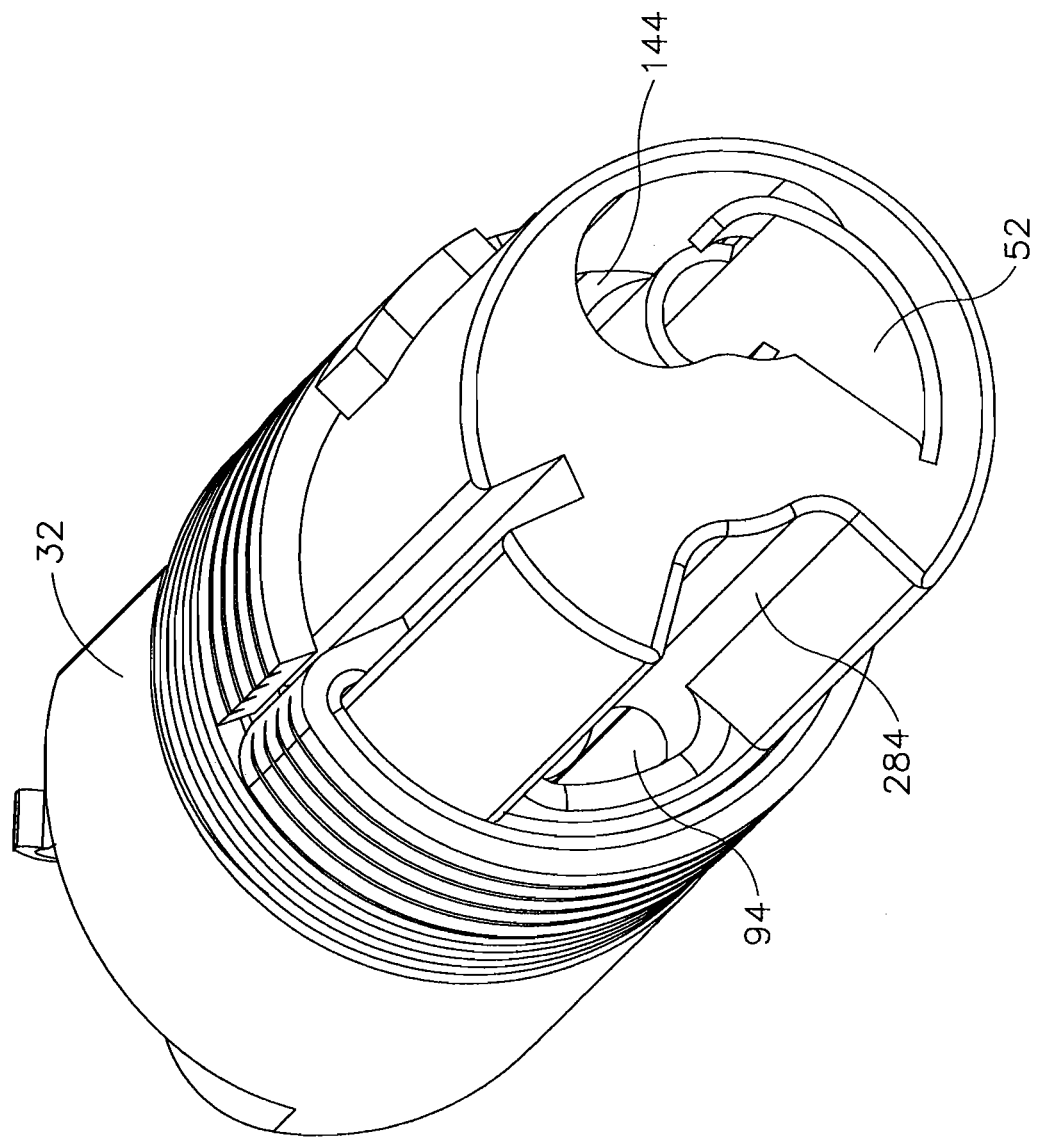
FIG. 49 is a proximal end view of the cartridge for the third embodiment.

FIG. 46 shows another embodiment for the present invention, in which the cartridge is modified to provide a suture opening through the side of the cartridge. In this embodiment, the cartridge 32 is again removably attachable to the distal end of the deploying device 20 by any of the cartridge attachment methods described above. The cartridge 32 includes a retractable needle with a fastener comprising a pair of T-Tag anchors at least partially enclosed within the needle. The T-Tag anchors may be pre-tied together with suture prior to insertion into needle 52, in a similar manner to that described above. Prior to deployment, the suture from the T-Tag anchors is contained within a suture cavity inside the cartridge. The loose end 86 of the suture is passed from the suture cavity outside of the cartridge through a side opening 282, as shown in FIGS. 47 and 48. Side opening 282 is formed as a cutout in the distal end of the deploying device housing 30. When the cartridge 32 is attached to housing 30, the cutout mates up against the cartridge adjacent the proximal end of suture cavity 94. As shown in FIG. 49, the proximal end of cartridge 32 is recessed inward at the proximal suture cavity opening 94 to form a pathway 284 for the suture to exit the cartridge.

Figure 50:
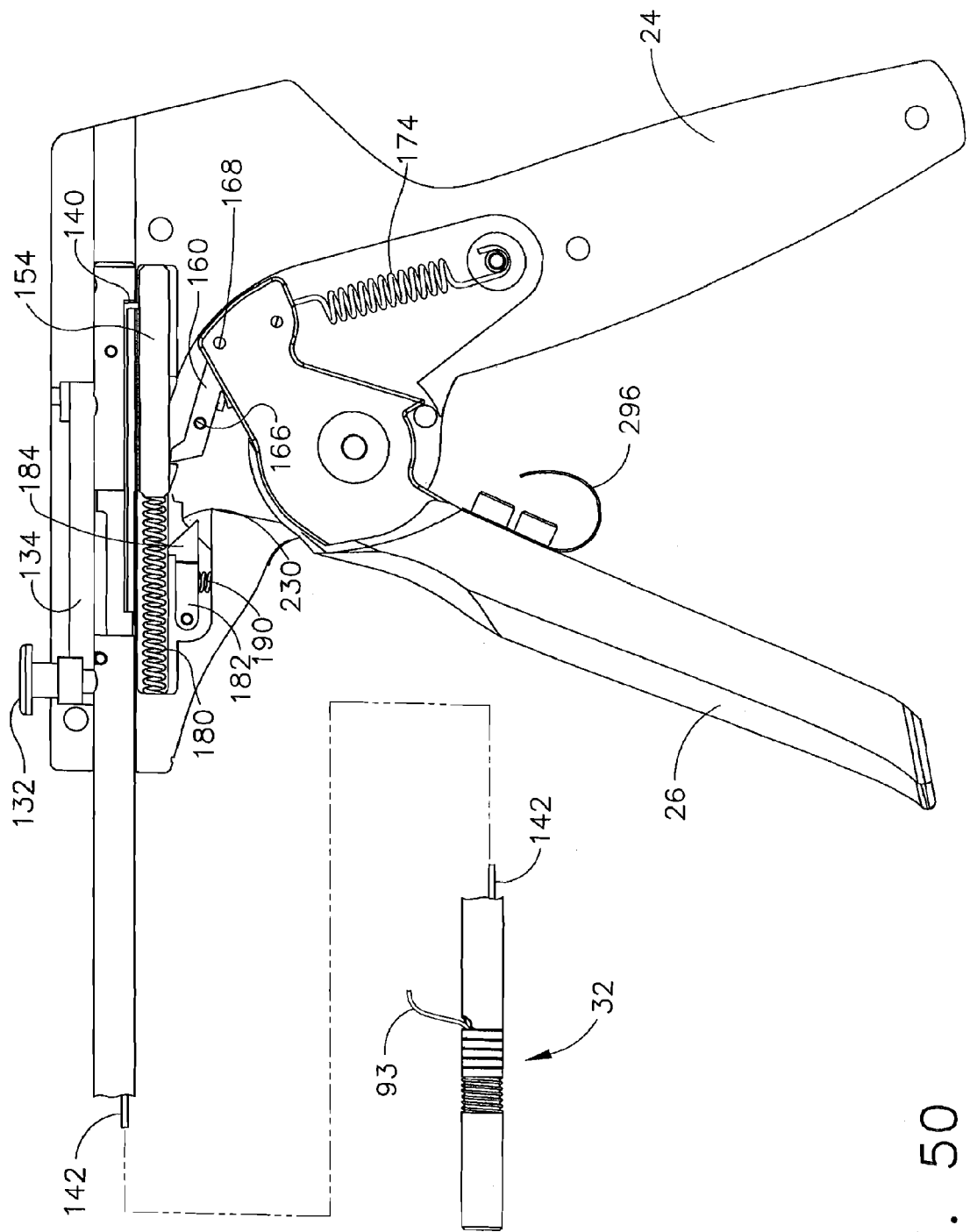
FIG. 50 is a side view of the third embodiment for the deploying device and attached cartridge, showing the handle with the outer casing partially removed and the cartridge and housing advanced distally.

In the third embodiment, a push rod is again provided within the deploying device for deploying T-Tag anchors from the cartridge. The push rod is stationary within a push rod sheath prior to T-Tag deployment. When cartridge 32 is attached to device housing 30, the push rod sheath again mates with the proximal end of the needle to connect the sheath to the needle, and align the push rod axially with the needle lumen. As shown in FIG. 50, in this embodiment handle 22 again includes a push rod activating mechanism for driving push rod 140 distally through the needle, when trigger 26 is squeezed. In this embodiment, a linkage, similar to that described in the second embodiment, is contained within handle 22. The linkage advances a drive pawl 160 in response to the pivoting of trigger 26. The drive pawl 160 initially engages a proximal, first tooth of a push rod driver 154. Push rod 140 is connected within push rod driver 154, in the same manner described above. When drive pawl 160 advances distally, push rod driver 154 also advances distally, moving push rod 140 in the direction of the T-Tag anchor stack in the needle. In this embodiment, the linkage advances the drive pawl 160 only the length of a single T-Tag anchor during each squeeze of trigger 26. Drive pawl 160, in turn, advances push rod 140 the length of one T-Tag anchor for each trigger squeeze.

Figure 51:
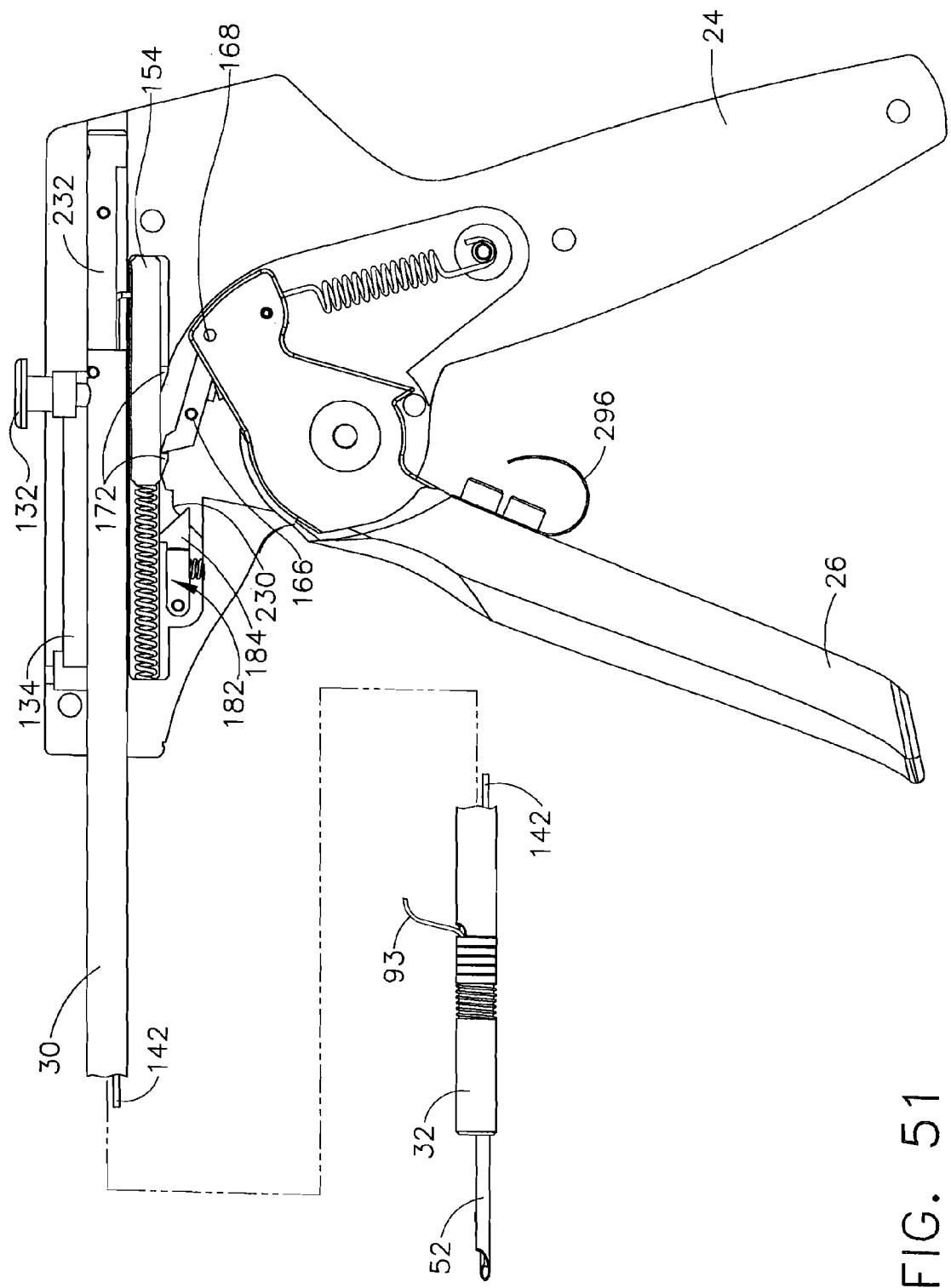
FIG. 51 is a side view of the deploying device and attached cartridge, similar to FIG. 50, showing the housing and cartridge in a proximal, fully retracted position to expose the distal end of the needle.

To discharge a T-Tag anchor, button 132 is slid proximally to retract housing 30 and attached cartridge 32 to expose needle 52 from the distal end of the cartridge, as shown in FIG. 51. Once needle 52 is fully exposed, button 132 is slid further proximally to pull the housing 30, cartridge 32, push-rod sheath (connected to the push rod sheath holder 232 inside the housing) as well as needle 52 in the proximal direction. Needle 52 is drawn proximally with cartridge 32 in order to draw the proximal end of the T-Tag anchor stack (inside the needle) into contact with the distal end of the stationary push rod 140 and advance the first T-Tag anchor to the distal end of the needle. Similar to the second embodiment, in this embodiment trigger 26 maintains the same stroke for deployment of both T-Tag anchors. With needle 52 exposed from cartridge 32, and push rod 140 in contact with the proximal end of the T-Tag anchor stack, trigger 26 is squeezed to deploy the first T-Tag anchor. As trigger 26 is squeezed, drive pawl 160 advances push rod driver 154 distally, causing push rod 140 to expel the first T-Tag anchor from the needle. After the T-Tag anchor is released, tactile feedback is provided to the surgeon. FIGS. 50 and 51 show an alternative tactile feedback embodiment using a resistance spring 296. Resistance spring 296 is attached to trigger 26 so as to face pistol grip 24. As trigger 26 is pivoted towards pistol grip 24, the outwardly bending free end of the spring 296 makes contact with the pistol grip. Resistance spring 296 has a high stiffness so that additional manual squeezing pressure is required to continue pivoting the trigger. Upon receipt of the tactile feedback, or otherwise upon completion of the trigger stroke, trigger 26 is released. As trigger 26 is released, drive pawl 160 moves back proximally to its initial position, in the manner described in the earlier embodiments. As the drive pawl 160 moves proximally, push rod driver 154 remains advanced due to contact with anti-backup pawl 182. Trigger 26 is then squeezed a second time to deploy the second T-Tag anchor from needle 52.

After the second T-Tag anchor is deployed, the device is reset in a manner similar to that described above for the first embodiment. Namely, trigger 26 is fully pivoted until flush against pistol grip 24. Fully pivoting trigger 26 drives drive pawl 160 further distally against anti-backup pawl 182, causing pin 166 to pivot anti-backup pawl catch 184 downwardly. As pin 166 advances against the anti-backup pawl catch, the pin also contacts cam surface 230 in the handle, which drives the pin and, correspondingly the pawls 160, 182 downward. As the pawls move downward, both pawls disengage from the push rod driver teeth 172, enabling the push rod driver 154 to spring back to its initial proximal position. As push rod driver 154 retracts, the driver pulls the push rod form needle 52 and resets the push rod back with the housing 30.

After the deploying device is reset, the loose suture end 86 is cinched to draw the T-Tag anchors together. Suture end 86 is preferably tensioned in this embodiment by grasping the suture by hand, and applying force to the suture along the axis of the housing 30. In this case, the suture is preferably long enough so that it passes through a trocar and the suture end 86 is located at or near the handle 22. After the T-Tags have been cinched to the desired position, the loose suture is severed. The suture may be severed with a cartridge cutting member, such as described above, or with other known types of surgical cutting instruments.

Figure 52:
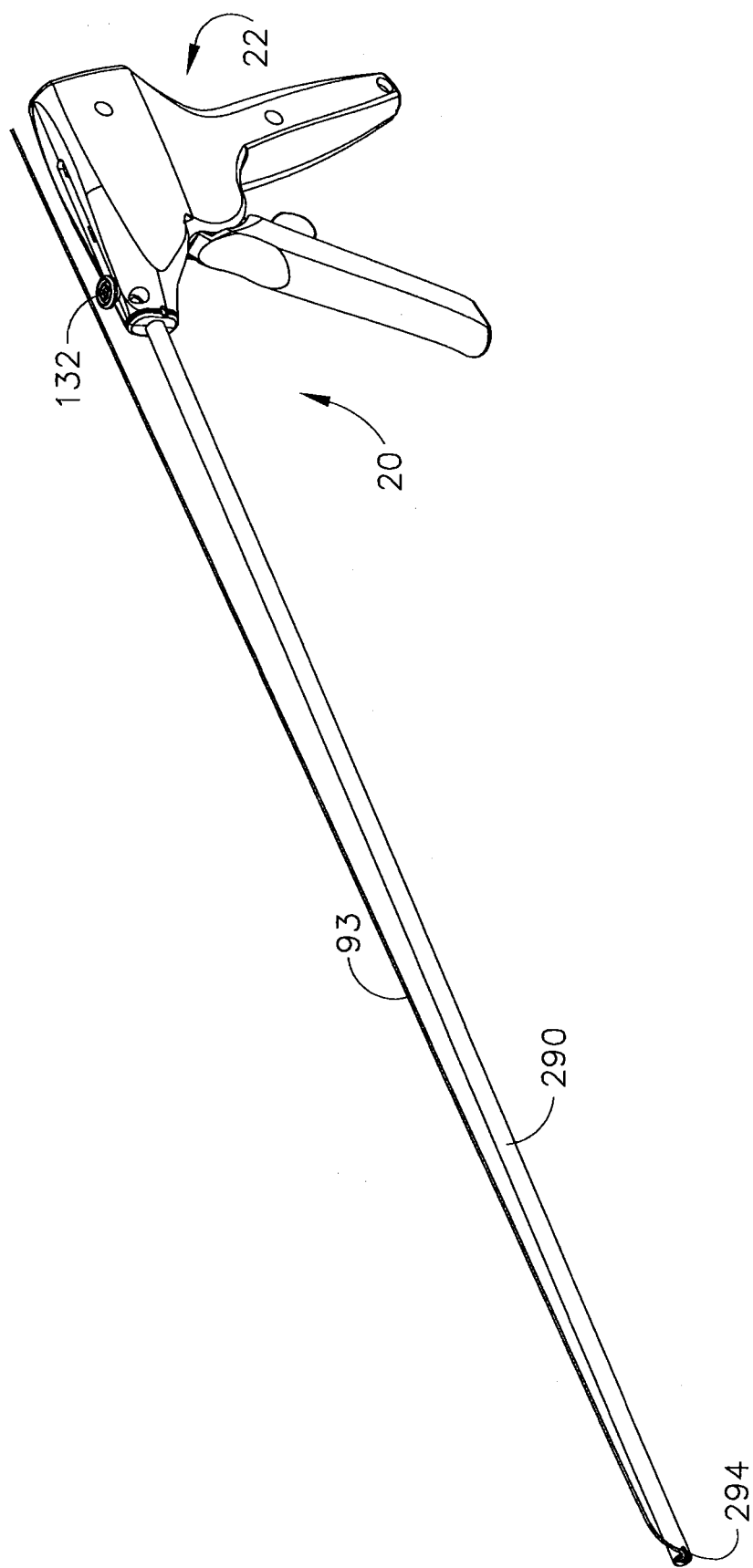
FIG. 52 is a perspective view showing a fourth embodiment for a deploying device and attached cartridge.
Figure 53:
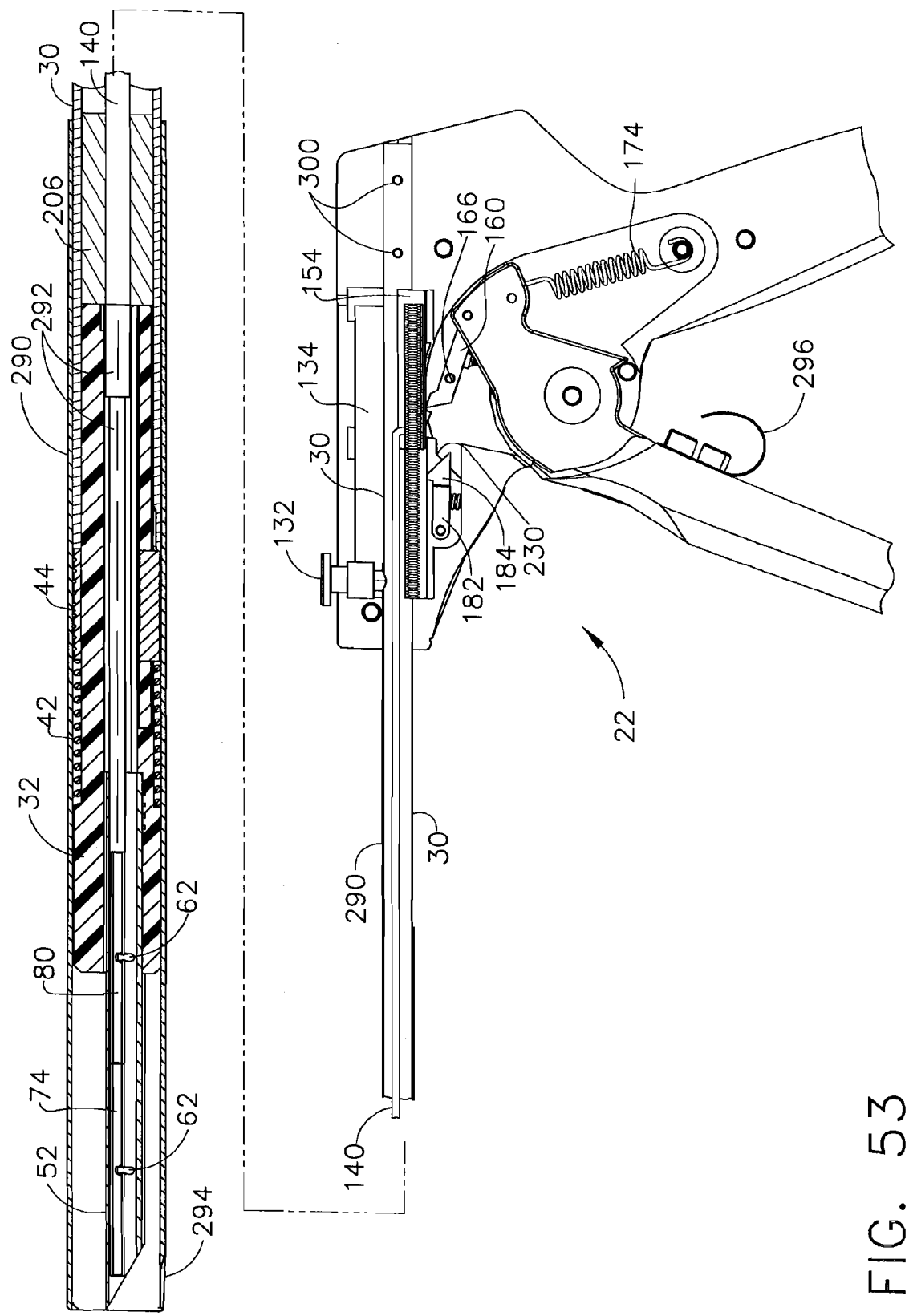
FIG. 53 is a sectional view of a cartridge and deploying device according to the fourth embodiment, showing the outer protective sheath in a fully distal position covering the needle.
Figure 54:
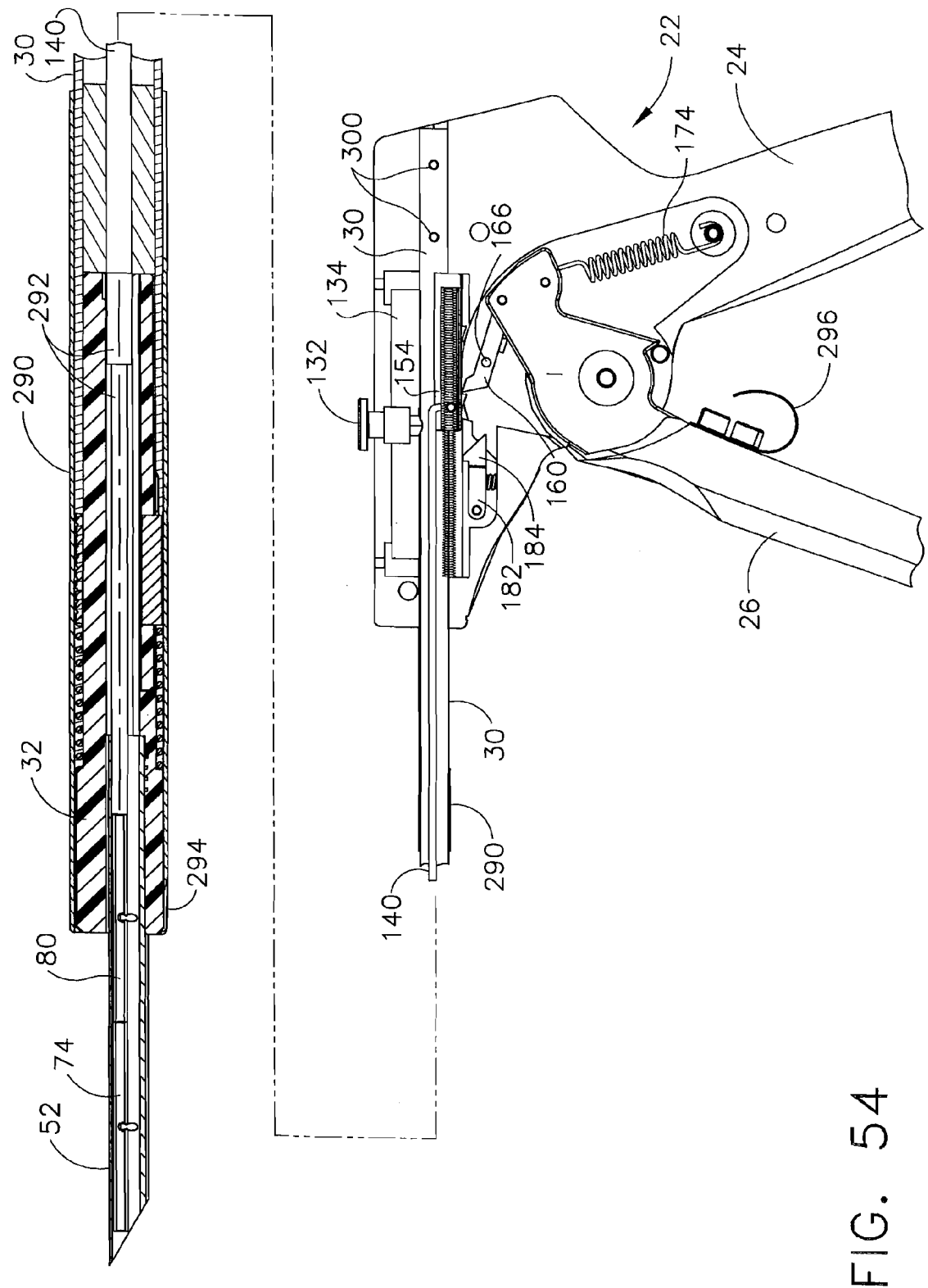
FIG. 54 is a sectional view of a cartridge and deploying device, similar to FIG. 53, showing the outer protective sheath in a partially retracted position to expose the needle.
Figure 55:
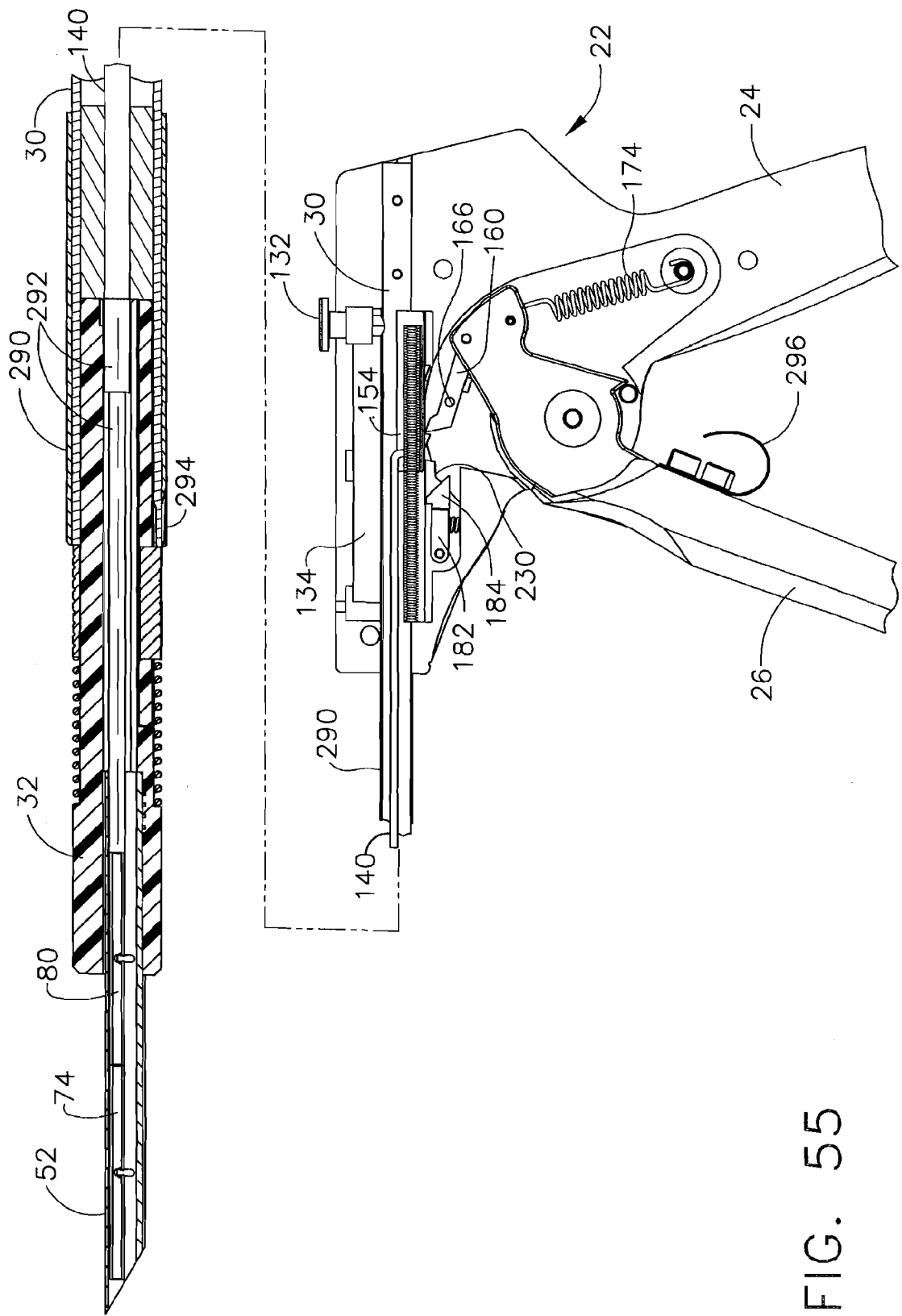
FIG. 55 is a sectional view of a cartridge and deploying device, similar to FIG. 54, showing the outer protective sheath in a fully retracted position to expose the cartridge coupling members allowing the cartridge to be removed.

FIG. 52 shows a fourth embodiment for the present invention, in which the deploying device is modified to include a protective outer sheath 290 that extends distally over the length of the cartridge. Outer sheath 290 extends proximally over housing 30 and is attached at a proximal end to button 132. In this embodiment, button 132 is attached to outer sheath 290 rather than housing 30, in order to retract and advance the outer sheath relative to the cartridge. Housing 30 is affixed in place within handle 22 by pins 300 located adjacent the proximal housing end, as shown in FIG. 53. A cutting means such as a V-notch 294 can be provided in the distal end of outer sheath 290 for severing suture following cinching. When button 132 is in a distal position, such as shown in FIG. 53, needle 52 is concealed within outer sheath 290. As button 132 is depressed to slide post 130 along track 134, the outer sheath 290 is retracted along the cartridge to expose needle 52 from the distal end of the cartridge 32, as shown in FIG. 54. When button 132 and attached post 130 are at the proximal end of track 134, as shown in FIG. 55, outer sheath 290 is in a fully retracted position and the cartridge coupling members, described above, are exposed to allow removal and replacement of the cartridge. In this embodiment, cartridge 32 is modified such that needle 52 is maintained in a fixed, exposed position at the distal end of the cartridge. The needle does not advance and retract through a needle channel as in the previous embodiments.

Figure 56:
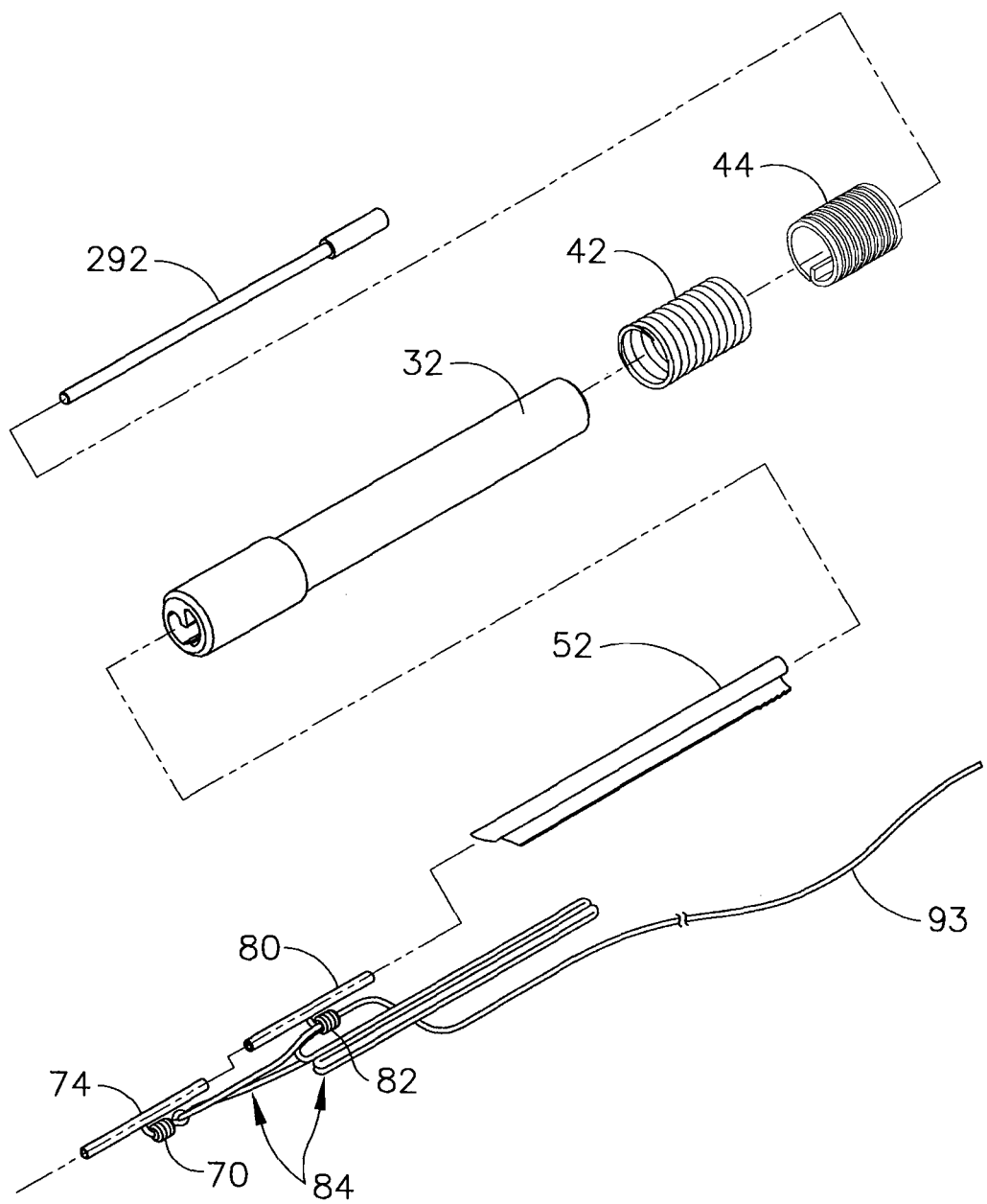
FIG. 56 is an exploded view of the fourth cartridge embodiment.
Figure 57:
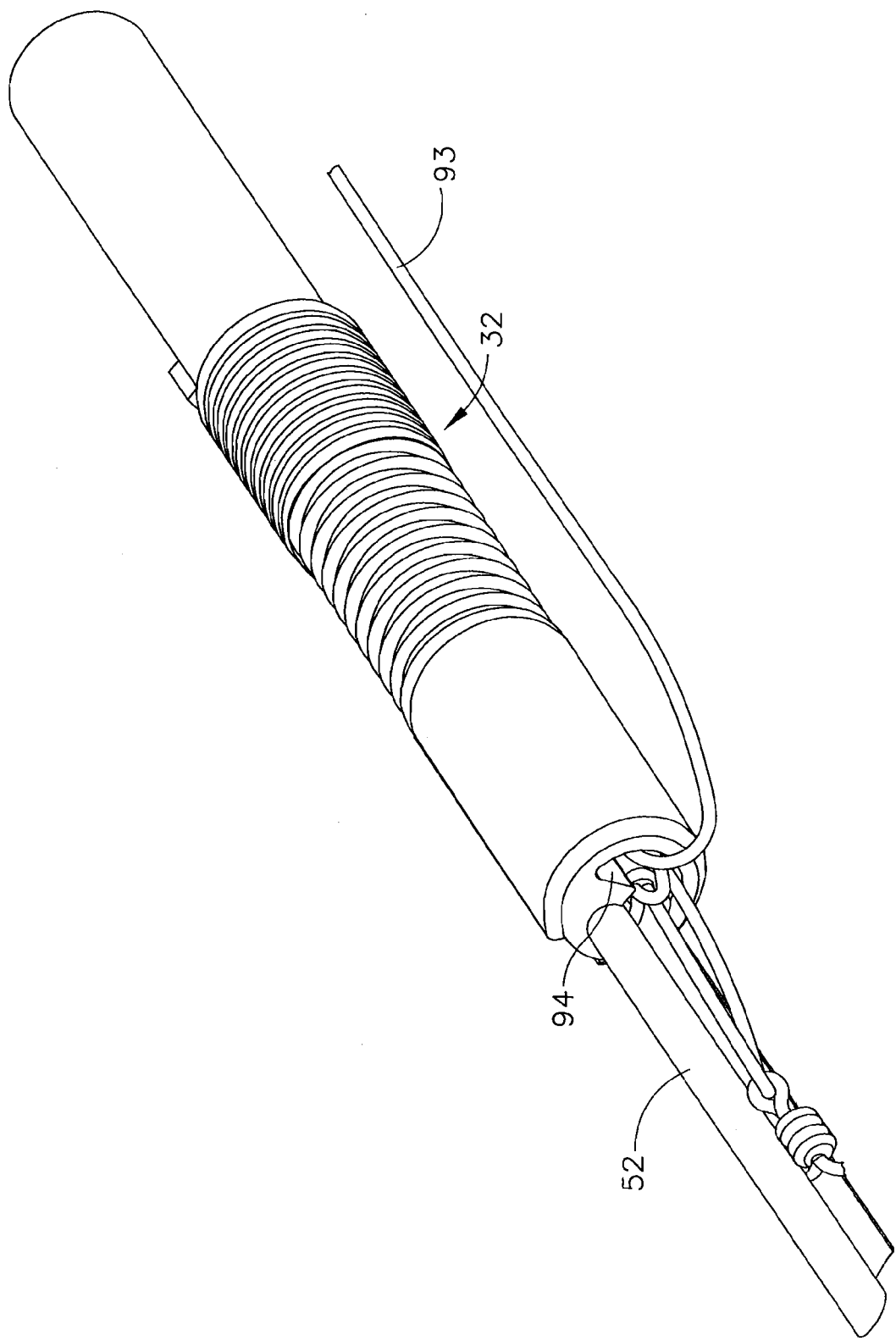
FIG. 57 is a perspective view of a cartridge according to the fourth embodiment.

As shown in FIG. 56, a pair of T-Tag anchors 74, 80 is preloaded into needle 52 for deployment by the device. The T-Tag anchors are stacked one behind the other at the distal end of the needle. Suture length 84 extending from the T-Tag anchors is held within a suture cavity 94 inside the cartridge via suture tab 298. The loose end 86 of the suture passes out of the distal end of suture cavity 94, as shown in FIG. 57. In this embodiment, a second push rod 292 (shown in FIG. 56) is provided within needle 52. Second push rod 292 extends through the needle lumen between the proximal end of the second T-Tag anchor 80 and the proximal end of cartridge 32. Also in this embodiment, a resistance spring 296, similar to the previous embodiment, may be attached between trigger 26 and pistol grip 24. As described above, resistance spring 296 comes into contact with pistol grip 24 as the trigger 26 is fully rotated towards the pistol grip. As the resistance spring 296 is compressed between the trigger 26 and the pistol grip 24, the spring provides tactile feedback of the T-Tag anchor deployment. As in previous embodiments, multiple methods exist for providing tactile feedback and may be interchangeably used.

Figure 58:
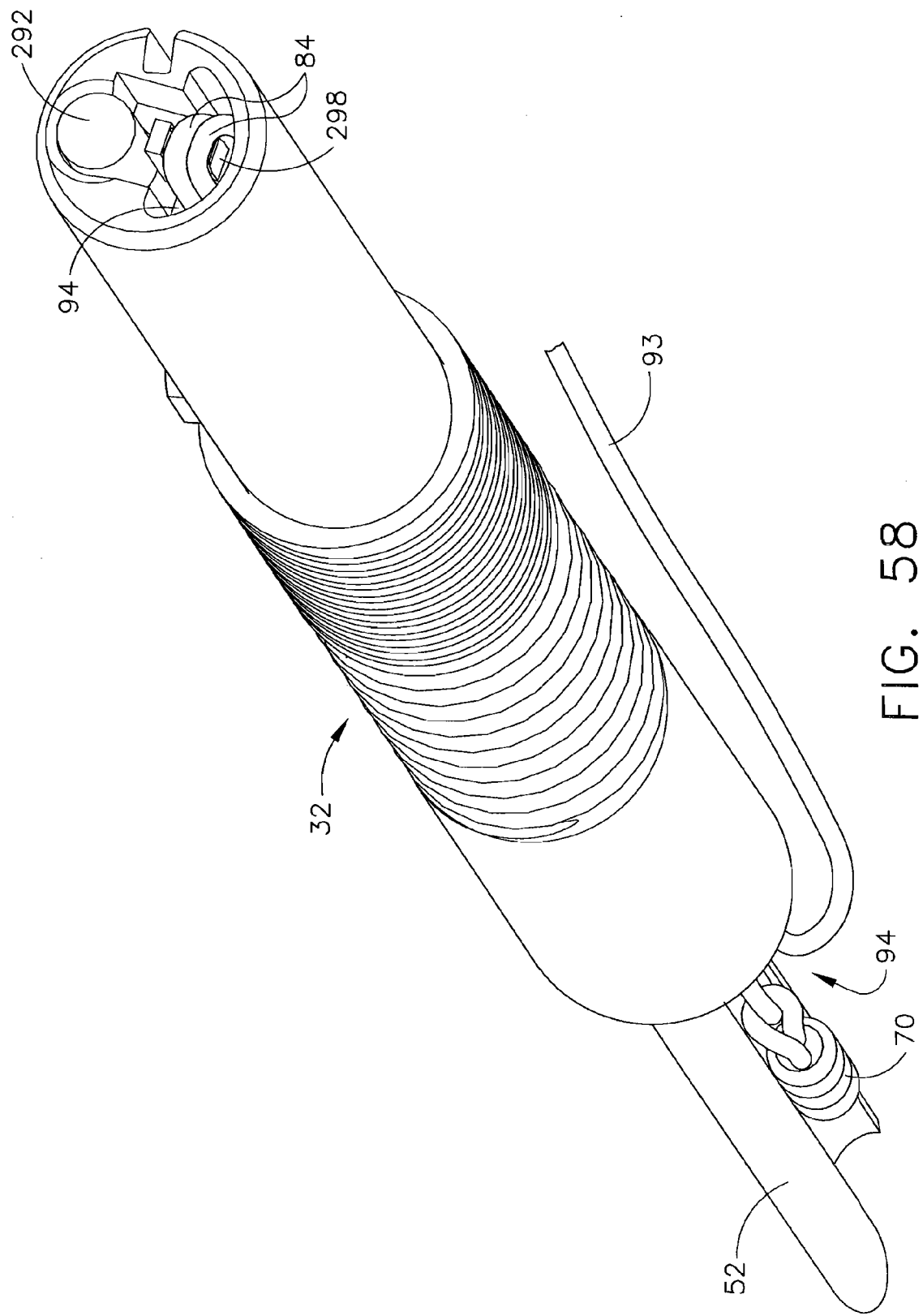
FIG. 58 is a perspective view showing the fourth embodiment cartridge from the proximal end.

When a cartridge is loaded onto the distal end of housing 30, by any of the methods described above, the distal end of push rod 140 in the housing is aligned with the proximal end of second push rod 292 in the cartridge. FIG. 58 shows the alignment of the push rods between the deploying device housing and the cartridge. To deploy a T-Tag anchor, outer sheath 290 is partially retracted, as shown in FIG. 54, to expose needle 52. The exposed needle is then inserted into tissue (not shown) at the desired location for the anchor. With needle 52 penetrating the tissue, trigger 26 is manually squeezed towards pistol grip 24. As trigger 26 pivots, the trigger applies a force to drive pawl 160 in the handle to advance the drive pawl distally. As drive pawl 160 advances, the drive pawl applies force to the distal tooth on the push rod driver 154 to also advance the push rod driver. The proximal end of push rod 140 is connected within push rod driver 154 (as in the previous embodiments), so that the distal movement of the push rod driver advances the push rod from the housing and into needle 52. As push rod 140 advances into needle 52, the push rod propels the second push rod 292 forward within the needle. For each squeeze of trigger 26, the drive pawl 160 and push rod driver 154 advance push rod 140 forward a distance equal to the length of a T-Tag anchor. Thus, push rod 140 (which extends from housing 30) advances the second push rod 292 in the cartridge a sufficient distance to expel the first T-Tag anchor from the needle tip. As the T-Tag anchor is deploying, resistance spring 296 contacts pistol grip 24. Continued squeezing of the trigger beyond this point thus requires additional pressure, signaling to the surgeon that the T-Tag anchor has been deployed and that the trigger can be released. After the pressure on trigger 26 is released, the trigger pivots back to the starting position under the force of drive pawl spring 174. As trigger 26 pivots back, drive pawl 160 also returns to its starting position within track 220 in the handle, in the manner described above. Push rod driver 154 remains advanced due to the contact with anti-backup pawl 182.

Upon squeezing the trigger again, drive pawl 160 applies force to the second (proximal) push rod driver tooth to again advance push rod 140 against second push rod 292 within needle 52. Push rod 140 drives second push rod 292 distally a sufficient distance to expel the second T-Tag anchor from needle 52. After the second T-Tag anchor is deployed, the device can be reset by fully pivoting trigger 26 flush against pistol grip 24 (against the resistance force of spring 296) to reset push rod driver 154 back to its initial position, in the same manner shown in FIG. 31 and described above for the first embodiment. After the deploying device is reset, button 132 is advanced distally to draw outer sheath 290 back over the tip of needle 52, as shown in FIG. 53. The distal end of outer sheath 290 is place against the tissue in a region sufficiently close to the second tissue anchor to provide resistance for suture cinching. To cinch the suture, suture end 86 is pulled proximally along the direction of the length of the housing 30. With resistance provided by the distal end of outer sheath 290, the tissue anchors are brought together as doubled over suture 84 is reduced in size. After cinching, suture 93 extending from knot 82 can then be manually drawn into notch 294 at the end of outer sheath 290, using the device itself, a grasper or other similar tool, to sever the loose end of the suture. After the suture is severed, the device can be removed from the trocar. After the device is removed, button 132 is retracted proximally to expose the cartridge coupling members, as shown m FIG. 55. The used cartridge can then be removed from the deploying device and replaced with a new cartridge in order to continue the procedure.

Figure 59:
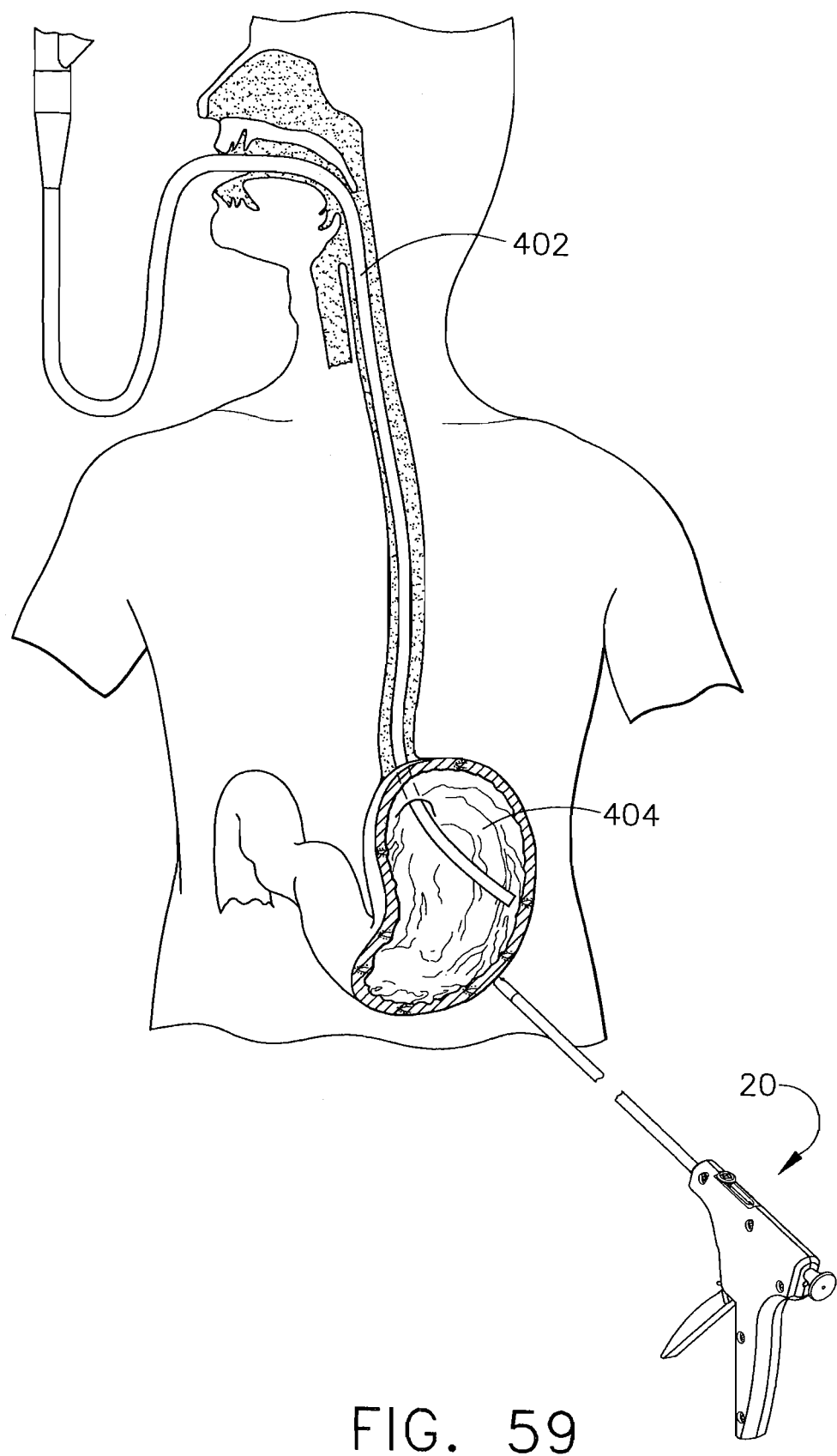
FIG. 59 is a schematic view of a patient during a hybrid endoscopic-laparoscopic procedure.

There are numerous surgical procedures wherein soft tissues such as, but not limited to tissues within the gastrointestinal tract are brought into approximation. Examples wherein such a device may have beneficial applications related to soft tissue apposition include the closure of various fistulae, perforations, ostomies, or intentional through and through incisions, the creation of temporary or permanent suspensions for tissue manipulation, and the reinforcement of staple lines created for other purposes. As mentioned above, an exemplary application of the fastener deploying device is in a laparoscopic GVR surgical procedure. FIG. 59 is an isometric view of a patient during a GVR procedure, in which folds are formed in the gastric cavity wall using a hybrid laparoscopic-endoscopic approach. In the hybrid approach, visualization of one or more fold locations is achieved by passing a flexible endoscope 402 transesophageally into the interior of the gastric cavity 404. The endoscope 402 provides insufflation, illumination, and visualization of the gastric cavity 404, as well as a passageway into the cavity. The gastric cavity 404 is insufflated through endoscope 402 to create a sufficiently rigid working surface that may be pierced without damaging the opposing wall of the cavity. Insufflation of the gastric cavity also allows the boundaries of the cavity and the desired location for a fold to be mapped out by external palpation of the abdomen.

Figure 60:
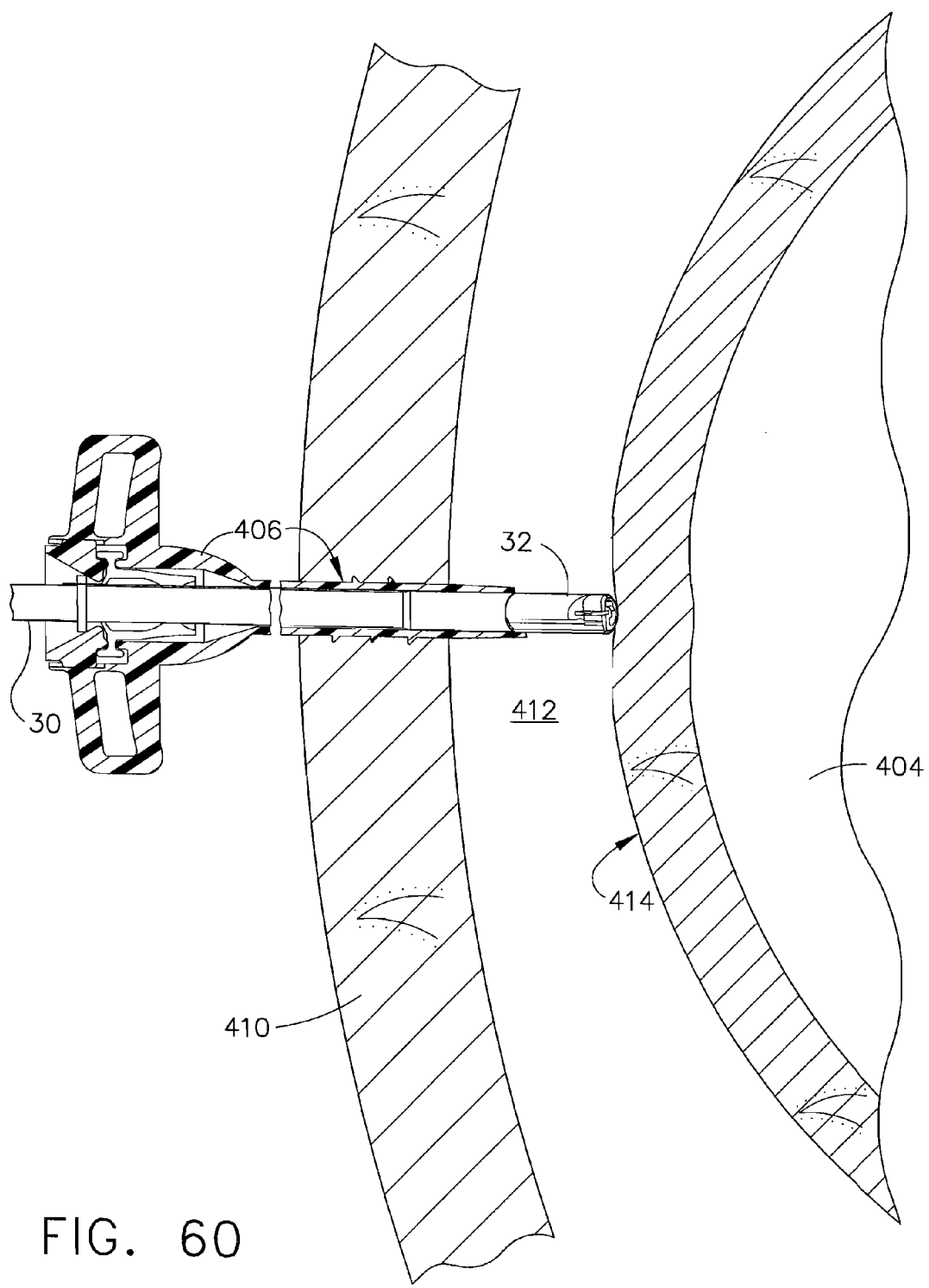
FIG. 60 is a cross-sectional view of an abdominal wall and gastric cavity showing the cartridge at the distal end of the deploying device probing tissue within the peritoneal cavity.

After gastric cavity 404 has been mapped through the endoscope 402, and the abdominal cavity insufflated if necessary, a trocar is inserted into the abdominal wall to provide access to the peritoneal cavity. FIG. 60 shows a trocar 406 inserted through an incision in abdominal wall 410. With the trocar 406 in place in the abdominal wall 410, fastener deploying device 20 of the present invention may be passed through the trocar and into the peritoneal cavity 412. Inside the peritoneal cavity, the distal end of cartridge 32 is pressed against the anterior wall of the cavity to probe the outside surface of the cavity. When probing the cavity wall, needle 52 is retracted into cartridge 32 (in the first through third embodiments) or covered by outer sheath 290 (in the fourth embodiment). The cavity wall indentation can be visualized through the endoscope to determine the proper location to insert needle 52. Laparoscopic visualization may be used in addition to or in place of the endoscopic view to determine the proper location. After the proper insertion location is determined, button 132 is slid along the top of the handle to expose the needle 52. In the case of the fourth embodiment described above, button 132 is slid proximally to retract the outer protective sheath 290 away from the exposed needle tip. The anterior cavity wall 414 is then punctured with the tip of the needle to reach the interior of the gastric cavity. Needle 52 is inserted into the cavity 404 with sufficient force to prevent the needle from glancing off of the exterior surface of the anterior cavity wall. With needle 52 inside the gastric cavity, the device trigger is squeezed to deploy the first T-Tag anchor into or through the cavity wall, in any of the manners described above.

Figure 61:
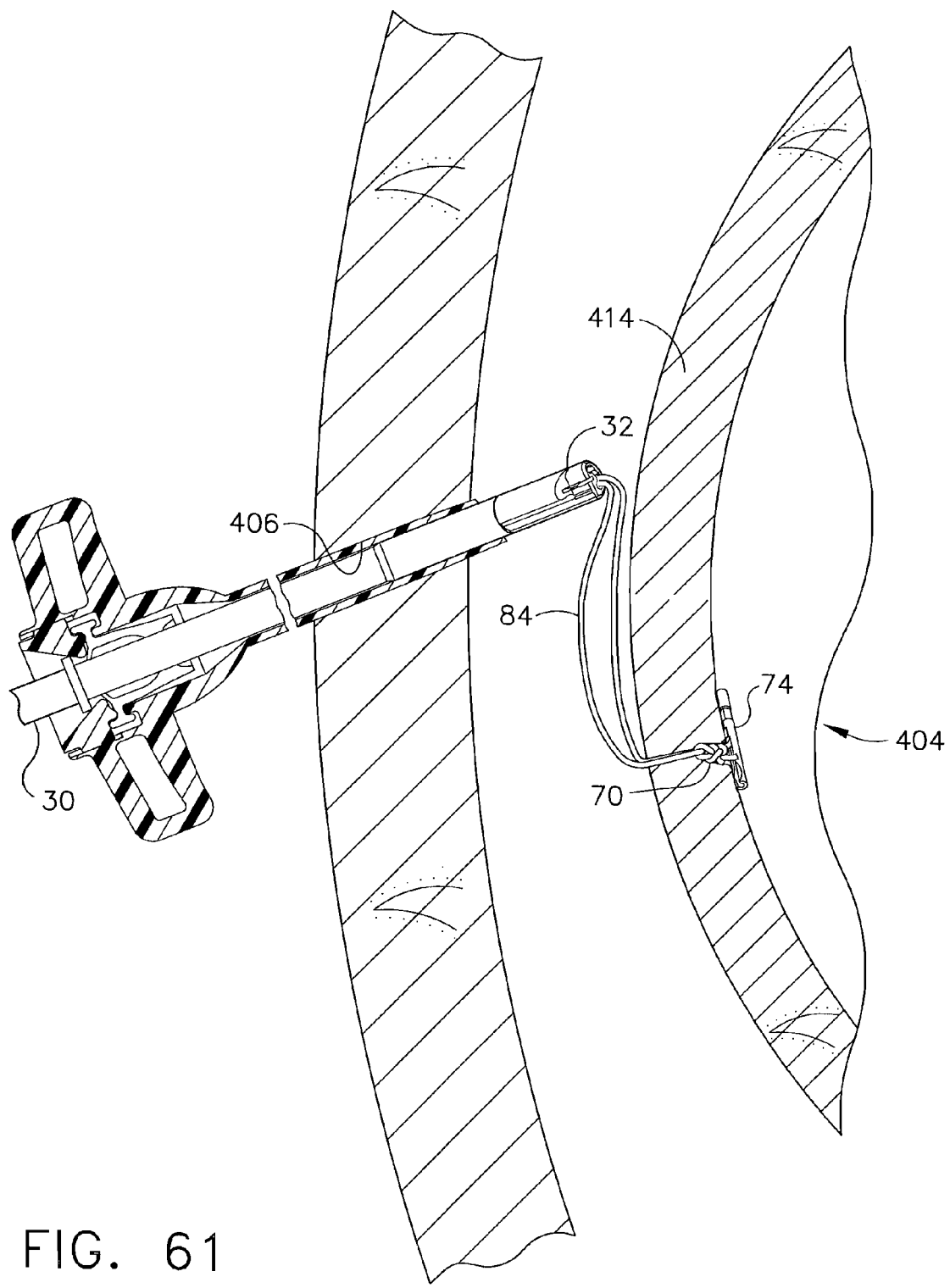
FIG. 61 is a cross-sectional view of an abdominal wall and gastric cavity showing the cartridge at the distal end of the deploying device probing the gastric cavity for a second suture anchor location.

After the first T-Tag anchor is deployed into cavity 404, needle 52 is removed from the cavity. In the preferred case where suture loop 70 tightly surrounds the suture of the doubled over suture 84, when needle 52 is removed, a portion of the suture remains in the cavity wall. Alternatively, if suture loop 70 is sufficiently large, as needle 52 is removed the suture loop is drawn from the first T-Tag anchor 74 back through the cavity wall. After needle 52 is removed from cavity 404, cartridge 32 (or protective sheath 290) is drawn back over the tip of the needle. The anterior wall is again probed with the distal cartridge end, as shown in FIG. 61, to determine the location for the second T-Tag anchor. Once the proper placement location is determined, needle 52 is once again exposed and inserted through anterior wall 414 into gastric cavity 404. With needle 52 inside gastric cavity 404, the second of the pre-tied T-Tag anchors 80 is deployed into the interior of the cavity.

After second T-Tag anchor 80 is deployed, needle 52 is removed from anterior wall 414, drawing the attached suture 84 back through the wall. With the two T-Tag anchors deployed through the cavity wall, the suture grasping member 200 is retracted (in the case of the initial two embodiments described above) to apply tension to the suture 84. As tension is applied to the suture, the tissue is drawn together and towards the deploying device, due to the loose end of the suture being retained within the cartridge. Where the loose end of suture 86 passes through the side suture opening 282 between the cartridge and housing (as in the third embodiment described above), or out the distal end of the cartridge 32 (as in the fourth embodiment described above), the suture may be tensioned manually by hand or by using a surgical instrument, such as a grasper, to pull on the suture. With the third device embodiment, manually pulling suture end 86 pulls the gastric wall into direct contact with the distal end of the cartridge. The resistance provided here as in the first two embodiments, allows the tissue anchors to be cinched together. However, with the fourth device embodiment, the distal end of the protective sheath is pressed against the anterior cavity wall to offer resistance during cinching and cutting. The additional resistance of the cartridge or sheath tip is necessary since the T-Tag anchors and suture are both free of the deploying device, thereby preventing the device from applying the resistance as is the case in the first three embodiments.

Figure 62:
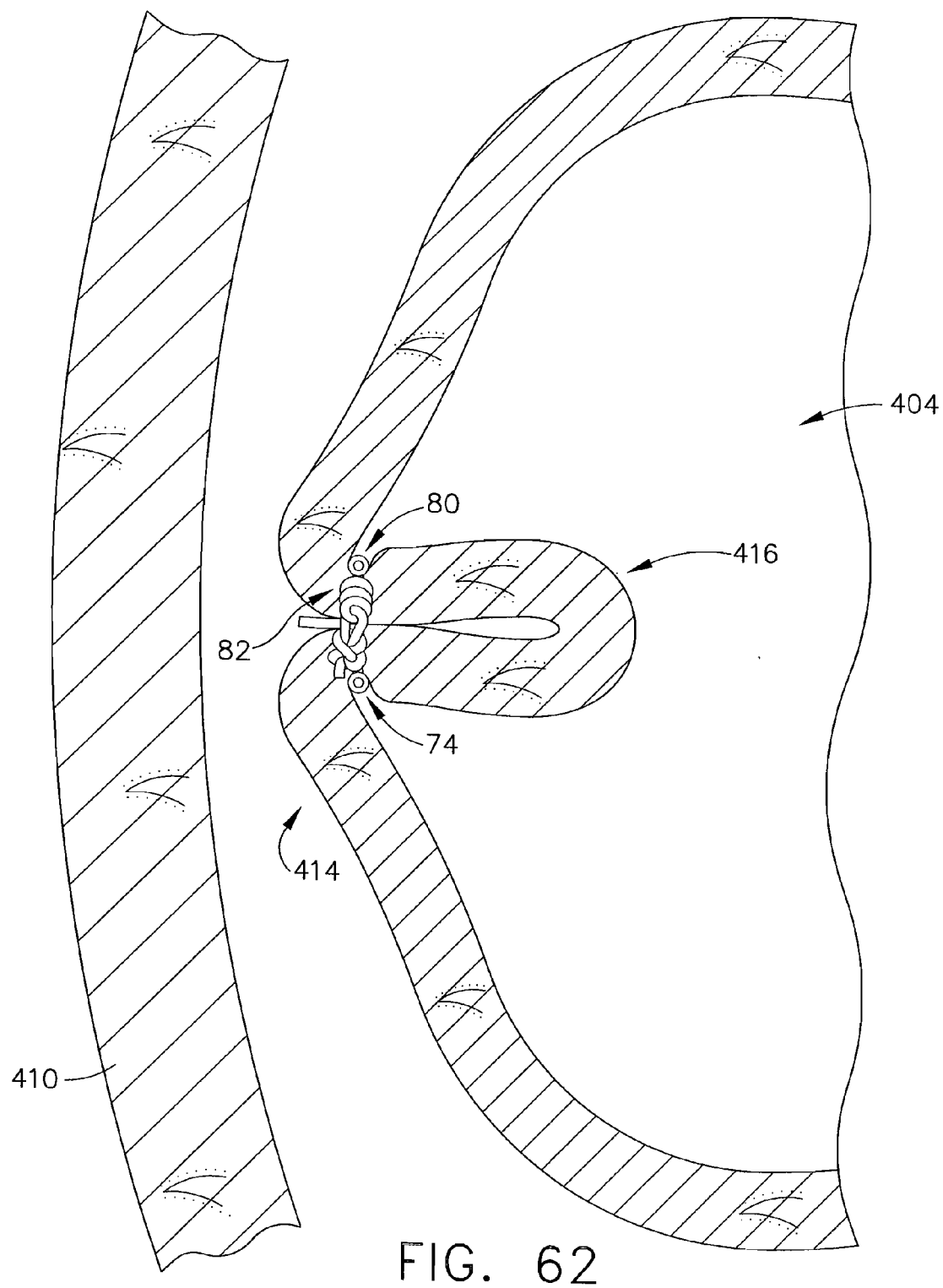
FIG. 62 is a cross-sectional view of an abdominal wall and gastric cavity showing a fastener forming and locking a fold in a gastric cavity wall.

As the suture is tensioned to reduce the size of the doubled over suture length 84, the T-Tag anchors 74, 80 are drawn together, apposing the serosal tissues surrounding each T-Tag anchor. After the T-Tag anchors and connecting suture have been utilized to appose the cavity wall, the remaining suture length is maneuvered into the cutting member on the cartridge or, alternatively, the cutting notch on the outer sheath. With tension applied to the proximal, loose end of the suture from either inside or outside of the deploying device, the device is retracted away from the T-Tag anchors, to draw the suture taut against the cutting edge and sever the suture. Following severing, the deploying device and the attached cartridge are withdrawn through the trocar, with the remaining length of suture retained within the cartridge. Alternatively, in the case of the third and fourth embodiments, the deploying device is removed from the peritoneal cavity, and the loose suture end 86 is subsequently withdrawn through the trocar by a grasper or other surgical tool. FIG. 62 shows a gastric cavity 404 with T-Tag anchors 74, 80 cinched and locked together by a slip knot 82 to appose the exterior, serosal layer of the gastric cavity wall and form a fold 416.

Figure 63:
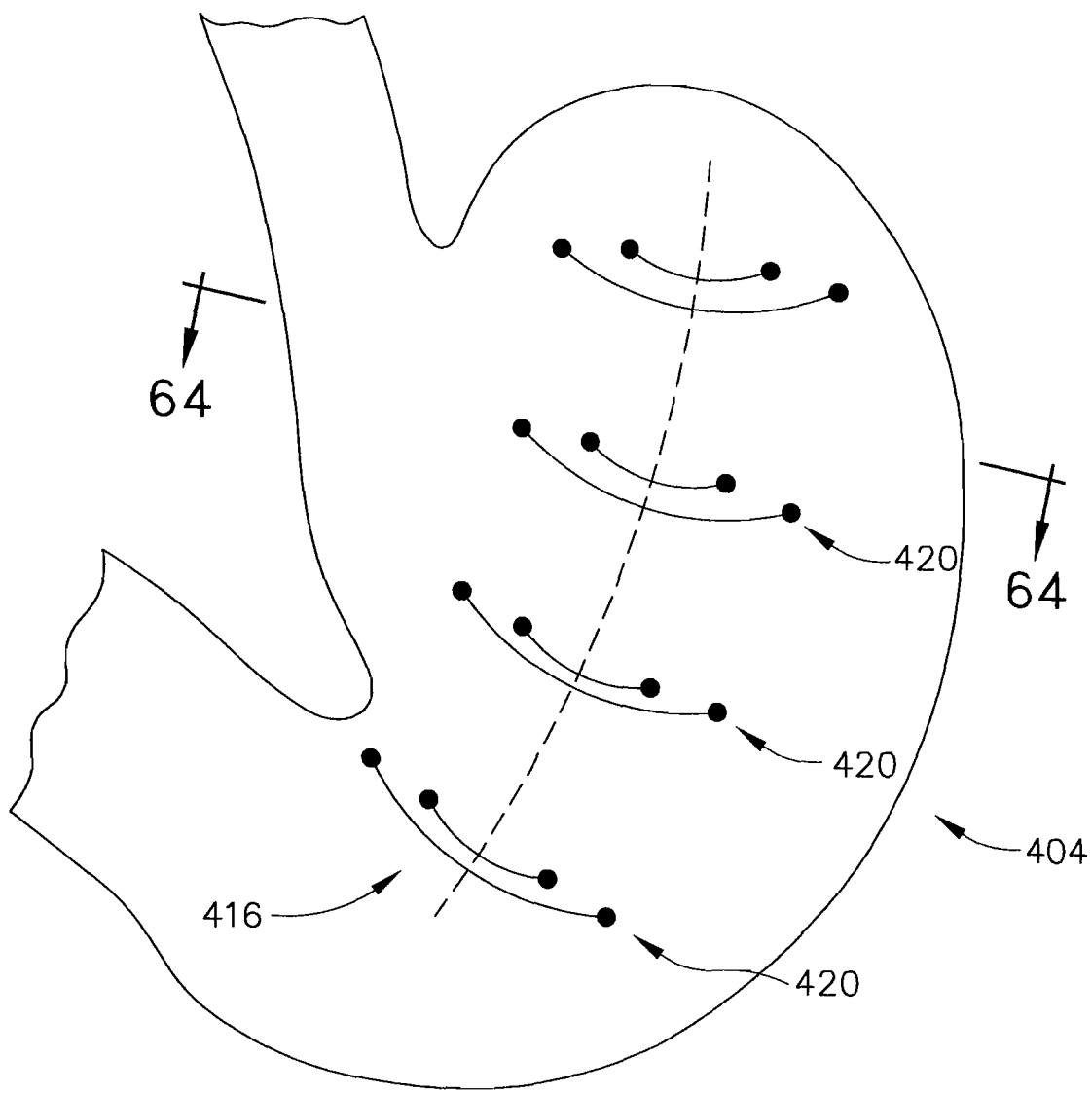
FIG. 63 is a diagrammatic, exterior view of a gastric cavity showing the placement of two series of fasteners.
Figure 64:
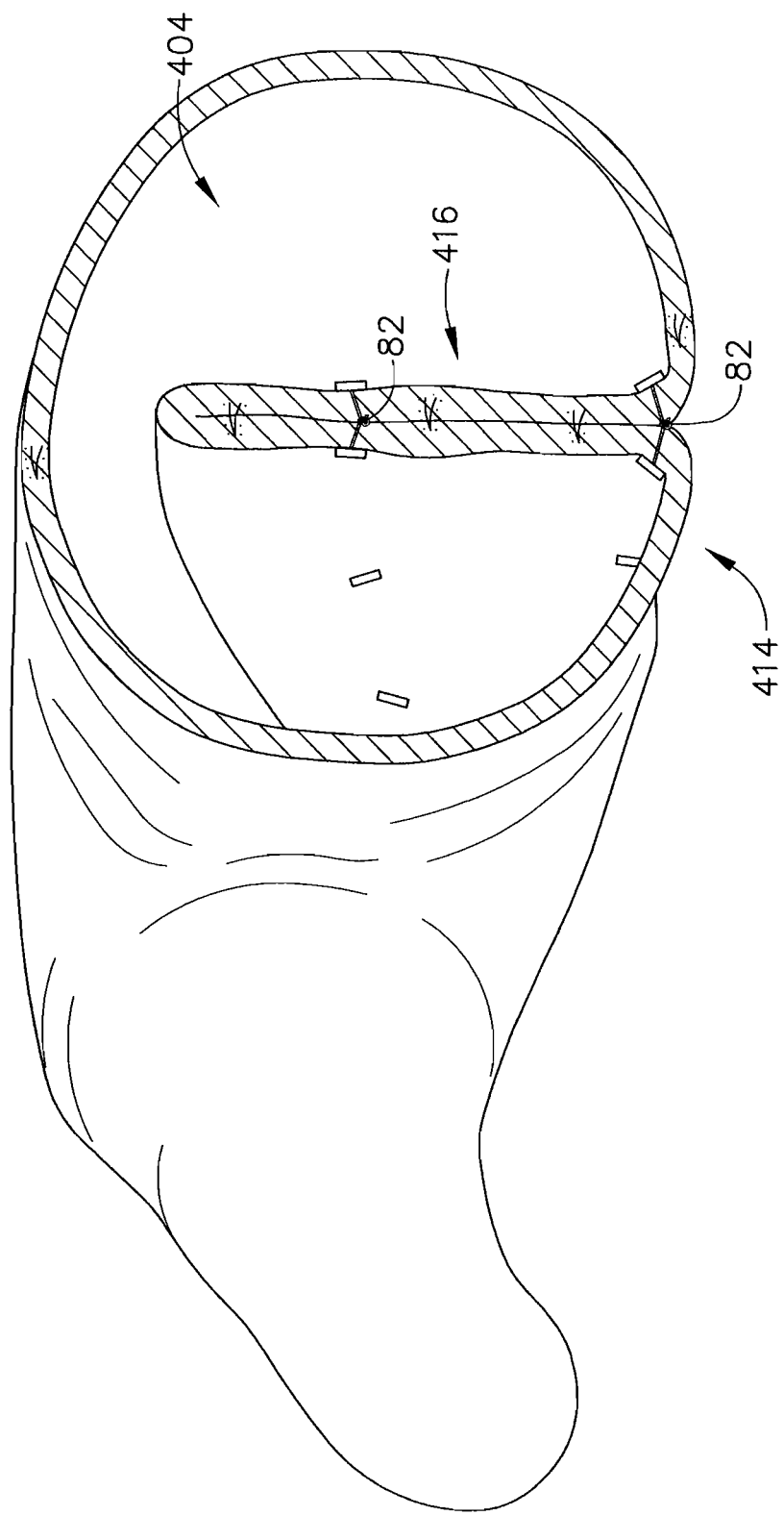
FIG. 64 is a cross-sectional view taken along line 64-64 of FIG. 63, showing the interior of a gastric cavity with a uniform wall fold.

As shown diagrammatically in FIG. 63, one or more additional fasteners, indicated by reference numeral 420, may be deployed along the cavity wall during a GVR procedure. The trocar may be flexed within the abdominal wall, or removed and repositioned within the abdominal wall as necessary, in order to reach all of the desired fastener locations. Suture material is cinched together between the T-Tag anchors in each fastener to extend the length of the cavity wall fold 416, as shown in FIGS. 63 and 64. The number of fasteners used to form a fold will depend upon the desired length for the fold and the desired spacing selected between fasteners. Preferably, each of the fasteners is evenly spaced apart along the length of the desired fold line. Likewise, within each fastener the T-Tag anchors are preferably evenly spaced apart across the fold line, so that a uniform tissue fold is formed preferably without distortion or bunching. The proper relative spacing of the suture anchoring devices can be ascertained through the endoscope. Alternatively, an additional trocar may be inserted into the abdominal wall and used in conjunction with an optical instrument to visually determine the proper locations for the suture anchoring devices laparoscopically.

The foregoing description of preferred embodiments of the invention has been presented for purposes of illustration and description. It is not intended to be exhaustive or to limit the invention to the precise form disclosed. Obvious modifications or variations are possible in light of the above teachings. The embodiments were chosen and described in order to best illustrate the principles of the invention and its practical application to thereby enable one of ordinary skill in the art to best utilize the invention in various embodiments and with various modifications as are suited to the particular use contemplated. It is intended that the scope of the invention be defined by the claims appended hereto.

What is claimed:

1. A method for approximating tissue within a body, said method comprising the steps of:
   a. providing a device comprising a handle, at least one actuator, an elongated hollow housing having a proximal end attached to said handle and a distal end extending therefrom, a first and second cartridge, each said cartridge containing at least one fastener comprises at least two anchors connected together by a non-resilient flexible suture which does not resist deformation under compressible loads, said first cartridge being releasably connected to said distal end of said hollow housing;

b. inserting said distal end of said housing and said first cartridge into a body while keeping said flexible suture within said cartridge, and deploying each anchor into tissue in a spaced apart position;

c. moving said anchors adjacent one another by moving said suture in a proximal direction;

d. removing said first cartridge from said body, and removing said first cartridge from said housing, and placing said second cartridge onto said housing thereby replacing said first cartridge with said second cartridge.

2. The method of claim 1 further including the steps of:
insertingsaid second cartridge into a body and deploying each anchor into tissue in a spaced apart position, and moving said anchors adjacent one another by moving said suture in a proximal direction.

3. The method of claim 1 further including the step of securing said anchors adjacent one another.

4. The method of claim 3, further including the step of cutting said suture after the step of securing said anchors adjacent one another.

\* \* \* \* \*